US006261561B1

(12) United States Patent
Stewart, Jr. et al.

(10) Patent No.: US 6,261,561 B1
(45) **Date of Patent: *Jul. 17, 2001**

(54) METHOD OF STIMULATING AN IMMUNE RESPONSE BY ADMINISTRATION OF HOST ORGANISMS THAT EXPRESS INTIMIN ALONE OR AS A FUSION PROTEIN WITH ONE OR MORE OTHER ANTIGENS

(75) Inventors: C. Neal Stewart, Jr., Greensboro, NC (US); Marian L. McKee, Great Falls, VA (US); Alison D. O'Brien, Bethesda, MD (US); Marian R. Wachtel, Albany, CA (US)

(73) Assignee: Henry M. Jackson Foundation for the Advancement of Military Medicine, Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/840,466

(22) Filed: Apr. 18, 1997

Related U.S. Application Data

(60) Provisional application No. 60/015,657, filed on Apr. 19, 1996, and provisional application No. 60/015,938, filed on Apr. 22, 1996.

(51) Int. Cl.[7] .................................................. A61K 39/395

(52) U.S. Cl. .................................... 424/184.1; 424/234.1; 536/23.71; 435/6; 435/69.1; 435/172.3; 435/252.3

(58) Field of Search .............................. 424/184.1, 234.1; 435/6, 69.1, 172.3, 252.3; 536/23.71

(56) References Cited

U.S. PATENT DOCUMENTS 4,736,017 4/1988 O'Hanley et al. .

(List continued on next page.)

FOREIGN PATENT DOCUMENTS

2078716 * 3/1994 (CA) .

(List continued on next page.)

OTHER PUBLICATIONS

Conrad, U. et al, Plant Mol. Biol., 1994, vol. 26(4), Nov., pp. 1023–1030.*

(List continued on next page.)

*Primary Examiner*—Lynette R F. Smith
*Assistant Examiner*—Ginny Allen Portner
(74) *Attorney, Agent, or Firm*—Finnegan, Henderson, Farabow, Garrett & Dunner, L.L.P.

(57) ABSTRACT

This invention satisfies needs in the art by providing intimin, the Enterohemorrhagic *Escherichia coli* (EHEC) adherence protein, alone or as a fusion protein with one or more other antigens, expressed by transgenic plants and the use of those plants as vehicles for stimulating a protective immune response against EHEC and the one or more other antigens. Various plant species are transformed to protect various animal species and also humans against EHEC, against pathogens expressing intimin-like proteins, and against pathogens expressing any of the one or more other antigens to which intimin may be fused.

The eae gene encoding intimin, a functional portion thereof, or a recombination that encodes a fusion protein is put under the control of a constitutive plant promoter in a plasmid and the plasmid is introduced into plants by the type of transformation appropriate for the particular plant species. The engineered plants expressing intimin or the intimin fusion protein are then fed to animals and/or humans to elicit the production of antibodies, which protect the animals/humans against EHEC colonization and infection, and against pathogens expressing the one or more other antigens and any cross-reactive antigens. The invention may also be practiced by expressing the intimin or intimin fusion protein in other host organisms such as bacteria, yeast, and fungi.

13 Claims, 23 Drawing Sheets

U.S. PATENT DOCUMENTS

| | | |
|---|---|---|
| 4,740,585 | 4/1988 | Schmidt et al. . |
| 5,049,500 | 9/1991 | Arnizen et al. . |
| 5,378,824 | 1/1995 | Bedbrook et al. . |
| 5,380,831 | 1/1995 | Adang et al. .................. 536/23.71 |
| 5,484,719 * | 1/1996 | Lam et al. ..................... 435/172.3 |
| 5,532,142 * | 7/1996 | Johnston et al. ................ 435/69.1 |
| 5,686,079 * | 11/1997 | Curtiss, III .................... 424/234.1 |
| 5,747,293 * | 5/1998 | Dougan et al. ................... 530/402 |
| 5,759,551 * | 6/1998 | Ladd et al. .................... 424/198.1 |
| 5,798,260 * | 8/1998 | Tarr et al. ..................... 435/252.3 |

FOREIGN PATENT DOCUMENTS

| | | |
|---|---|---|
| 0 222 835 B1 | 5/1987 | (EP) . |
| 0282042 | 9/1988 | (EP) . |
| 9002484 * | 3/1990 | (WO) . |
| 90/02484 | 3/1990 | (WO) . |
| 92/02820 | 2/1992 | (WO) . |
| 94/20135 | 9/1994 | (WO) . |
| 9425060 * | 11/1994 | (WO) . |
| 95/15678 | 6/1995 | (WO) . |
| 96/00233 | 1/1996 | (WO) . |
| 96/12801 | 5/1996 | (WO) . |

OTHER PUBLICATIONS

Anspach, F.B. et al, Sep. 8, 1995, J. of Chromatog. A, vol. 711(1), pp. 81–92.*

Witzgall, R. et al, Analytical Biochem, vol. 223(2), pp. 291–298, 1994, Dec.,*

Smith, J.S. et al, J. Virology, 1994, vol. 68(9), Sep., pp. 5721–5729.*

McKee, M.L. et al, May 21–25, 1995, Abs. 95$^{th}$ General Meeting, Am. Soc. Microbiol, p. 166, #B–5.*

McKee, Marion Little, Diss. Abs. Int. (1995), vol. 56, No. 7B, p. 3583, order#AA19540040.*

Louie, M. et al, Infect. & Immun., vol. 61(10), Oct. 1993, pp. 4085–4092.*

Frankel, G. et al, Infect. Immun, May 1994, vol. 62(5), May 1994, pp. 1835–1842.*

Barza, S. et al, Infect. Immun Sep. 1993, vol. 61(9), pp. 3825–3831.*

McDaniel, T.K. et al, Feb. 28, 1995, Proc. Natl. Acad. Sci, vol. 92(5), pp. 1664–1668.*

Chen, BPC et al, Gene, 1994, Feb. 11, vol. 139(1) pp. 73–75.*

Strauss, A. et al, FEMS Microbiol. Letters, vol. 127, Apr. 1, 1995, pp. 249–254.*

Schmidt, J. et al, Mol. Biol. Reports, 1993, vol. 8(3) Oct., pp. 223–230.*

Pasteur Merieux Connaught, Eur. Chem. News, vol. 63 (1656), p. 28, Feb. 27–Mar. 5, 1995.*

Boslego et al, Chapter 17, Vaccines and Immunotherapy, 1991, Pergamon Press, pp. 211–223, 1991.*

Frankel, G. et al, Infect. Immun., Dec. 1996, vol. 64(12), pp. 5315–5325.*

Simonet, M. et al, Infect & Immun., vol. 62(3), Mar. 1994, pp. 863–867.*

Agin, T.S. et al, Cytokines, Cholera and the gut, pp. 315–320, 1995, Nov.*

Corporate Source, Bioresearch Ireland Forbairt, Glasnevin Dublin 9, Ireland, p. 1P, Dec. 11, 1995.*

Hengen, PN, Trends in Biochem. Sci., 1995, vol. 20(7) Jul., pp. 285–286.*

O'Brien, A.D. et al, Nov. 14–16, 1996, Abs.: Third Second Conference on Cholera and Diarrheal Diseases, Nagasaki, Japan.*

Oswald, T. et al, Analyti. Biochem, May 1, 1996, vol. 236(2), pp. 357–358.*

Schmitz, M.L. et al, Biotechniques, vol. 17(4), 1994, pp. 714–716 & 718.*

Von Brunn, A. et al, AIDS REsearch & Human retro viruses, vol. 11(12) 1995.*

Abstract: C. Neal Stewart, Jr.; Marian R. Wachtel; Stephen A. Mabon; William B. Warrick; and Alison D. O'Brien, "Expression of Enterohemorrhagic *Escherichia Coli* Intimin in Transgenic Plants: An Edible Anti–EHEC 0157:H7 Vaccine Candidate," VTEC Meeting held in Baltimore, Maryland on Jun 22–26, 1997.*

Abstract: Marian R. Wachtel; Lisa J. Gansheroff; and Alison D. O'Brien, "Structure–Function Analysis, Purification, and Immunoreactivity of Enterohemorrhagic *Escherichia Coli* Intimin," VTEC Meeting held in Baltimore, Maryland on Jun. 22–26, 1997.*

Hawley's Condensed Chemical Dictionary, 12th Ed., R.J. Lewis, Sr., Ed., p. 25 (1993).

Beebakhee et al., "Cloning and Nucleotide Sequence of the eae Gene Homologue from Enterohemorrhagic *Escherichia coli* Serotype 0157:H7", FEMS Microbio. Ltrs, vol. 91 pp. 63–68 (1992).

Dalsgaard et al., "Plant–Derived Vaccine Protects Target Animals Against a Viral Disease", Nature Biotechnology, 15:248–252 (1997).

De Aizpurua and Russell–Jones, "Oral Vaccination: Identification of Classes of Proteins that Provoke an Immune Response Upon Oral Feeding", J. Exp. Med, 167:440–451 (1988).

Donnenberg et al., "The Role of the eae Gene of Enterohemorrhagic *Escherichia coli* in Intimate Attachment In Vitro and in a Porcine Model", J. Clin. Invest., 92:1418–1424 (Sep. 1993).

Frankel et al., "Characterization of the C–Terminal Domains of Intimin–Like Proteins of Enteropathogenic and Enterohemorrhagic *Escherichia coli,* Citrobacter, and *Hafnia alvei*", Infection and Immunity, 62(5):1835–1842 (May 1994).

Frankel et al., "Molecular Characterization of a Carboxy-–Terminal Eukaryotic–Cell–Binding Domain of Intimin from Enteropthogenic *Escherichai coli*" Infection and Immunity, 63(11):4323–4328 (Nov. 1995).

Haq et al., "Oral Immunization with a Recombinant Bacterial Antigen Produced in Transgenic Plants", Science, 268:714–716 (May 1995).

Hochuli, "Purification of Recombinant Proteins with Metal Chelate Adsorbent", Genetic Engineering, Principles & Practice (J. Setlow, ed) Plenum, New York, 12:87–98 (1990).

Jerse and Kaper, "The eae Gene of Enteropathogenic *Escherichia coli* Encodes a 94–Kilodalton Membrane Protein, the Expression of Which is Influenced by the EAF plasmid", Infection and Immunity, 59(12):4302–4309 (Dec. 1991).

Levine et al., "The Diarrheal Response of Humans to Some Classic Serotypes of Enteropathogenic *Escherichia coli* is Dependent on a Plasmid Encoding an Enteroadhesiveness Factor", J. Infect. Dis., 152(3):550–559 (Sep. 1985).

Little et al., "Human Antibody Libraries in *Escherichia coli*", J. Biotech, 41:187–195 (1995).

Louie et al., "Expression and Characterization of the eaeA Gene Product of *Escherichia coli* Serotype 0157:H7", Infection and Immunity, 61(10):4085–4092 (Oct. 1993).

Mason and Arntzen, "Transgenic Plants as Vaccine Production Systems", TIBTECH, 13:388–392 (Sep. 1995).

McKee and O–Brien, "Truncated Enterohemorrhagic *Escherichia coli* (EHEC) 0157:H7 Intimin (EaeA) Fusion Proteins Promote Adherence of EHEC Strains to HEp–2 Cells", Infection and Immunity, 64(6):2225–2233 (Jun. 1996).

McKee et al., "Enterohemorrhagic *Escherichia coli* 0157:H7 Requires Intimin to Colonize the Gnotobiotic Pig Intestine and to Adhere to HEp–2 Cells", Infection and Immunity, 63(9):3739–3744 (Sep. 1995).

McKee and O'Brien, "Investigation of Enterohemorrhagic *Escherichia coli* 0157:H7 Adherence Characteristics and Invasion Potential Reveals a New Attachment Pattern Shared by Intestinal *E. coli*", Infection and Immunity, 64(5):2070–2074 (May 1995).

Skerra, "Bacterial Expression of Immunoglobulin Fragments", Current Opinion in Immunology, 5:256–262 (1993).

Yu and Kaper, "Cloning and Characterization of the eae Gene of Enterohaemorrhagic *Escherichia coli* 0157:H7", Molecular Biology, 6(3):411–417 (1992).

McKee and O'Brien, Abstract B–5, Abstracts of the 95th General Meeting of the American Society for Microbiology (Abstracts sent out Apr. 21, 195).

Database Dissabs an 95:64682 (1995) McKee, M.L. "Adherence of Enterohemorrhagic *Escherichia coli* to Human Epithelial Cells: The Role of Intimin (Bloody Diarrhea, Renal Failure, Hemorrhagic Colitis)" XP002040904, Abstract: McKee, M.L., Dissertation 1995, Available Dissertation Abstracts International Order No: AA19540040.

International Search Report of International Application No. PCT/US97/05831.

O'Brien et al., "Intimin: Candidate for an *Escherichia coli* 0157:H7 Anti–Transmission Vaccine", Abstracts: Thirty Second Conference on Cholera and Related Diarrheal Diseases, Nagasaki University Pompe Hall (Nov. 14–16, 1996).

English Abstract of European Application No. 0282042.

* cited by examiner

```
  1  MITHGCYTRT RHKHKLKKTL IMLSAGLGLF FYVNQNSFAN GENYFKLGSD
 51  SKLLTHDSYQ NRLFYTLKTG ETVADLSKSQ DINLSTIWSL NKHLYSSESE
101  MMKAAPGQQI ILPLKKLPFE YSALPLLGSA PLVAAGGVAG HTNKLTKMSP
151  DVTKSNMTDD KALNYAAQQA ASLGSQLQSR SLNGDYAKDT ALGIAGNQAS
201  SQLQAWLQHY GTAEVNLQSG DNFDGSSLDF LLPFYDSEKM LAFGQVGARY
251  IDSRFTANLG AGQRFFLPAN MLGYNVFIDQ DFSGDNTRLG IGGEYWRDYF
301  KSSVNGYFRM RRWHESYHKK DYDERPANGF DIRFNGYLPS YPALGAKLIY
351  EQYYGDNVAL FNSDKLQSNP GAATVGVNYT PIPLVTMGID YRHGTGNEND
401  LLYSMQFRYQ FDKSWSQQIE PQYVNELRTL SGSRYDLVQR NNNIILEYKK
451  QDILSLNIPH DINGTEHSTQ KIQLIVKSKY GLDRIVWDDS ALRSQGGQIQ
501  HSGSQSAQDY QAILPAYVQG GSNIYKVTAR AYDRNGNSSN NVQLTITVLS
551  NGQVVDQVGV TDFTADKTSA KADNADTITY TATVKKNGVA QANVPVSFNI
601  VSGTATLGAN SAKTDANGKA TVTLKSSTPG QVVVSAKTAE MSSALNASAV
651  IFFDQTKASI TEIKADKTTA VANGKDAIKY TVKVMKNGQP VNNQSVTFST
701  NFGMFNGKSQ TQATTGNDGR ATITLTSSSA GKATVSATVS DGAEVKATEV
751  TFFDELKIDN KVDIIGNNVR GELPNIWLQY GQFKLKASGG DGTYSWYSEN
801  TSIATVDASG KVTLNGKGSV VIKATSGDKQ TVSYTIKAPS YMIKVDKQAY
851  YADAMSICKN LLPSTQTVLS DIYDSWGAAN KYSHYSSMNS ITAWIKQTSS
901  EQRSGVSSTY NLITQNPLPG VNVNTPNVYA VCVE  SEQ ID NO:19
```

FIG. 2

```
   1 TCGAGAATGA AATAGAAGTC GTTGTTAAGT CAATGGAAAA CCTGTATTTG GTATTACATA
  61 ATCAGGGAAT AACATTAGAA AACGAACATA TGAAAATAGA GGAAATCAGT TCAAGCGACA
 121 ATAAACATTA TTACGCCGGA AGATAAAATC CGATCTATTA ATATAATTTA TTTCTCATTC
 181 TAACTCATTG TGGTGGAGCC ATAACATGAT TACTCATGGT TGTTATACCC GGACCCGGCA
 241 CAAGCATAAG CTAAAAAAAA CATTGATTAT GCTTAGTGCT GGTTTAGGAT TGTTTTTTTA
 301 TGTTAATCAG AATTCATTTG CAAATGGTGA AAATTATTTT AAATTGGGTT CGGATTCAAA
 361 ACTGTTAACT CATGATAGCT ATCAGAATCG CCTTTTTTAT ACGTTGAAAA CTGGTGAAAC
 421 TGTTGCCGAT CTTTCTAAAT CGCAAGATAT TAATTTATCG ACGATTTGGT CGTTGAATAA
 481 GCATTTATAC AGTTCTGAAA GCGAAATGAT GAAGGCCGCG CCTGGTCAGC AGATCATTTT
 541 GCCACTCAAA AAACTTCCCT TTGAATACAG TGCACTACCA CTTTTAGGTT CGGCACCTCT
 601 TGTTGCTGCA GGTGGTGTTG CTGGTCACAC GAATAAACTG ACTAAAATGT CCCCGGACGT
 661 GACCAAAAGC AACATGACCG ATGACAAGGC ATTAAATTAT GCGGCACAAC AGGCGGCGAG
 721 TCTCGGTAGC CAGCTTCAGT CGCGATCTCT GAACGGCGAT TACGCGAAAG ATACCGCTCT
 781 TGGTATCGCT GGTAACCAGG CTTCGTCACA GTTGCAGGCC TGGTTACAAC ATTATGGAAC
 841 GGCAGAGGTT AATCTGCAGA GTGGTAATAA CTTTGACGGT AGTTCACTGG ACTTCTTATT
 901 ACCGTTCTAT GATTCCGAAA AAATGCTGGC ATTTGGTCAG GTCGGAGCGC GTTACATTGA
 961 CTCCCGCTTT ACGGCAAATT TAGGTGCGGG TCAGCGTTTT TTCCTTCCTG CAAACATGTT
1021 GGGCTATAAC GTCTTCATTG ATCAGGATTT TTCTGGTGAT AATACCCGTT TAGGTATTGG
1081 TGGCGAATAC TGGCGAGACT ATTTCAAAAG TAGCGTTAAC GGCTATTTCC GCATGAGCGG
1141 CTGGCATGAG TCATACAATA AGAAAGACTA TGATGAGCGC CCAGCAAATG GCTTCGATAT
1201 CCGTTTTAAT GGCTATCTAC CGTCATATCC GGCATTAGGC GCCAAGCTGA TATATGAGCA
1261 GTATTATGGT GATAATGTTG CTTTGTTTAA TTCTGATAAG CTGCAGTCGA ATCCTGGTGC
1321 GGCGACCGTT GGTGTAAACT ATACTCCGAT TCCTCTGGTG ACGATGGGGA TCGATTACCG
1381 TCATGGTACG GGTAATGAAA ATGATCTCCT TTACTCAATG CAGTTCCGTT ATCAGTTTGA
1441 TAAATCGTGG TCTCAGCAAA TTGAACCACA GTATGTTAAC GAGTTAAGAA CATTATCAGG
1501 CAGCCGTTAC GATCTGGTTC AGCGTAATAA CAATATTATT CTGGAGTACA AGAAGCAGGA
1561 TATTCTTTCT CTGAATATTC CGCATGATAT TAATGGTACT GAACACAGTA CGCAGAAGAT
1621 TCAGTTGATC GTTAAGAGCA AATACGGTCT GGATCGTATC GTCTGGGATG ATAGTGCATT
1681 ACGCAGTCAG GGCGGTCAGA TTCAGCATAG CGGAAGCCAA AGCGCACAAG ACTACCAGGC
1741 TATTTTGCCT GCTTATGTGC AAGGTGGCAG CAATATTTAT AAAGTGACGG CTCGCGCCTA
1801 TGACCGTAAT GGCAATAGCT CTAACAATGT ACAGCTTACT ATTACCGTTC TGTCGAATGG
1861 TCAAGTTGTC GACCAGGTTG GGGTAACGGA CTTTACGGCG GATAAGACTT CGGCTAAAGC
1921 GGATAACGCC GATACCATTA CTTATACCGC GACGGTGAAA AAGAATGGGG TAGCTCAGGC
1981 TAATGTCCCT GTTTCATTTA ATATTGTTTC AGGAACTGCA ACTCTTGGGG CAAATAGTGC
2041 CAAAACGGAT GCTAACGGTA AGGCAACCGT AACGTTGAAG TCGAGTACGC CAGGACAGGT
2101 CGTCGTGTCT GCTAAAACCG CGGAGATGAC TTCAGCACTT AATGCCAGTG CGGTTATATT
2161 TTTTGATCAA ACCAAGGCCA GCATTACTGA GATTAAGGCT GATAAGACAA CTGCAGTAGC
2221 AAATGGTAAG GATGCTATTA AATATACTGT AAAAGTTATG AAAAACGGTC AGCCAGTTAA
2281 TAATCAATCC GTTACATTCT CAACAAACTT TGGGATGTTC AACGGTAAGT CTCAAACGCA
2341 AGCAACCACG GGAAATGATG GTCGTGCGAC GATAACACTA ACTTCCAGTT CCGCCGGTAA
2401 AGCGACTGTT AGTGCGACAG TCAGTGATGG GGCTGAGGTT AAAGCGACTG AGGTCACTTT
2461 TTTTGATGAA CTGAAAATTG ACAACAAGGT TGATATTATT GGTAACAATG TCAAGAGGTC
2521 GATGTTGCCT AATATTTGGC TGCAATATGG TCAGTTTAAA CTGAAAGCAA GCGGTGGTGA
2581 TGGTACATAT TCATGGTATT CAGAAAATAC CAGTATCGCG ACTGTCGATG CATCAGGGAA
2641 AGTCACTTTG AATGGTAAAG GCAGTGTCGT AATTAAAGCC ACATCTGGTG ATAAGCAAAC
2701 AGTAAGTTAC ACTATAAAAG CACCGTCGTA TATGATAAAA GTGGATAAGC AAGCCTATTA
2761 TGCTGATGCT ATGTCCATTT GCAAAATTT ATTACCATCC ACACAGACGG TATTGTCAGA
2821 TATTTATGAC TCATGGGGGG CTGCAAATAA ATATAGCCAT TATAGTTCTA TGAACTCAAT
2881 AACTGCTTGG ATTAAACAGA CATCTAGTGA GCAGCGTTCT GGAGTATCAA GCACTTATAA
2941 CCTAATAACA CAAAACCCTC TTCCTGGGGT TAATGTTAAT ACTCCAAATG TCTATGCGGT
3001 TTGTGTAGAA TAATTCCATA ACCACCCCGG CTAAAATATG TATTGTTTTA GTCGGGGCAT
3061 AATTATTTCT TCTTAAGAAA TAACCCTCTT ATAATCAAAT CTACTACTGG TCTTTTTATC
3121 TGCTTAATAG G SEQ ID NO:20
```

FIG. 3

```
   1 GGAAAGATAA ATCCGATCTA TTAATATAAT TTATTTCTCA TTCTAACTCA TTGTGGTGGA
  61 GCCATAACAT GAGTACTCAT GGTTGTTATA CCCGGACCCG GCACAAGCAT AAGCTAAAAA
 121 AAACATTGAT TATGCTTAGT GCTGGTTTAG GATTGTTTTT TTATGTTAAT CAGAATTCAT
 181 TTGCAAATGG TGAAAATTAT TTTAAATTGG GTTCGGATTC AAAACTGTTA ACTCATGATA
 241 GCTATCAGAA TCGCCTTTTT TATACGTTGA AAACTGGTGA AACTGTTGCC GATCTTTCTA
 301 AATCGCAAGA TATTAATTTA TCGACGATTT GGTCGTTGAA TAAGCATTTA TACAGTTCTG
 361 AAAGCGAAAT GATGAAGGCC GCGCCTGGTC AGCAGATCAT TTTGCCACTC AAAAAACTTC
 421 CCTTTGAATA CAGTGCACTA CCACTTTTAG GTTCGGCACC TCTTGTTGCT GCAGGTGGTG
 481 TTGCTGGTCA CACGAATAAA CTGACTAAAA TGTCCCCGGA CGTGACCAAA AGCAACATGA
 541 CCGATGACAA GGCATTAAAT TATGCGGCAC AACAGGCGGC GAGTCTCGGT AGCCAGCTTC
 601 AGTCGCGATC TCTGAACGGC GATTACGCGA AGATACCGC TCTTGGTATC GCTGGTAACC
 661 AGGCTTCGTC ACAGTTGCAG GCCTGGTTAC AACATTATGG AACGGCAGAG GTTAATCTGC
 721 AGAGTGGTGA TAACTTTGAC GGTAGTTCAC TGGACTTCTT ATTACCGTTC TATGATTCCG
 781 AAAAAATGCT GGCATTTGGT CAGGTCGGAG CGCGTTACAT TGACTCCCGC TTTACGGCAA
 841 ATTTAGGTGC GGGTCAGCGT TTTTTCCTTC CTGCAAACAT GTTGGGCTAT AACGTCTTCA
 901 TTGATCAGGA TTTTTCTGGT GATAATACCC GTTTAGGTAT TGGTGGCGAA TACTGGCGAG
 961 ACTATTTCAA AAGTAGCGTT AACGGCTATT TCCGCATGAG CGCTGGCAT GAGTCATACC
1021 ATAAGAAAGA CTATGATGAG CGCCCAGCAA ATGGCTTCGA TATCCGTTTT AATGGCTATC
1081 TACCGTCATA TCCGGCATTA GGCGCCAAGC TGATATATGA GCAGTATTAT GGTGATAATG
1141 TTGCTTTGTT TAATTCTGAT AAGCTGCAGT CGAATCCTGG TGCGGCGACC GTTGGTGTAA
1201 ACTATACTCC GATTCCTCTG GTGACGATGG GGATCGATTA CCGTCATGGT ACGGGTAATG
1261 AAAATGATCT CCTTTACTCA ATGCAGTTCC GTTATCAGTT TGATAAATCG TGGTCTCAGC
1321 AAATTGAACC ACAGTATGTT AACGAGTTAA GAACATTATC AGGCAGCCGT TACGATCTGG
1381 TTCAGCGTAA TAACAATATT ATTCTGGAGT ACAAGAAGCA GGATATTCTT TCTCTGAATA
1441 TTCCGCATGA TATTAATGGT ACTGAACACA GTACGCAGAA GATTCAGTTG ATCGTTAAGA
1501 GCAAATACGG TCTGGATCGT ATCGTCTGGG ATGATAGTGC ATTACGCAGT CAGGGCGGTC
1561 AGATTCAGCA TAGCGGAAGC CAAAGCGCAC AAGACTACCA GGCTATTTTG CCTGCTTATG
1621 TGCAAGGTGG CAGCAATATT TATAAAGTGA CGGCTCGCGC CTATGACCGT AATGGCAATA
1681 GCTCTAACAA TGTACAGCTT ACTATTACCG TTCTGTCGAA TGGTCAAGTT GTCGACCAGG
1741 TTGGGGTAAC GGACTTTACG GCGGATAAGA CTTCGGCTAA AGCGGATAAC GCCGATACCA
1801 TTACTTATAC CGCGACGGTG AAAAAGAATG GGGTAGCTCA GGCTAATGTC CCTGTTTCAT
1861 TTAATATTGT TTCAGGAACT GCAACTCTTG GGGCAAATAG TGCCAAAACG GATGCTAACG
1921 GTAAGGCAAC CGTAACGTTG AAGTCGAGTA CGCCAGGACA GGTCGTCGTG TCTGCTAAAA
1981 CCGCGGAGAT GAGTTCAGCA CTTAATGCCA GTGCGGTTAT ATTTTTGAT CAAACCAAGG
2041 CCAGCATTAC TGAGATTAAG GCTGATAAGA CAACTGCAGT AGCAAATGGT AAGGATGCTA
2101 TTAAATATAC TGTAAAAGTT ATGAAAAACG GTCAGCCAGT TAATAATCAA TCCGTTACAT
2161 TCTCAACAAA CTTTGGGATG TTCAACGGTA AGTCTCAAAC GCAAGCAACC ACGGGAAATG
2221 ATGGTCGTGC GACGATAACA CTAACTTCCA GTTCCGCCGG TAAAGCGACT GTTAGTGCGA
2281 CAGTCAGTGA TGGGGCTGAG GTTAAAGCGA CTGAGGTCAC TTTTTTTGAT GAACTGAAAA
2341 TTGACAACAA GGTTGATATT ATTGGTAACA ATGTCAGAGG CGAGTTGCCT AATATTTGGC
2401 TGCAATATGG TCAGTTTAAA CTGAAAGCAA GCGGTGGTGA TGGTACATAT TCATGGTATT
2461 CAGAAAATAC CAGTATCGCG ACTGTCGATG CATCAGGGAA AGTCACTTTG AATGGTAAAG
2521 GCAGTGTCGT AATTAAAGCC ACATCTGGTG ATAAGCAAAC AGTAAGTTAC ACTATAAAAG
2581 CACCGTCGTA TATGATAAAA GTGGATAAGC AAGCCTATTA TGCTGATGCT ATGTCCATTT
2641 GCAAAAATTT ATTACCATCC ACACAGACGG TATTGTCAGA TATTTATGAC TCATGGGGGG
2701 CTGCAAATAA ATATAGCCAT TATAGTTCTA TGAACTCAAT AACTGCTTGG ATTAAACAGA
2761 CATCTAGTGA GCAGCGTTCT GGAGTATCAA GCACTTATAA CCTAATAACA CAAAACCCTC
2821 TTCCTGGGGT TAATGTTAAT ACTCCAAATG TCTATGCGGT TTGTGTAGAA TAATTCCATA
2881 ACCACCCCGG CTAAAATATG TATTGTTTTA GTCGGGGCAT AATTATTTCT TCTTAAGAAA
2941 TAACCTCTTA TAATCAAATC TACTACTGGT CTTTTTATCT GCTTAATAGG TCTCTTTCAA
3001 AGAGACACAT TCACGTTTTC TAGAGTAGGT TGATCCAACC ACGCTGTATA CCAAAGCTGA
3061 ATCACATCAA GCAACAACTA TGCTCACAAC ATCCACACAA TAAAAA SEQ ID NO:21
```

*FIG. 4*

METHOD OF STIMULATING AN IMMUNE RESPONSE BY ADMINISTRATION OF HOST ORGANISMS THAT EXPRESS INTIMIN ALONE OR AS A FUSION PROTEIN WITH ONE OR MORE OTHER ANTIGENS

CROSS-REFERENCE TO RELATED APPLICATION

This application is related to provisional applications entitled HISTIDINE-TAGGED INTIMIN AND METHODS OF USING INTIMIN TO STIMULATE AN IMMUNE RESPONSE AND AS AN ANTIGEN CARRIER WITH TARGETING CAPABILITY, of inventors Marian McKee, Alison O'Brien, and Marian Wachtel, Provisional Application No. 60/015,657, filed on Apr. 19, 1996, and Provisional Application No. 60/015,938, filed on Apr. 22, 1996; said applications are incorporated herein by reference.

GOVERNMENT INTEREST

The invention described herein may be manufactured, licensed and used for governmental purposes without the payment of any royalties to us thereon.

FIELD OF THE INVENTION

This invention relates to a plasmid for engineering plants to express intimin, alone or as a fusion protein with one or more antigens, and to a method of promoting a protective immune response by the administration of host organisms transformed with such plasmids. Such protective immune response will be directed to intimin, or portions thereof and/or to the one or more antigens. The host organisms include bacteria, yeast, fungus, and plants.

BACKGROUND OF THE INVENTION

A virulent form of bloody diarrhea is caused by the Enterohemorrhagic *Escherichia coli* (EHEC). This pathogen is the most common infectious cause of bloody diarrhea (also called hemorrhagic colitis [HC]) in the United States (Centers for Disease Control and Prevention (executive summary). MMWR 43(No.RR-5):1–18 (1994); Griffin, P. M. et al. Annals of Internal Med. 109:705 (1988)). One serotype in particular, 0157:H7, is the most commonly isolated serotype of EHEC in the United States, and has been linked to a significant number of outbreaks of HC beginning in 1982 (Riley, L. W. et al. N.Eng.J. Med. 308:681 (1983)).

The primary mode of transmission of EHEC occurs through ingestion of contaminated food, particularly undercooked hamburger (Doyle, M. P. and Schoeni, J. L. Appl. Environ. Microbiol. 53:2394 (1987); Samadpour, M. et al. Appl. Environ. Microbiol. 60:1038 (1994)). Among people infected by EHEC, as many as 5% suffer a serious complication called Hemolytic Uremic Syndrome (HUS), a condition caused by the action of Shiga-like toxins that target and destroy cells lining blood vessels (endothelial cells), such as those present in the glomeruli of the kidney. (Johnson, W. M. et al. Lancet. i:76 (1983); O'Brien, A. D. et al. Lancet. i:702 (1983)). HUS can result in permanent kidney damage or even complete kidney failure.

Although EHEC can cause very serious illness even in healthy adults, young children in particular are at greater risk of dying or suffering permanent damage from the infection. Others for whom the infection can be particularly dangerous include the elderly and the immuno-compromised. With the prevalence of EHEC in cattle and the subjective nature of differentiating between cooked and undercooked hamburger, a convenient stop at a fast food restaurant, or even a family barbecue, can result in family tragedy.

One key to the deadly nature of EHEC is the bacteria's ability to produce attaching/effacing (A/E) intestinal lesions in the colon, such as those demonstrated in gnotobiotic pigs (Tzipori, S. et al. Infect. Immun. 57:1142 (1989)). The A/E lesions demonstrated in pigs are characterized by intimate bacterial adherence to the mucosal cells of the intestinal lining and dissolution of microvilli (McKee, M. L. et al. Infect. Immun. 63:3739 (1995); Tzipori, S. et al. Infect. Immun. 57:1142 (1989)). Similar lesions have been seen in human laryngeal epithelial (HEp-2)(ATCC # CCL23) cells in tissue culture (McKee, M. L. et al. Infect. Immun. 63:3739 (1995); Tzipori, S. et al. Infect. Immun. 57:1142 (1989)).

In 1990, Jerse et al. identified a chromosomal gene in a related diarrheagenic *E. coli* strain, Enteropathogenic *E. coli* (EPEC). That gene, designated eae, was found to be required for the bacterium to produce A/E lesions in tissue culture (Jerse, A. E. et al. Proc. Natl. Acad. Sci. USA. 87:7839 (1990)). The eae gene encoded a 94 kDa outer membrane protein, called Eae, which is the intimin of EPEC. A similar protein was demonstrated to be present in an EHEC 0157:H7 strain (Jerse, A. E. and Kaper, J. B. Infect. Immun. 59:4302 (1991)).

Recently, investigators demonstrated that intimin is necessary for adherence of EHEC to human epithelial laryngeal (HEp-2) cells and human ileocecal epithelial (HCT-8) cells (ATCC # CCL244) (McKee, M. L. et al. Infect. Immun. 63:3739 (1995)) and for formation of A/E lesions in the piglet intestine (Donnenberg, M. S. et al. J. Clin. Invest. 92:1418 (1993); McKee, M. L. et al. Infect. Immun. 63:3739 (1995)). Although human studies with EHEC have not been conducted, the intimin protein found in EPEC is strongly associated with the production of diarrhea and fever in human volunteers (Donnenberg, M. S. et al. J. Clin. Invest. 92:1412 (1993); Levine, M. M. et al. J. Infect. Dis. 152:550 (1985)).

Human volunteers (10 out of 10) challenged with EPEC strain E2348/69 mounted a notable immune response to the 94 kDa protein after 28 days (Levine et al. J Infect. Dis. 152:550, 1985)). In these human trials the only volunteer (1 out of 10) who failed to develop diarrhea after ingestion of E2348/69 was the individual in this group who had detectable antibody to the 94 kDa protein before challenge.

Two other bacterial species capable of inducing A/E lesions have been shown to contain the eae locus: *Hafnia alvei* (Albert, M. J. et al. J. Med. Microbiol. 37:310 (1992)) and *Citrobacter freundii* biotype 4280 (Schauer, D. B., and Falkow, S. Infect. Immun. 61:2486 (1993)). Although these bacteria are not generally associated with pathology in humans, they can cause significant disease in the animal species with which they are normally associated. For instance, *Citrobacter freundii* biotype 4280 is associated with gastrointestinal illness in mice. Mice often serve as control and test subjects in experiments. Costly and carefully controlled experiments can be jeopardized by an outbreak of this disease in an animal care facility. In addition, such bacterial species may become pathogenic to immunocompromised patients, the young and the elderly.

Animals, such as cows, infected with bacterial strains expressing intimin may become ill themselves, in addition to serving as a source of such infections to others. Eradicating or even limiting these animal reservoirs of intimin-expressing bacteria in animals with antibiotic therapy would be prohibitively expensive. In addition, not only is antibiotic treatment of the infections in humans or animals costly, but the antibiotics themselves are associated with side effects that can be dangerous. As with EHEC, those side effects can be especially dangerous to young children and the elderly. Consequently, the need exists for another means of reducing the seriousness of the infections or preventing them altogether through promotion of protective immune responses against bacteria expressing intimin.

A further need is for forms of immunization that are less time consuming, expensive and painful than immunization through injection of antigens. Yet another need is for the generation of protective immune responses in the specific tissues involved at the point of infection, most often the gastrointestinal mucosa.

Other organisms infecting gastrointestinal tissue, including, but not limited to Salmonella sp. and Shigella sp., possess antigens against which an immune response could be generated. A need exists, however, for a means of targeting those antigens to gastrointestinal mucosa, in order to stimulate a mucosal immune response, as well as stimulating circulating antibodies.

Finally, a need exists for alternate means of delivering agents that promote a protective immune response.

SUMMARY OF THE INVENTION

The present invention relates to a method of stimulating an immune response comprising transforming a plant with a vector encoding intimin, an intimin-like protein, or a portion thereof, wherein the plant expresses an intimin, an intimin-like protein, or a portion thereof, and administering the plant, or a portion thereof, to a patient. The present invention also relates to a method of stimulating an immune response comprising transforming a plant with a vector encoding intimin, an intimin-like protein, or a portion thereof, wherein said plant expresses an intimin, an intimin-like protein, or a portion thereof, extracting intimin, a portion of intimin, or an intimin-like protein from the plant or portion thereof, administering the extracted intimin, portion of intimin, or an intimin-like protein to a patient.

The invention additionally relates to a DNA construct that codes for the expression of a heterologous DNA in a plant, wherein the heterologous DNA encodes intimin, intimin-like protein, or a portion thereof. The invention further relates to a plant cell containing a heterologous DNA construct that encodes and expresses a heterologous DNA, wherein the heterologous DNA encodes intimin, intimin-like protein, or a portion thereof.

The present invention still further relates to a method of making transgenic plant cells, comprising providing a plant cell capable of regeneration, and transforming the plant cell with a DNA construct as described above.

BRIEF DESCRIPTION OF THE DRAWINGS

FIG. 2 depicts the predicted protein sequence of the complete EHEC 933 eae gene.

FIG. 3 depicts the DNA sequence from EHEC strain CL8, sequenced by Beebakhee, G. et al.

FIG. 4 depicts the DNA sequence from EHEC strain 933, sequenced by Yu and Kaper.

FIG. 7 depicts pEB310, a plasmid encoding EHEC strain 86-24 eae (entire coding sequence) driven by the PT7 promoter.

FIG. 8 depicts histidine-tag expression plasmids (Qiagen Inc.).

FIG. 9 depicts the repressor plasmid (Qiagen Inc.). The black box marked "6XHis" corresponds to the sequence CAY CAY CAY CAY CAY CAY which encodes 6 histidine residues. (multicopy).

FIG. 10 depicts pEB312, a plasmid encoding RVHindHis. This plasmid encodes a histidine-tagged intimin that spans 604 of 935 predicted amino acids.

FIG. 11 depicts the different fragments of eae cloned into his-tagged vectors, and the corresponding names of these plasmids.

FIG. 12 depicts the different C-terminal fragments of eae cloned into his-tagged vectors and the corresponding names of these plasmid.

FIG. 13 depicts the construction of an eae mutant, 86-24 eaeΔ10, by allelic exchange.

FIG. 14 depicts pEB290, a plasmid encoding most of the eae structural gene. The 3' 250 bp of eae are not encoded by pEB290.

FIG. 15 depicts pEB300, used to construct the deletion mutant; deleted for the 1275 bp internal Bcl I fragment of eae.

FIG. 16 depicts pAM450, a suicide vector for introduction of cloned genes into the bacterial chromosome.

FIG. 17 depicts pEB305, a plasmid encoding the deleted eae gene in pAM450 vector for homologous recombination.

FIG. 18 depicts the cloning scheme for construction of a plasmid expressing N-His-IcsA-intimin-C.

FIG. 19 shows the cloning scheme for construction of a plasmid designed to engineer plants to express his-intimin. The plant expression vector pKLYX 71 $S^2$ and the his-intimin encoding plasmid pINT are also depicted.

FIG. 20 shows the cloning scheme for construction of a plasmid designed to engineer bacterial hosts to express his-intimin.

FIG. 21 depicts pGHNC5, a plasmid containing a plant expression cassette. The MARs are tobacco nuclear scaffold attachment regions. The ClaI-EcoRI fragment containing 3'-rbcs-eae-His-$35S^2$ is excised from pINT and ligated into pGHNC5 to create pMAREAE, depicted in FIG. 22.

FIG. 22 depicts the plasmid pMAREAE. The SacI-KpnI fragment containing MAR-$35s^2$-His-eae-3'rbcs-MAR is excised from pMAREAE and ligated into pBIN19 to create pBIN-ME, depicted in FIG. 23. The plasmid pBIN19 encodes the NPTII gene (nopaline synthase from *Agrebacterium tumefaciens*, conferring kanamycin resistance). NPTII is flanked by a nopaline synthase promoter (pNOS), as well as a nopaline synthase terminator (3'NOS ).

FIG. 23 depicts pBIN-ME, a plasmid containing MAR-$35S^2$-His-eae-3'rbcs-MAR. This plasmid has kanamycin resistance conferred by the 3'NOS-NPTII-pNOS cassette.

DETAILED DESCRIPTION OF THE INVENTION

The present invention relates to a method of stimulating an immune response comprising transforming a plant with a vector encoding intimin, an intimin-like protein, or a portion thereof, wherein the plant expresses an intimin, an intimin-like protein, or a portion thereof, and administering the plant, or a portion thereof, to a patient. The invention further relates to such methods where the intimin, intimin-like protein, or portion thereof additionally comprises at least one antigen, at least one drug, or a combination thereof, recombinatorially fused to the intimin, intimin-like protein, or portion thereof.

Figure 1:
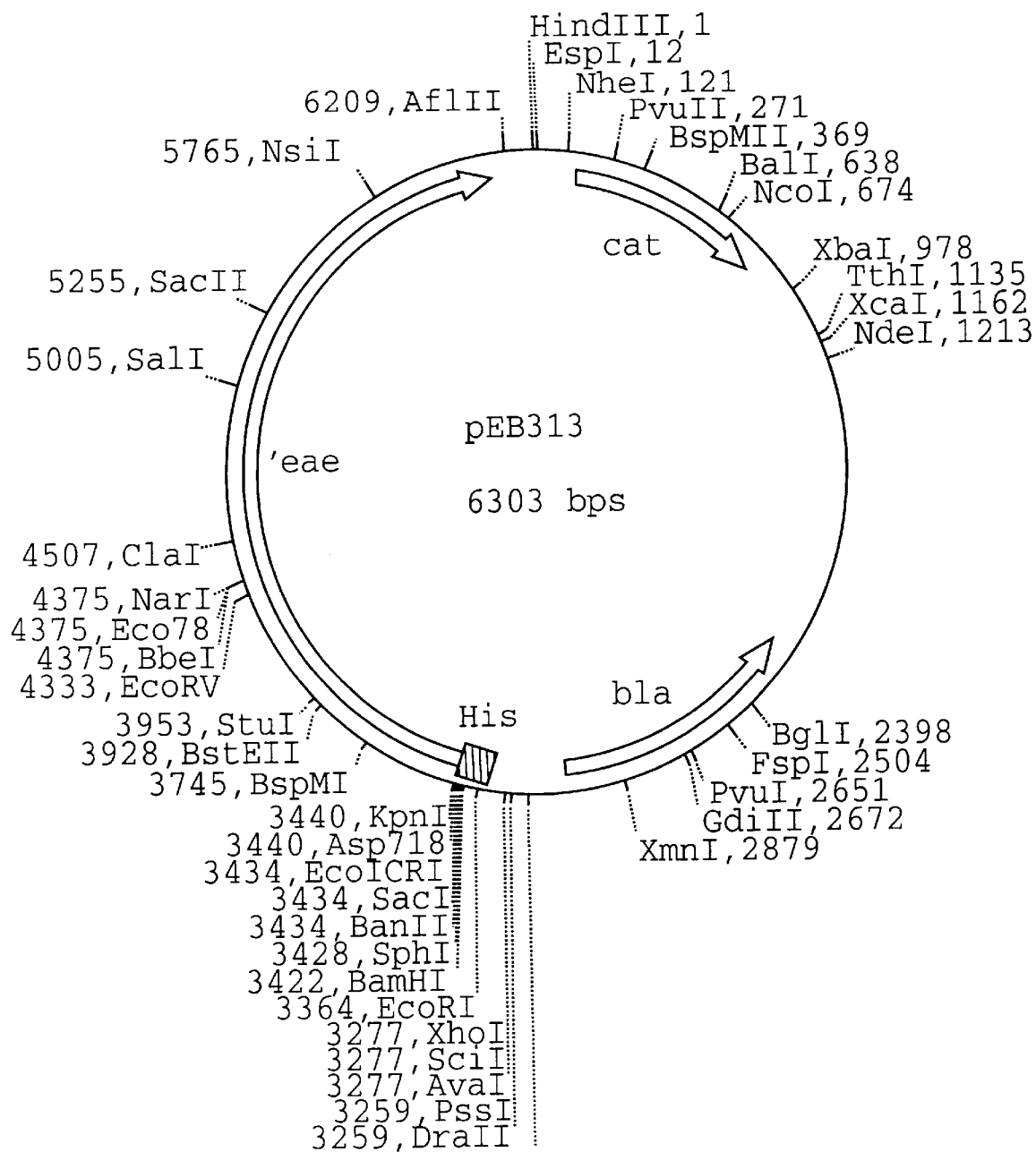
FIG. 1 depicts pEB313, a plasmid encoding RIHisEae. This plasmid encodes a histidine-tagged intimin that spans 900 out of 935 predicted amino acids.
Figure 5:
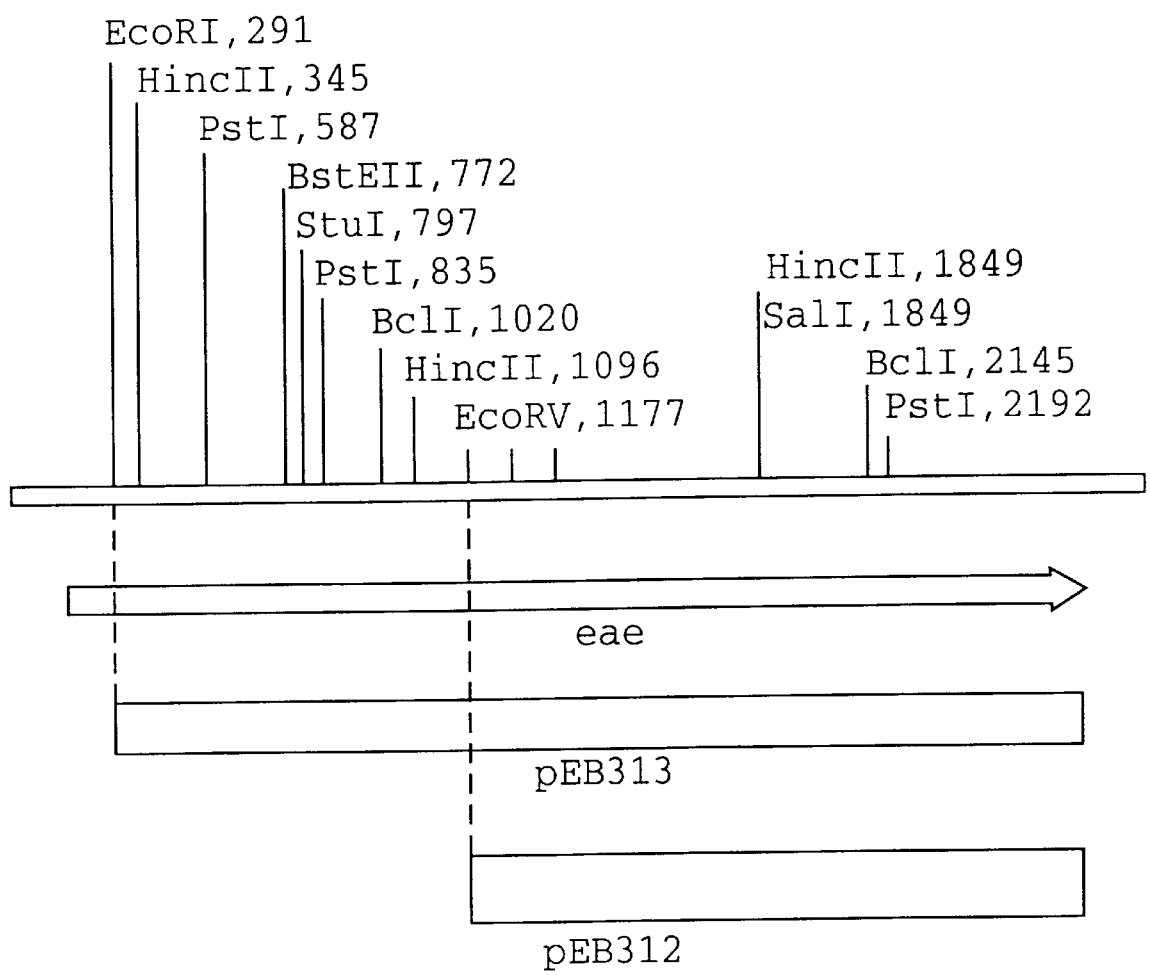
FIG. 5 depicts the 3144 bp fragment of eae produced by PCR amplification, in the region labelled eae.
Figure 6:
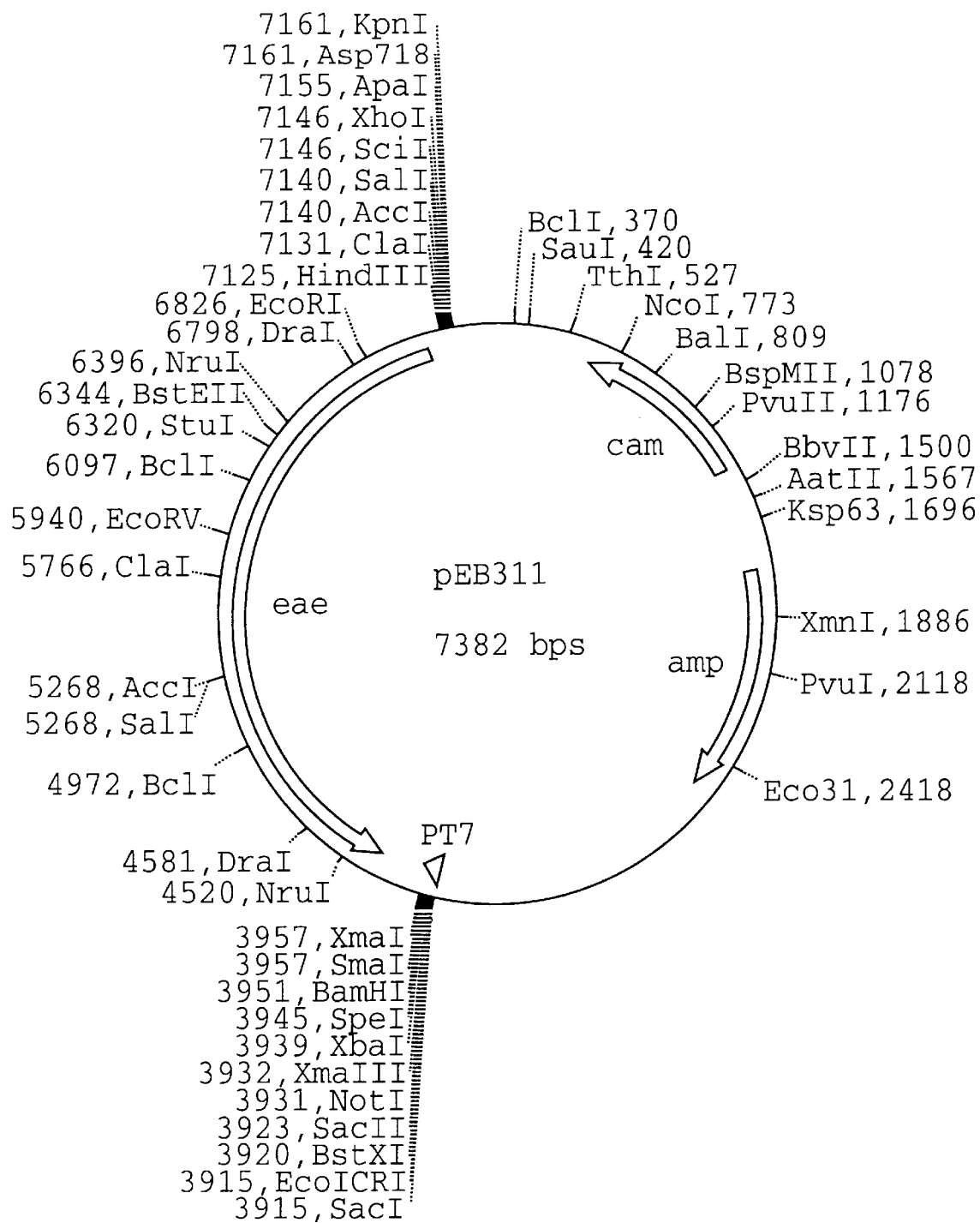
FIG. 6 depicts pEB311, a plasmid encoding EHEC strain 86-24 eae (entire coding sequence) driven by the lac promoter.
Figure 7:
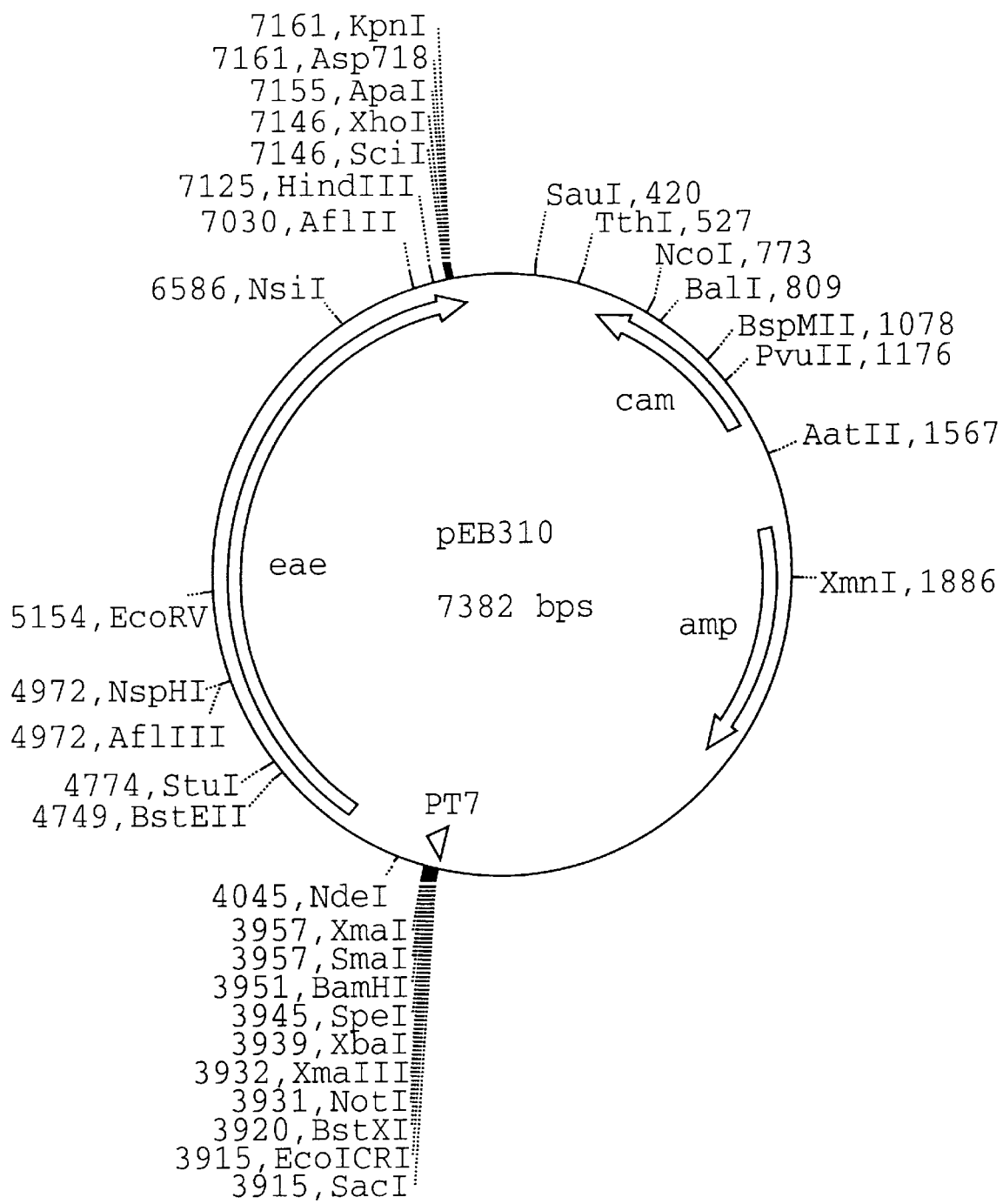
Figure 8:
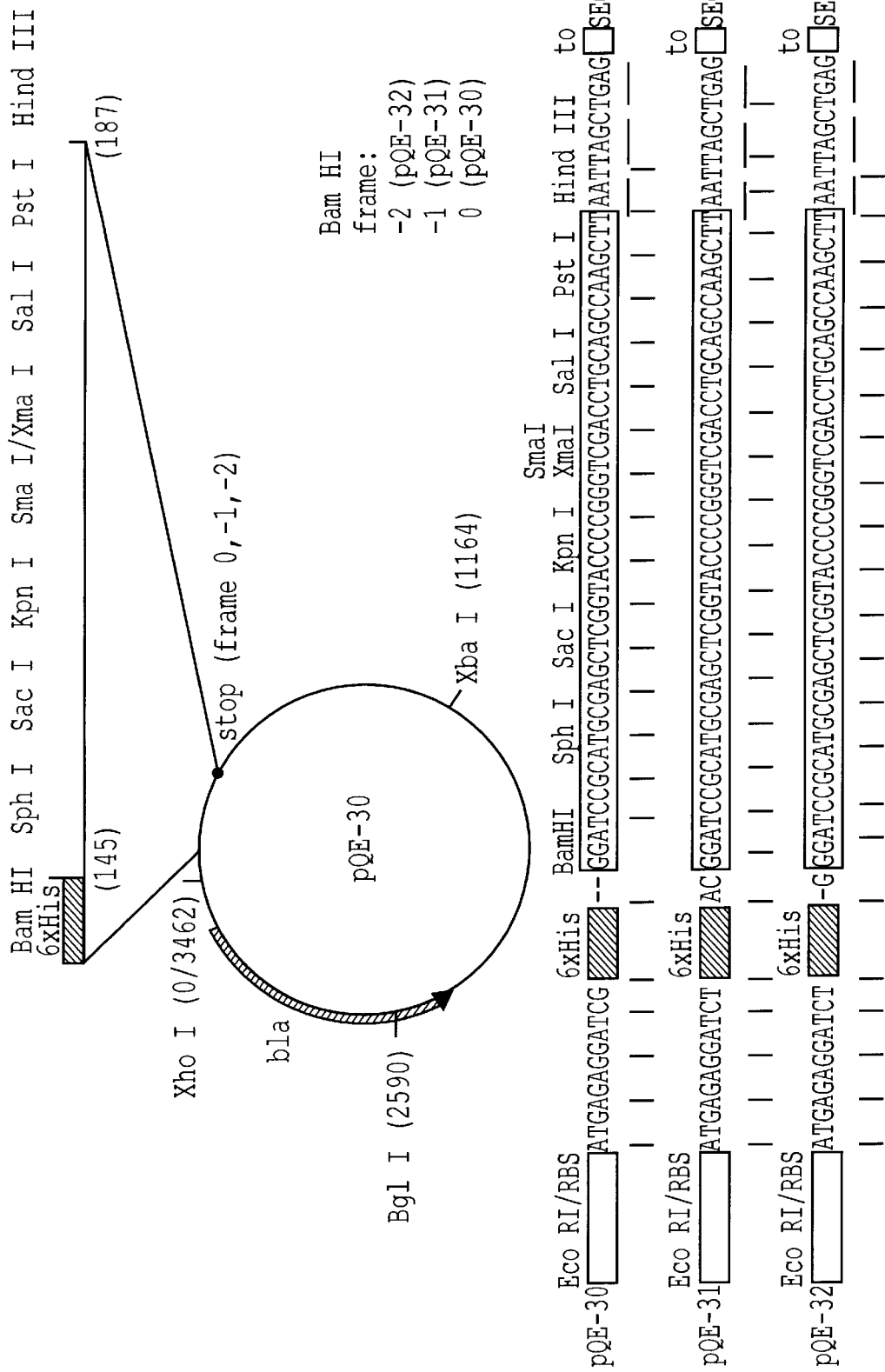
Figure 9:
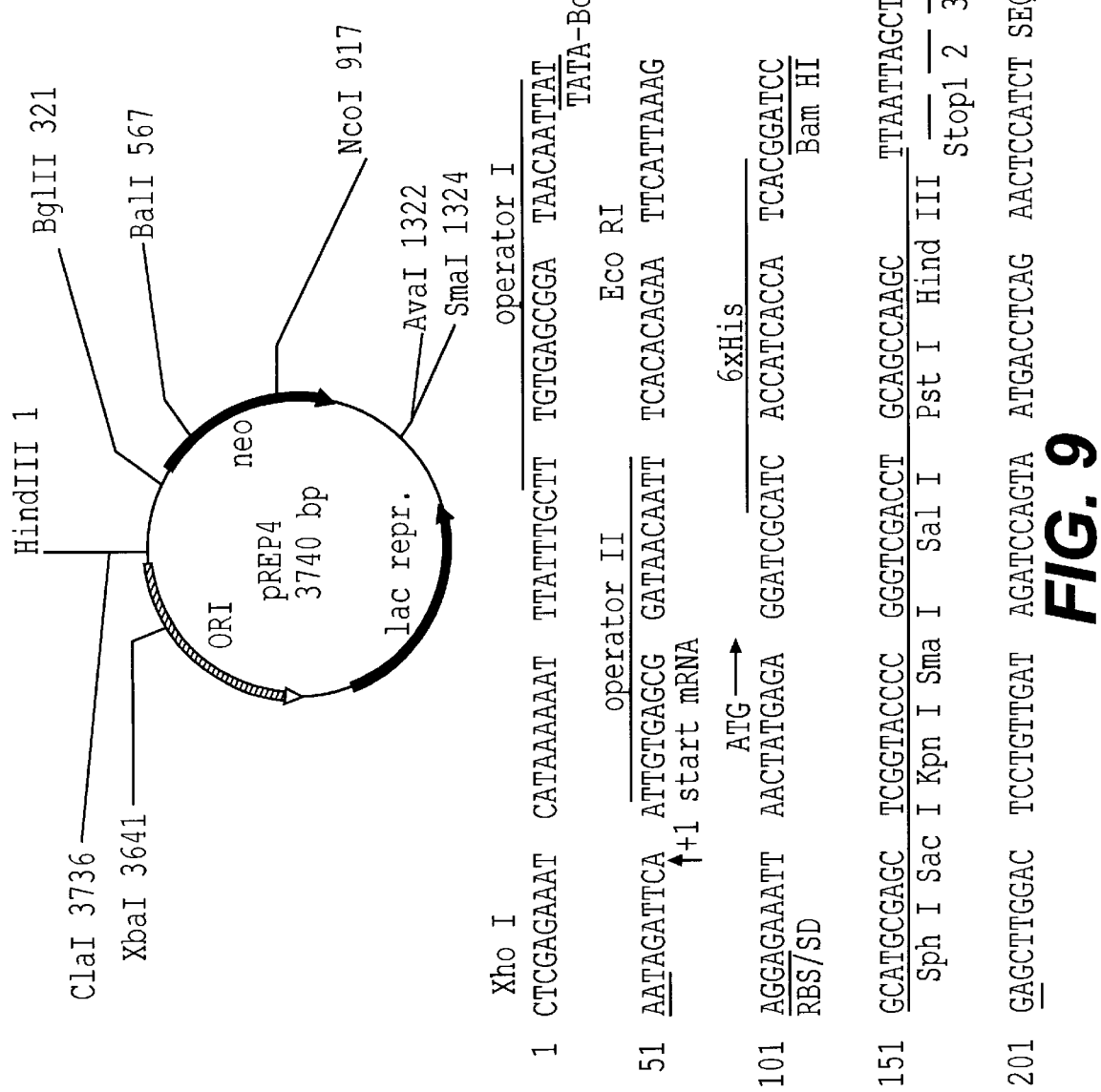
Figure 10:
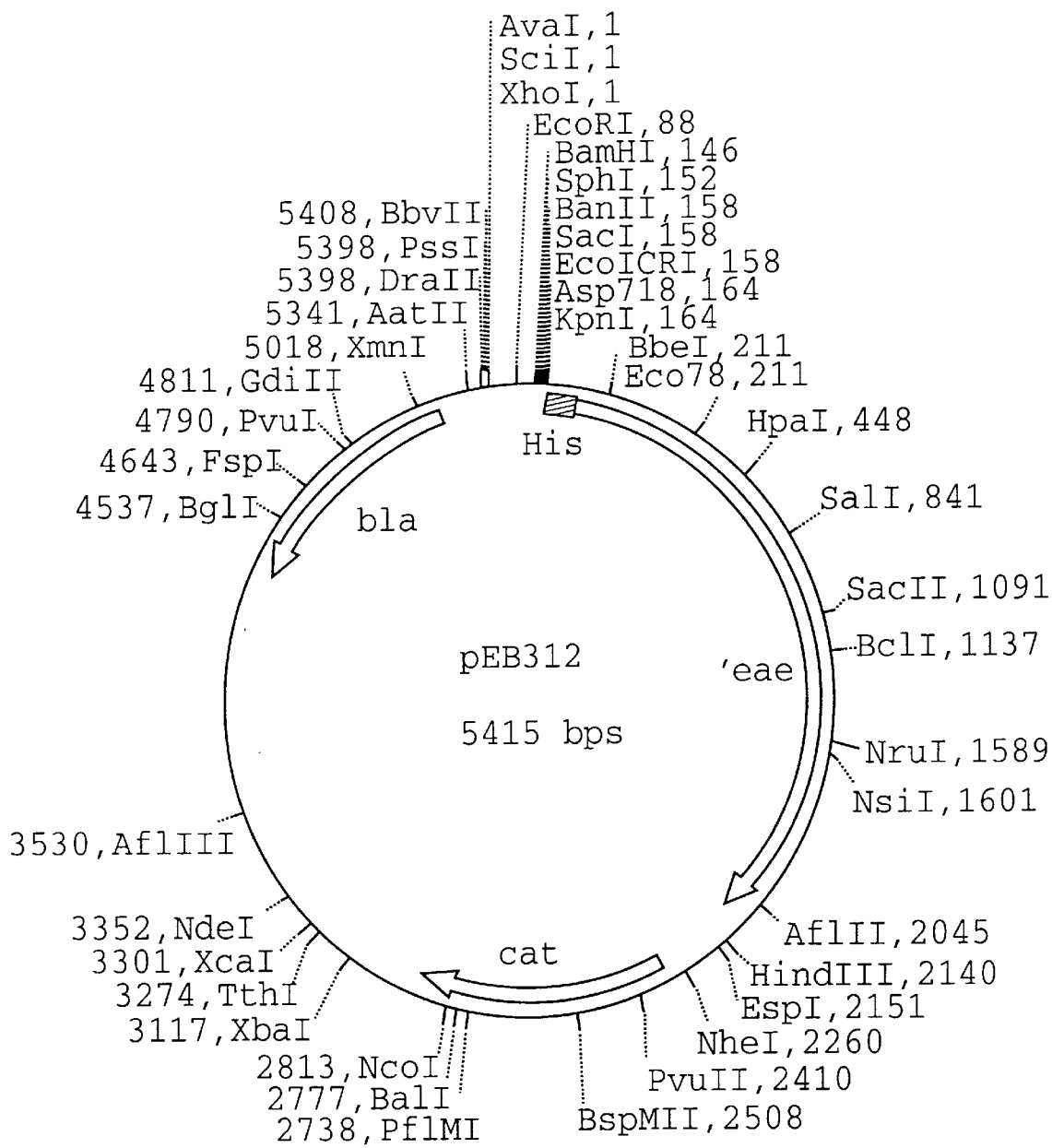

The invention further relates to a method of stimulating an immune response comprising transforming a plant with a vector encoding intimin, an intimin-like protein, or a portion thereof, wherein the plant expresses an intimin, an intimin-like protein, or a portion thereof, extracting intimin, a portion of intimin, or an intimin-like protein from the plant or portion thereof, and administering the extracted intimin, portion of intimin, or intimin-like protein to a patient. This invention also relates to this method where the intimin, intimin-like protein, or portion thereof additionally comprises at least one antigen, at least one drug, or a combination thereof, recombinatorially fused to the intimin, intimin-like protein, or portion thereof.

The methods described above can also include the step of enriching the intimin, portion of intimin, or intimin-like protein prior to administration or purifying the intimin, portion of intimin, or intimin-like protein prior to administration. Preferably in the above-described methods, the intimin is EHEC intimin. It is also preferred that the intimin, intimin-like protein, or portion thereof further comprises a histidine tag.

In the above-described methods, the plant can be monocotyledonous or dicotyledonous. Examples of such plants are described in more detail below, but more preferably include alfalfa, carrot, canola, tobacco, banana, and potato plants.

The present invention also relates to a DNA construct that codes for the expression of a heterologous DNA in a plant, wherein the heterologous DNA encodes intimin, intimin-like protein, or portion thereof. The heterologous DNA additionally can also code at least one antigen, at least one drug, or a combination thereof, recombinatorially fused to the intimin, intimin-like protein, or portion thereof.

Preferably the DNA construct is a plant transformation vector. The plant transformation vector is preferably Agrobacterium vector. It is also preferred that the plant transformation is conducted via a microparticle. It is additionally preferred that the plant transformation vector is a viral vector.

In the above-described DNA constructs according to the invention, preferably the intimin, intimin-like protein, or portion therof encoded by said DNA further comprises a histidine tag. It is also preferred that the codons of the heterologous DNA are replaced with codons that are preferred for expression in a plant cell.

The present invention is still further directed to a plant cell containing a heterologous DNA construct that encodes and expresses a heterologous DNA, wherein the heterologous DNA encodes intimin, intimin-like protein, or a portion thereof. In such plant cells, the heterologous DNA can additionally encode at least one antigen, at least one drug, or a combination thereof, recombinatorially fused to the intimin, intimin-like protein, or portion thereof. Preferably in these plant cells the intimin, intimin-like protein, or portion thereof encoded by the DNA further comprises a histidine tag.

The present invention still further yet relates to a method of making transgenic plant cells, comprising providing a plant cell capable of regeneration, and transforming the plant cell with a DNA construct as described above. Preferably the transforming step of this method is carried out by infecting the plant cell with an Agrobacterium vector that transfers the DNA construct into the plant cell. It is also preferred that the transforming step is carried out by bombarding the plant cell with microparticles carrying the DNA construct. Additionally, it is preferred that the transforming step is carried out by transformation with a viral vector, Preferably for the above-described methods, the plant cell resides in a plant tissue capable of regeneration. The above-described method can also comprise the step of regenerating shoots, roots, or a plant from the transformed plant cells. In this method, the plant preferably is monocotyledonous or dicotyledonous. It is also preferred that, for this method, the intimin, intimin-like protein, or portion thereof encoded by the DNA further comprises a histidine tag.

An object of the invention is to express intimin in a host organism, which host will be administered or fed, directly or after processing, to animals or humans in order to stimulate an immune response to intimin. Such an immune response will protect the animal or human against illness, disease and related sequelae caused by EHEC and other pathogens having the capacity to bind epithelial cells through proteins having some degree of homology with the specific intimin expressed by EHEC.

The object is achieved through stimulation of an immune response directed against intimin, thereby blocking the capability of EHEC to adhere to epithelial cells. Consequently, the term immunization is used in the application. The degree of protection will vary with the degree of homology with intimin as well as the unique attributes of the patient, particularly as different species will be treated. The precise degree of protection is unimportant to quantitate in practicing the invention for any particular pathogen. In addition, the invention describes the expression of intimin in a host organism as a fusion protein with one or more other antigens and administration of host organism to promote a protective immune response against intimin and the one or more antigens.

In addition to stimulating an immune response that permits a patient to avoid infection altogether, immunization as used herein also means decreasing the ability of the pathogens to colonize the gastrointestinal tract and decreasing the severity of an infection, as measured by any of the following indicators: reduced incidences of death, HUS, or permanent kidney damage; decreased levels of toxins; reduced fluid loss; or other indicators of illness regularly used by those ordinarily skilled in the relevant art. Thus, an immunoprotective amount is that amount sufficient to decrease the ability of the pathogens to colonize the gastrointestinal tract as well as decreasing the severity of an infection as measured by the above indicators.

A preferred host of the invention is a plant cell.

Plant cells have successfully been engineered to express heterologous genes, such as those of bacterial origin. Crop plants of all types have been engineered with genes from bacterial origin. Some examples of these are the commonly-used antibiotic resistance genes, such as the scorable marker genes for neomycin phosphotransferase (NPTII) and hygromycin phosphotransferase (HPII). These genes were isolated from the bacterium *E. coli* (Fraley, R. T., et al., Proc. Natl. Acad. Sci. USA 80: 4803 (1983); Vandenberghe et al., Plant Mol. Biol. 5: 299 (1985)). Another popular scorable marker gene routinely used in plant transformation studies also comes from *E. coli*: beta glucuronidase (GUS) (Jefferson Plant Mol. Biol. Rep. 5: 387–405 (1988)). All of these genes have been useful and have been highly expressed by transgenic plants, i.e., those containing heterologous DNA, in their native form; they required no modifications in their coding sequence.

Other genes from bacteria, however, have been poorly expressed when engineered into plants. One example is the mercuric ion reductase gene from *E. coli* (Wilde et al., Mecuric ion reduction and resistance in transgenic *Arabidopsis thaliana* plants expressing a modified bacterial merA gene. Proc. Natl. Acad. Sci. USA in press). It required modification in its coding sequence before it could be expressed. Perhaps the best-known example are insecticidal cry genes from *Bacillus thuringiesis*. They have all exhibited low to no expression until they were "rebuilt" or codon optimized for expression in plants (Perlak et al., Proc. Natl. Acad. Sci. USA 88: 3324–3328 (1991); Adang et al., Plant Mol. Biol. 21: 1131–1145 (1993)). In these studies, researchers reconstructed the genes by synthesizing and linking oligonucleotides that encode preferential codons for the plant species, without changing the amino acid sequence. By matching the codon usage of the new gene to plant-preferred codons, the introduced gene can be highly expressed (e.g., Stewart et al., Insect control and dosage effects in transgenic canola, *Brassica napus* L. (Brassicaceae), containing a synthetic *Bacillus thuringiensis* CryIa(c) gene. Plant Physiology, 112:115–120 (1996)). Thus, the expression of bacterial genes by plant cells has been accomplished.

Plants engineered with a foreign gene have been successful delivery agents for oral vaccines. As set forth in a recent review, (Mason and Arntzen, Tibtech 13: 388–392 (1995)), the art has recognized such uses of engineered plants. The body of work also includes the recent demonstration that, when expressing genes that code for antigens of viral and bacterial pathogens in plants, the antigens retain their immunogenic properties (Mason and Arntzen, Tibtech 13: 388–392 (1995)). Mason et al. (Mason et al, Proc. Natl. Acad. Sci. USA 89: 11745–11749 (1992)) introduced the concept of engineering plants as a vehicle delivery system for vaccines and have since shown that their system is effective for hepatitis B (Thanavala et al., Proc. Natl. Acad. Sci. 92: 3358–3361 (1995)), *E. coli* enterotoxin B subunit and cholera-toxin B subunit (Haq et al., Science 268: 714–716 (1995)). One basis for the effectiveness of this strategy rests on the fact that the antigens stimulate mucosal immunity.

In the practice of this invention, a fragment of the intimin gene, eae (which may, for example, contain the his tag, such as the XhoI-HindIII fragment of pEB313) is ligated to a plant promoter in an appropriate vector. The introduction of this vector in, for example, tobacco plants by appropriate methods results in the expression of intimin, such as his-intimin, by the tobacco plants. Once the tobacco plants are grown, they are homogenized to make a "tobacco soup" (protein extract). This soup is then used as an adsorbent for an ELISA, using standard methodology, to detect the presence of intimin. Alternatively, this extract is run on an SDS-PAGE gel for Western blot analysis. One can use polyclonal antisera directed against the intimin or, to detect the presence of a histidine tag, antibody directed against the his tag (available from QIAGEN) for such analysis. The amount of intimin expressed from the plant can be quantitated using the ELISA or Western blots.

Using a similar approach, a skilled artisan may express intimin, or for example intimin as a fusion protein with one or more other antigens, in the tobacco plant or other plants, such as carrots, bananas, canola, and alfalfa, although other plants are within the scope of the invention. When such transformed plants are fed to animals, such as cattle, the transformed plants express the intimin protein or the fusion protein, thereby delivering the antigens to the animals, in order to stimulate an immune response. Such a method is desirable in that it is an inexpensive and efficient method for protecting the animal and, moreover, protecting against future colonization of such animals by human pathogens such as EHEC reduces the risk of infection for humans.

In one transformation procedure, the eae gene is put under the control of a constitutive plant promotor in an *Agrobacterium tumefaciens* binary vector and the plants are engineered by Agrobacterium-mediated transformation.

The intimin expressed in the host organism is of a size that retains binding function, and may include intimin that has been histidine tagged. In addition, the intimin may be expressed in the host as a fusion protein with one or more other antigens. Administration of the host to patients, including animals, stimulates an immune response to the intimin and the one or more antigen.

Those skilled in the art will also recognize that the size of the his-tagged intimin to be used may be varied according to the specific purpose for administering the intimin. For example, if the his-tagged intimin is to be conjugated with one or more antigens, a smaller fragment may be selected to enhance stability of the combined fusion product; although the use of a larger fragment is by no means precluded. The size or conformation of the other antigen and the location of its significant epitopes may indicate that a particular length of his-tagged intimin will bring the epitopes into close proximity to the mucosa. The desired size will also vary with the convenience of available restriction sites, in light of the materials and methods known to those of ordinary skill in the art. Consequently, the terms his-intimin and his-tagged intimin, as used herein, mean polypeptides containing at least 900 out of the 935 predicted C-terminal amino acids of intimin with a histidine tag (full-length intimin) and smaller portions of the his-tagged protein that retain binding function.

The conjugate may be generated through recombinant technology to generate a fusion protein comprising a portion of intimin and at least one additional protein antigen or drug. In addition, intimin may be chemically or physically conjugated to drugs, proteins, peptides, carbohydrates and other antigens by methods known to those skilled in the art. Methods of chemical conjugation are well known to those skilled in the art, and include, in part, coupling through available functional groups (such as amino, carboxyl, thio and aldehyde groups). See S. S. Wong, Chemistry of Protein Conjugate and Crosslinking CRC Press (1991); and Brenkeley et al. Brief Survey of Methods for Preparing Protein Conjugates With Dyes, Haptens and Cross-linking Agents, Bioconjugate Chemistry 3 #1 (January1992).

The retention of binding function means that the intimin, intimin-like proteins, and/or portions thereof retain the capacity to bind to epithelial cells or cell lines, such as HEp-2 and HCT-8. Such binding may be visualized as bacterial microcolony formation by the microcolony assay (Frankel et al., Infect. Immun. 62(5):1835–1842 (1994)), by FAS, (florescence actin staining), or both (McKee and O'Brien, Infect. Immun. 63(5):2070–2074 (1995), the disclosures of which is incorporated by reference herein). Additionally, binding may be measured by any method standard in the art including in vivo measurement as a function of bacterial virulance or pathogenicity, or by post-mortem histological examination. Examples of each of the above methods for determining binding function are detailed in Examples below, including the adherence assay described in Example IV.

Unless specified otherwise, the uses and methods set forth herein are generally applicable to humans and animals. The term patient is used herein to mean both humans and animals, and animals is not limited to domesticated animals but also may include wildlife and laboratory animals as well.

Isolating and Purifying His-tagged Intimin

It has been shown that a His-intimin fusion, in which the N-terminal third of the molecule is deleted (RVHindHis), was capable of complementing adherence of a non-adherent EHEC eae mutant; i.e., restored binding capability to a strain of EHEC that lost its binding capability following genetic alterations that prevented expression of intimin. The pattern of adherence demonstrated in the restored binding was indistinguishable from that observed in wild-type strain 86-24 (McKee, M. L. and O'Brien, A.D. Infect. Immun. In press (1996)). Where measured by the microcolony assay, described above, wild-type activity is identified as a punctate pattern with localized areas of intense staining.

Purification of the intimin protein, however, was difficult, in part because intimin is always associated with the outer membrane of EHEC. The majority of the overexpressed recombinant intimin remained associated with the bacterial membrane fraction, even after sonic disruption of the host bacterium and addition of mild detergent to the extraction buffer. The insolubility of the intimin protein, combined with the abundance of other native *E. coli* proteins in the 97 kDa range, made purification of the native protein difficult.

Attempts to make an intimin-maltose binding protein fusion (MBP) also were unsuccessful because the predicted protein product had deletions and rearrangements. An attempt by other investigators had shown a construct of MBP fusions to the C-terminal 280 amino acids of intimin, but the fusion did not confer EHEC-like binding function. The diffuse pattern of adherence conferred by the MBP-intimin fusion protein was clearly different from the pattern of EHEC binding to HEp-2 cells (Frankel, G. et al. Infect. Immun. 62:1835 (1994)).

One possible explanation for the failure to obtain a functional MBP-intimin fusion larger than 280 amino acids is that overexpression of a piece of Eae greater than the last 280 amino acids is unstable, and thus prone to rearrangements, i.e. it may be impossible to isolate that clone because it is lethal or deleterious to the cell when expressed. Alternatively, overexpression of a piece of MBP-intimin fusion larger than 280 amino acids could plug up the bacterial membrane, which would be lethal to the cells.

After trying unsuccessfully to purify intimin using MBP, a fusion was created using the QIAEXPRESSIONIST® Kit (Qiagen, Inc., 6xHis tagged protein constructs purified on nickel-nitrilotriacetic acid (Ni-NTA) metal affinity chromatography), which involves attaching a histidine tag to the protein. The histidine tag binds tightly to a nickel affinity matrix, which facilitates purification of large quantities of material for further studies. In addition, the expression system permits one to maintain tight control of expression of the His fusion proteins to prevent any possible lethal effects of the recombinant protein on the *E. coli* host strain as a result of overexpression of the protein. Example I describes the creation of such a fusion protein.

EXAMPLE I

A. Construction of a Plasmid, pEB313 (FIG. 1), Encoding His-tagged Intimin Encompassing 900 out of 935 Predicted Amino Acids (FIG. 2).

The eae gene is cloned from EHEC strain 86-24 (serotype 0157:H7), readily obtainable from Griffin, P. M. et al., Ann. Intern. Med. 109:705–712 (1988), or Phil Tarr (Children's Hospital and Medical Center, 4800 Sand Point Way NE, Seattle, Wash. 98105, 206-526-2521.) The DNA is extracted according to standard chromosomal prep techniques (Wilson, K. in Current Protocols in Molecular Biology, Ausubel, F. M. et al. (eds.) vol 1:2.4.1—"Preparation of Genomic DNA from Bacteria").

The gene is cloned using the polymerase chain reaction (PCR), a standard technique in the art, using primers designed from a composite of the 2 known EHEC eae sequences. Two primers are constructed: Sn20-CGTTGTTAAGTCAATGGAAAC (SEQ ID NO:1), a 5' primer, spanning bases 20–41 of the sequence from the strain CL8, which was sequenced by Beebakhee, G. et al. FEMS Microbiology. 91:63 (1992) (FIG. 3); and MM2-TCTAGAGAGAAAACGTGAATGTTGTCTCT (SEQ ID NO:2), a 3' primer, spanning bases 3061–3082 of the sequence from strain 933, sequenced by Yu, J. and Kaper, J. B. Mol. Microbiol. 6:411 (1992) (FIG. 4). MM2 was further designed to include an XbaI site at the 3' end.

The PCR reactions are performed using a PCR reagent kit utilizing AMPLITAQ®, a DNA polymerase, according to the instructions of the manufacturer, Perkin Elmer. The PCR amplification produces a 3144 bp fragment encoding the entire eae open reading frame (ORF) (FIG. 5, region designated eae) and includes 186 bp upstream. The PCR product is processed to create blunt ends and ligated into the EcoRV site of the vector $pBRKS^-$ (Schmitt et al., J. Bacteriol. 176:368–377 (1994)).

The gene is cloned in both directions to allow transcription from either $P_{lac}$ pEB311 (FIG. 6) and from $P_{T7}$ pEB310 (FIG. 7) under the appropriate conditions. The plasmids are transformed into host strain XL1BlueF'Tn5 $lacI_Q$, (available from QIAGEN, Inc., 9600 DeSoto Ave., Chatsworth, Calif. 91311, 1-800-362-7737). The recombinants are maintained under the constitutive control of the lac repressor, because the previous failed attempts to clone eae suggested that overexpression of eae might be lethal to the host *E. coli* strain. The lower copy number of $pBRKS^-$ vector, along with the control conferred by the lac repressor obviates these problems.

A his-tagged intimin plasmid is constructed by digesting pEB310 with EcoRI, filling in with Klenow fragment, digesting with HindIII, and isolating the resulting 2895 bp fragment. The DNA fragments are isolated using the GENECLEAN®, an agarose gel DNA purification procedure (BIO 101, Inc. 1070 Joshua Way, Vista, Calif. 92083, 1-800-424-61010). The his-tag expression plasmid pQE32 (FIG. 8) (available from QIAGEN, Inc.) is digested with SmaI and HindIII. The 2895 bp fragment is then ligated to pQE32, creating pEB313 (FIG. 1).

This plasmid, pEB313, encodes a his-tagged Eae fragment of 101 kDa, called RIHisEae, which encodes 900 out of 935 predicted amino acids. This his-intimin fusion is constructed so that the N terminal 35 amino acids are deleted, to remove any potential signal sequence. A signal sequence could target the fusion protein to the membrane or lead to cleavage of the His tag from the encoded intimin.

After the pEB313 construct is made, it is transformed into a lab strain of *E. coli* containing the lac repressor ($lacI_Q$), such as M15 pREP4 (repressor contained on the multicopy plasmid pREP4, supplied by QIAGEN, Inc.) (FIG. 9) or XL1 BlueF'Tn5 $lacI_Q$ (repressor contained on the single copy F' plasmid, also available from QIAGEN, Inc.). The transformed *E. coli* express the his-intimin fusion protein encoded by pEB313. Purification of the protein is accomplished as set forth in Example III.

B. Construction of a Plasmid, pHis-Inv1, Encoding His-tagged *Yersinia Pseudotuberculosis* Invasin, and Construction of a Plasmid, pHis-Inv2, Encoding His-tagged *Yersinia Pseudotuberculosis* Invasin with a Deletion of the N-terminal 40 Amino Acids.

The plasmid pRI203 contains a 4.6 kb fragment of *Yersinia pseudotuberculosis* chromosomal DNA, including the inv gene and surrounding nucleotides sequences, and is readily obtainable from Dr. Ralph Isberg (Dept. Of Molecular Biology and Microbiology, Tufts University School of Medicine, Boston, Mass. 02111; ref. R. R. Isberg, D. L. Voorhis, and S. Falkow. Cell. 50:769 (1987)). The pRI203 DNA is extracted from the supplied bacterial strain with the use of a QIAGEN DNA extraction kit (QIAGEN, Chatsworth, Calif.) according to the instructions of the manufacturer.

To construct pHis-Inv1, two primers, Inv1 (=5' GTACGGATCCATGATGGTTTTCCAGCCATCAGTGAG 3' (SEQ ID NO:3) and Inv3 (=5' GTACGGTACCTTATATTGACAGCGCACAGAGCGGG 3' (SEQ ID NO:4)) are used in a PCR reaction (as described above in part A) to amplify the desired inv sequences from pRI203. The resulting 2960 bp inv fragment is digested with BamHI and KpnI, run on an agarose gel, excised with a razor, and purified using GENECLEAN® (Bio101, La Jolla, Calif.). The purified inv fragment is ligated into the His-tag QIAGEN vector containing the appropriate reading frame corresponding to the amplified inv sequence (pQE30, 31 or 32, QIAGEN, Chatsworth, Calif.), digested with BamHI and KpnI. The ligated plasmids are then transformed into DH5αF'Tn5lacI$_Q$, and transformants checked for the presence of the appropriate size insert.

The plasmid pHis-Inv2 is constructed in the event that a signal sequence (and therefore the adjoining His tag) is cleaved from the protein expressed from pHis-Inv1. To construct pHis-Inv2, two primers, Inv2 (=5' GTACGGATCCATATGTGGATGATCATGGCTGGGG 3' (SEQ ID NO:5)) and Inv3 (=5' GTACGGTACCATATAATGACAGCGCACAGAGCGGG 3' (SEQ ID NO:4)) are used in a PCR reaction (as described in part A above) to amplify the desired inv sequences from pRI203. The resulting 2840 bp inv fragment is purified as above, and ligated into the His-tag QIAGEN vector as above, and transformed into a similar bacterial host strain.

Alternatively, similar plasmids are constructed by restriction enzyme digestion of pRI203, followed by ligation into the QIAGEN His-tag vector (pQE30, 31 or 32) containing the appropriate reading frame relative to the 5' end of the invasin fragment. The preceding examples are meant to illustrate the construction of plasmids encoding histidine-tagged invasin from *Yersinia pseudotubercuis*. One of ordinary skill in the art recognizes that analogous constructs, designed using alternative vectors and/or other intimin-like proteins can be constructed according to standard methods in the art. One of ordinary skill in the art also recognizes that the above his-tagged invasins and other his-tagged intimin-like proteins may be applied to the methods disclosed elsewhere herein.

C. Construction of a Plasmid (pEB312) (FIG. 10) Encoding His-tagged Intimin Encompassing 604 out of 935 Predicted Amino Acids.

Digested plasmid pEB310 (obtained as described in part A) with EcoRVand HindIII, isolating the 1971 bp fragment, and ligating the fragment into pQE32 digested with SmaI and HindIII. Restriction enzymes, ligases, Klenow fragment used in protocols are from New England BioLabs (32 Tozer Rd., Beverly, Mass. 01915-55991, 1-800-NEB-LABS) or Gibco BRL (P.O. Box 681 Grand Island, N.Y. 14072-0068, 1-800-828-8686). The resulting plasmid is designated pEB312.

The plasmid pEB312 encodes a his-tagged Eae fragment called RVHindHis, which is about 65 kDa and encodes 604 out of 935 predicted amino acids. This construct contains the C-terminal two-thirds of the wild-type intimin protein.

As with the pEB310-expressed intimin, the fusion proteins remain primarily in the insoluble pellet after sonic disruption of the host *E. coli*. Therefore, urea and guanidine HCl are included in the purification protocol, which allows extraction of the fusion proteins from the insoluble pellet.

D. Construction of Additional Plasmids Expressing Different Fragments of eae.

Each of these plasmids is tested to ensure that the protein fragment possesses full binding function, using an adherence assay. (See example IV, below). In addition, the selection of the size of the intimin varies with whether the protein is expressed alone and whether cross-immunity is desired with an intimin-like protein of known amino acid sequence. In addition to intimin expressed from EHEC and EPEC, examples of intimin-like proteins include, but are not limited to, intimin-like proteins of *Citrobacter rodentium, Hafina alveii*, and the invasins of *Yersinia enterocolitica* and *Yersinia pseudotuberculosis.*

For instance, the larger 900 aa intimin is selected if there is heightened desire for cross-immunity with *Yersinia pseudotuberculosis*, because EHEC intimin shares 31% identical and 51% similar amino acids with the protein of *Yersinia pseudotuberculosis*, known as invasin (Yu, J. and Kaper, J. B. Mol. Microbiol. 6:411 (1992)). A greater degree of homology exists within the amino terminal two-thirds of the respective proteins.

Invasin is a 103 kDa outer membrane protein that allows bacterial penetration of cultured epithelial cells (Isberg, R. R. et al. Cell. 60:769 (1987)) and efficient penetration of the intestinal epithelium in vivo (Pepe. J. C. and V. L. Miller. Proc. Natl Acad. Sci. USA. 90:6473 (1993)). Cell adhesion receptors on the intestinal epithelium, which have been identified as integrins, bind invasin prior to bacterial internalization (Isberg, R. R. and J. M. Leong. Cell. 50:861 (1990)). The central portion of invasin is responsible for protein localization to the outer membrane, while the C-terminus is required for receptor binding (Isberg, R. R. Mol. Microbiol. 3:1449 (1989)).

Similarly, a larger 900 aa intimin is selected if there is heightened desire for cross-immunity with Enteropathogenic *Escherichia coli* (EPEC), *Citobacter rodentium*, or *Hafnia alvei*. EPEC intimin shares 83% identity with EHEC intimin over the entire length of the protein; the N-terminal 75% of the proteins share 94% identity, while the C-terminal 25% of the proteins share 49% identity (Yu, J. and Kaper, J. B. Mol. Microbiol. 6:411 (1992)). *Citrobacter freundi* intimin shares 84% nucleotide identity to EHEC eae with the first 2106 bp, and 57% identity to the 3' 702 bp (Schauer, D. B. and Falkow, S. Infect. Immun. 61:2486 (1993)).

The plasmids that express different fragments of eae can be constructed using one of the following techniques: (1) use of a convenient restriction site within eae, for example, pEB313 digested with SalI and HindIII, isolation of the 1298 bp fragment, and ligation to pQE30 (QIAGEN, Inc.) digested with SmaI and HindIII. The resulting plasmid expresses the last 432 amino acids at the C terminus of Eae; (2) deletion of the 5' or the 3' region of any desired fragment using nuclease BAL-31, Exonuclease III, or Mung bean nuclease (all available from New England BioLabs, 32 Tozer Rd., Beverly, Mass. 01915); (3) construction of plasmids with noncontiguous eae fragments, also using the above techniques; and (4) construction of plasmids encoding desired specific sequences with the use of PCR primers specifying the 5' and 3' ends of such sequences, as described in greater detail below.

With respect to the third technique, a His-tagged middle third intimin deletion mutant plasmid is constructed (pMW114). The plasmid pMW106 (described below) is transformed into the dam strain DM1F'Tn5lacI$_Q$. DNA is made using the QIAGEN kit (QIAGEN, Inc.), an alkaline lysis/anion exchange chromatography plasmid purification system and is digested with BclI. The DNA is runout on an agarose gel. The 5178 bp band is cut out, is purified using GENECLEAN® (Bio 101), is ligated, and then transformed into DH5αF'Tn5lacI$_Q$ (or other appropriate strain such as XL1Blue or M15pREP4). Transformants are checked by restriction digestion of DNA. This description does not preclude the construction of other plasmids encoding noncontiguous eae sequences.

With respect to the fourth technique, PCR can be used to amplify specific fragments of eae; the fragments are isolated by restriction enzyme digestion and agarose gel electrophoresis, and ligated into the appropriate His-tag expression vector (i.e. p.QE30, 31 or 32; QIAGEN, Inc.).

Figure 11:
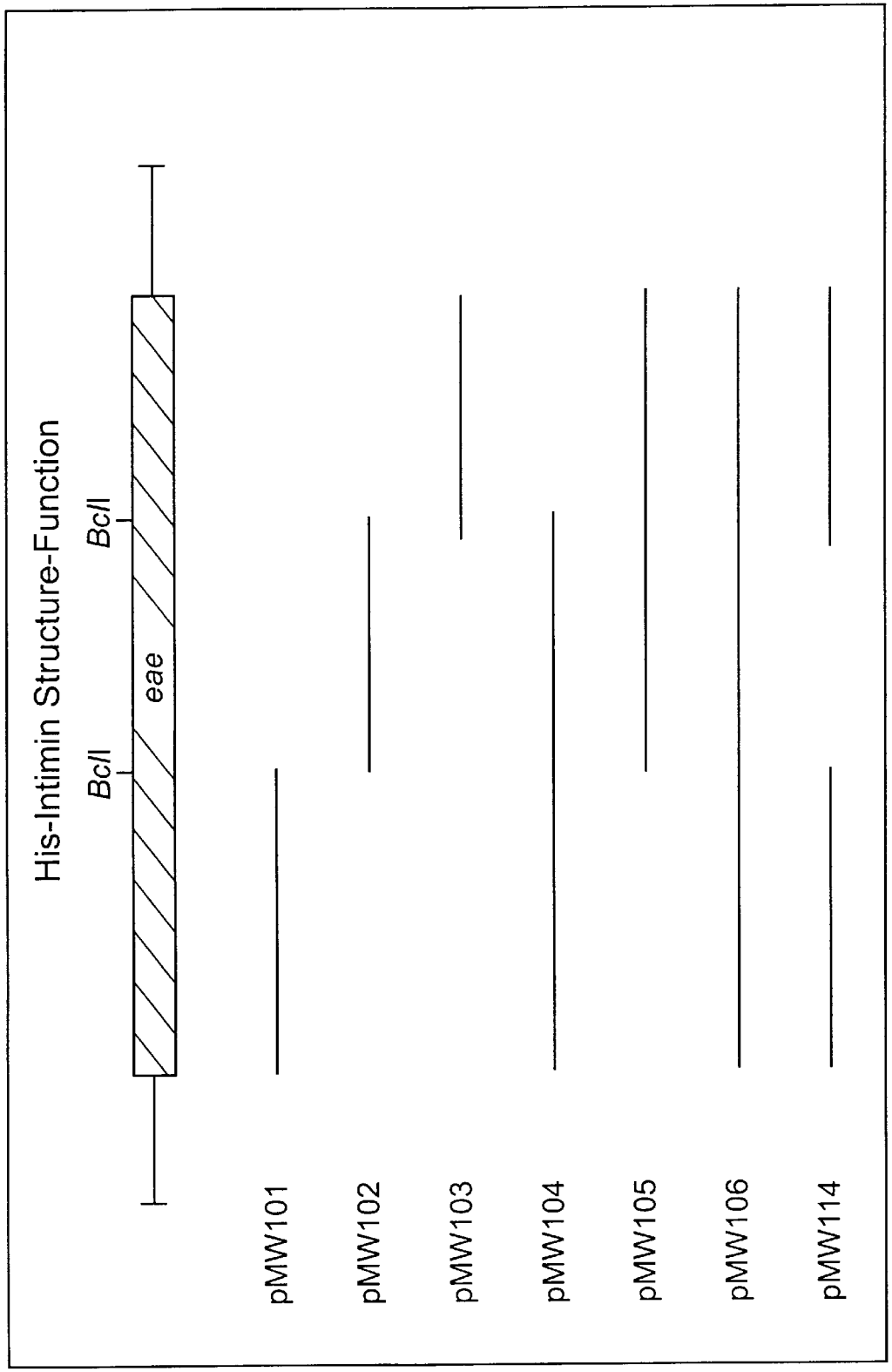
Figure 12:
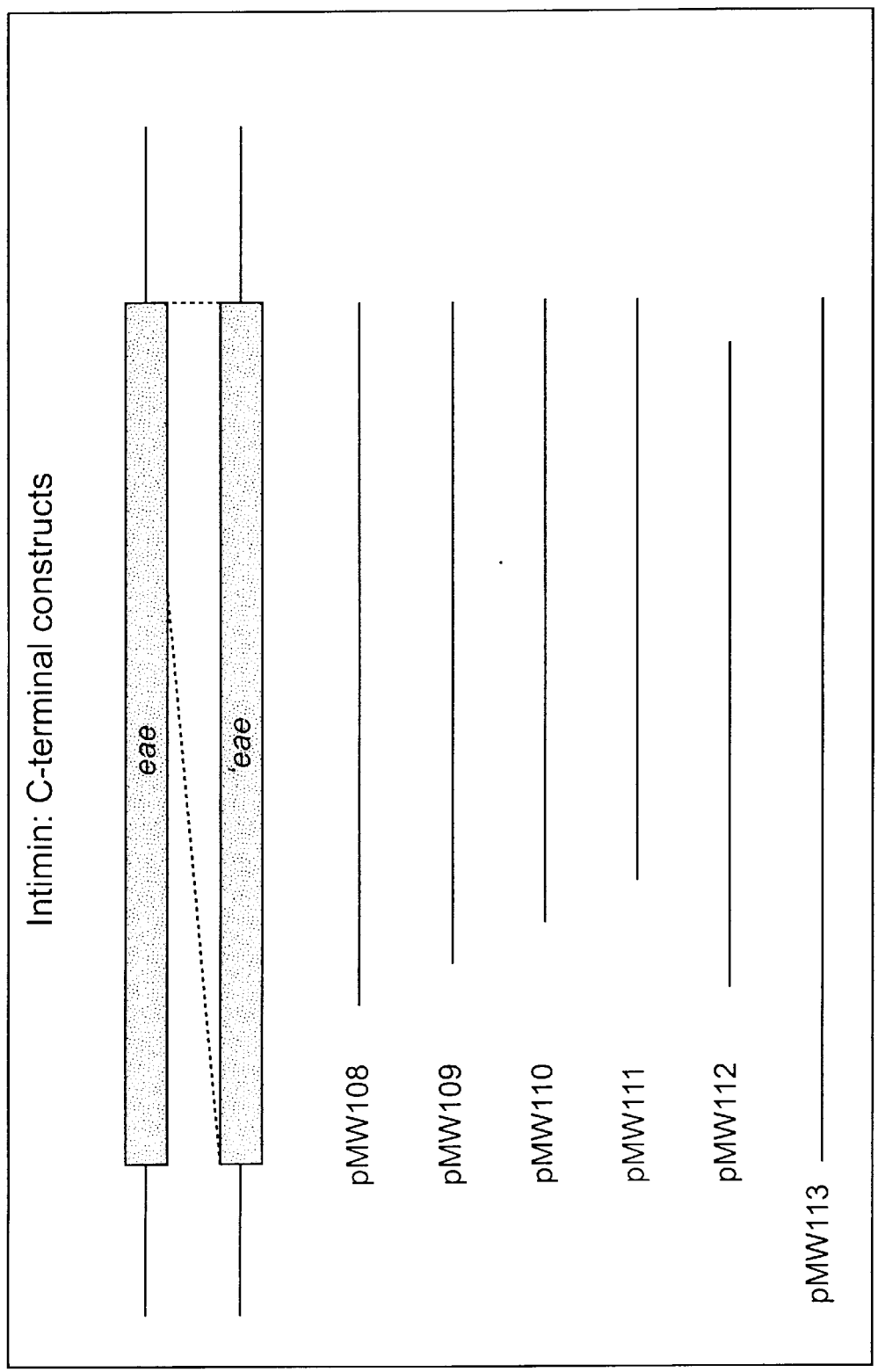

For example, clones are constructed encoding various regions of eae (see FIGS. 11 and 12). The capacity of these clones to retain adherence function is assessed by either (1) transformation into the eae mutant, followed by adherence assays with HEp-2 cells (see Ex III, section C), or (2) addition of exogenous protein to bacteria (see Ex III, section D). It is important that the fragment selected retains full or as close to full wild type binding activity.

It is hypothesized that clones containing the highest binding activity will include the C-terminal third (third third) of the protein, perhaps as little as 150 C-terminal amino acids. This hypothesis is supported, for example, by the findings disclosed by Frankel et al., Infection & Immunity, 62:1835 (1994), Frankel et al., Infection & Immunity, 63:4323 (1995), and Frankel et al., J. Biol. Chem., 271:20359 (1996). Proteins cannot be thought of as linear arrays of amino acids; rather they exist in a 3-dimensional structure. It is important to keep in mind that a single amino acid change or a deletion of a portion of the protein can perturb this structure. Therefore, full cell binding activity may require the presence of additional noncontiguous sequences along with the third third putative binding domain.

It is further hypothesized that clones containing high binding activity will include the two C-terminal Cys (encoded at bp 2780 and bp 3002, numbering ref; Beebakhee, G., J. DeAzavedo, and J. Brunton, FEMS Microbiology Letters 91:63 (1992)) for hypothesized disulfide bond formation and resulting loop formation. Additionally, it is hypothesized that clones containing high binding activity may require one or both aspartate(s) (encoded at bp 2819 and 2828, numbering ref. Beebakhee). This hypothesis is supported, for example, by analogy to invasin, as described in Leong, J. M., Embo. J. 14:422 (1995).

All clones are constructed in a similar manner. PCR primers are designed which specify the 5' and 3' region of the desired eae fragment. To facilitate cloning into pQE31, each 5' primer (MW1, MW3, MW5, MW7, MW8, MW9, MW10) contains a 5' BamHI site, and each 3' primer (MW2, MW4, MW6, MW11, MW12) contains a 5' KpnI site. Each PCR primer is designed so that the reading frame of the specified eae sequence is appropriate for insertion into pQE31. The following His-tagged constructs are cloned using the indicated PCR primers:

(1) pMW101—encodes the N-terminal third of Eae; 27 kDa protein (PCR primers: MW1 (5' PCR primer)=5' GTACGGATCCGATTCATTTGCAAATGGTG 3' (SEQ ID NO:6); MW2 (3' PCR primer)=5' GTACGGTACCTGATCAATGAGACGTTATAG 3' (SEQ ID NO:7));

(2) pMW102—encodes the middle third of Eae; 42 kDa protein (PCR primers MW3 (5' PCR primer)=5' GTACGGATCCTGATCAGGATTTTTCTGGTG 3' (SEQ ID NO:8)); MW4 (3' PCR primer)=5' GTACGGTACCTGATCAAAATATAACCGC 3' (SEQ ID NO:9));

(3) pMW103—encodes the C-terminal third (282 amino acids) of Eae; 32 kDa protein (PCR primers: MW5 (5' PCR primer)=5' GTACGGATCCTGATCAAACCAGGCCAGCATTAC 3' (SEQ ID NO:10); MW6 (3' PCR primer)=5' GTACGGTACCTTATTCTACACAAACCGCATAG 3' (SEQ ID NO:11));

(4) pMW104—encodes the N-terminal two thirds of Eae; 69 kDa protein (PCR primers: MW1 and MW4);

(5) p MW105—encodes the C-terminal two thirds of Eae; 73 kDa protein (PCR primers: MW3 and MW6);

(6) pMW106—encodes Eae with a small N-terminal 35 amino acid deletion; 100 kDa protein (PCR primers: MW1 and MW6);

(7) pMW108—encodes the C-terminal 150 amino acids of Eae (PCR primers: MW7 (5' PCR primer)=5' GTACGGATCCACTGAAAGCAAGCGGTGGTGATG 3' (SEQ ID NO:12); MW6);

(8) pMW 109—encodes the C-terminal 140 amino acids of Eae (PCR primers: MW8 (5' PCR primer)=5' GTACGGATCCTTCATGGTATTCAGAAAATAC 3' (SEQ ID NO:13); MW6);

(9) pMW110—encodes the C-terminal 130 amino acids of Eae (PCR primers: MW9 (5' PCR primer)=5' GTACGGATCCGACTGTCGATGCATCAGGGAAAG 3' (SEQ ID NO:14); MW6);

(10) pMW111—encodes the C-terminal 120 amino acids of Eae (PCR primers: MW10 (5' PCR primer)=5' GTACGGATCCGAATGGTAAAGGCAGTGTCG 3' (SEQ ID NO:15); MW6);

(11) pMW 112—encodes 120 amino acids of Eae with the C-terminus, spanning bp #2560–2923, (numbering refers to eae sequence of strain CL8 ref. Beebakhee, G., J. DeAzavedo, and J. Brunton. FEMS Microbiology Letters 91:63)). (PCR primers: MW7; MW11 (3' PCR primer)=5' GTACGGTACCTCCAGAACGCTGCTCACTAG 3' (SEQ ID NO:16));

(12) pMW113—encodes the C-terminal 282 amino acids of Eae, Cys at bp 3002 changed to Ser with the use of the PCR primer MW12 (numbering refers to eae sequence of strain CL8 ref. Beebakhee, G., J. DeAzavedo, and J. Brunton. FEMS Microbiology Letters 91:63 (1992)) (PCR primers: MW5; MW12 (3' PCR primer)=5' GTACGGTACCTTATTCTACAGAAACCGCATAG 3' (SEQ ID NO:17)).

All clones are constructed by first diluting lyophilized primers to 10 μM with dH$_2$O. Template DNA from strain XL 1blue pEB310 (encoding the entire eae gene) is made using a QIAGEN prep (QIAGEN, Inc.), is linearized by digestion with a restriction enzyme that does not cut within or near the coding region, for example HindIII, and is quantitated using a spectrophotometer. PCR reactions are conducted by combining 10 μl 10X Taq buffer (Perkin Elmer/Roche, Branchburg, N.J.), 10 μl 2 mM dNTP mix (Boehringer Mannheim, Indianapolis, Ind.), 10 μl 10 μM 5' PCR primer, 10 μl 10 μM 3' PCR primer, 6 μl 25 mM MgCl$_2$ (Perkin Elmer/Roche), 52 µl dH$_2$O, and 1 µl (1–10 ng) linear template DNA. Two drops of mineral oil are applied to the mixture, which is heated to 100° C. for 5 minutes to denature the template. One µl (5U) of AMPLITAQ® polymerase (Perkin Elmer/Roche) is added, and the PCR reactions are begun: 95° C./ 1 min, 50° C./ 1 min, 72° C./ 3 min for 30 cycles, followed by 72° C./ 10 min, and holding at 4° C. After the PCR reactions are completed, the DNA is applied to a WIZARD® (Promega Madison Wis.),. resin based PCR clean, up kit, and resuspended in 50 µl TE buffer. PCR amplified DNA is digested with BamHI and KpnI, electrophoresed on an agarose gel, the appropriate size band cut out, and purified by Gene Clean (Bio101, La Jolla, Calif.). Digested PCR fragments are then ligated into pQE31 digested with BamHI and KpnI, transformed into DH5αF"Tn5lacI$_Q$ (or other appropriate strain, such as M15pREP4 or XL 1Blue), and transformants checked for the presence of the appropriate size insert.

With respect to any of the above-listed techniques, if it is necessary to later remove the Histidine tag from the purified protein, a protease cleavage site can be inserted between the 6XHis sequence and the N-(N-terminal tag) or C-terminus (C-terminal tag) of the protein. For example, Enterokinase recognizes the sequence "DDDDK" SEQ ID NO:26(Asp$_4$-Lys), and cleaves after the lysine. A PCR primer encoding this sequence is designed and used to perform site-directed mutagenesis of the desired gene fragment. Alternatively, Carboxypeptidase A can be used for the removal of C-terminal His tags. This enzyme efficiently removes aromatic C-terminal residues (Hoculi, E. Chemische Industrie. 12:69 (1989)) until it encounters a basic residue, at which point removal is terminated. Additionally, PCR can be used to design a primer so that the protease site is encoded at the N- or C-terminus of the protein encoded; or PCR can be used to design the vector including those sites, and the above-techniques can be used to clone into the aforementioned vector.

All fragments of intimin expressed from pEB312 or other constructs are purified using a protocol similar to the protocol detailed in Example II, for large scale purification of intimin. It is apparent that those of ordinary skill in the art may select additional restriction sites or modify the protocol while remaining within the scope and spirit of the invention.

EXAMPLE II

Large Scale Enrichment of Histidine-tagged Intimin
Growing Large-Scale Expression Cultures Inoculate 20 ml LB (Luria-Bertaini) broth containing 100 µg/ml ampicillin and 40 µg/ml kanamycin with a loopful of M15 pREP4 pEB313 (prepared as described in Example I, above). Grow overnight (15–18 h) at 37° C., shaking vigorously. Inoculate 1 L of LB broth containing 100 µg/ml ampicillin and 40 µg/ml kanamycin with 20 ml of the overnight culture. Grow culture at 37° C. with vigorous shaking until the OD$_{600}$=0.7–0.9 (~3 h). Add IPTG (isopropyl β-D-thiogalactopyranoside, Sigma Chemical Co., P.O. Box 14508, St. Louis, Mo. 63178, 1-800-325-3010) to a final concentration of 1 mM (.476 g) and continue to grow culture for another 3 h. Divide supernatant into 500 ml bottles (previously weighed) and centrifuge at 4000×g for 10 minutes. Discard the supernatant, weigh cell pellet, and store at −70° C., or process immediately.

Thaw cells for 15 minutes, vortex and resuspend in Buffer A [6 M GuHCl, 0.1 M NaH$_2$PO$_4$, 0.01 M Tris-HCl, pH 8.0] at 5 ml/g wet weight. Stir cells for 1 hour at room temperature. Centrifuge lysate at 10,000×g for 15 min, collect supernatant. Add 5 ml of a 50% slurry of Ni-NTA resin (Ni-NTA slurry from QIAGEN, Inc), previously equilibrated with Buffer A. Stir at room temperature for 45 minutes, let the slurry settle, remove the supernatant, add 5 ml Buffer A, let the slurry settle, remove the supernatant, add 5 ml Buffer A, and load the resin into a column. The column is washed with 10 column volumes of Buffer A, followed by washes with Buffer B [8 M urea, 0.1 M NaH$_2$PO$_4$, 0.01 M Tris-HCl, pH 8.0] until the OD$_{280}$≦0.01 (at least 5 column volumes). Wash the column with Buffer C [8M urea, 0.1 M NaH$_2$PO$_4$, 0.01 M Tris-HCl, pH 6.3] until the OD$_{280}$≦0.01. The protein is eluted with Buffer C plus 0.25 mM Imidazole, collecting thirty 1 ml fractions.

Record the OD$_{280}$ of each fraction. Pool aliquots of the purified protein into dialysis tubing (Spectra/Por Cellulose Ester Membrane MW cut off=8000; Spectrum Medical Industries, 1100 Rankin Rd. Houston, Tex. 77073-4716), and equilibrate in cold (4° C.) BufferC. Adjust the concentration of the aliquots to ≦1 mg/ml using a standard commercial protein quantitation kit (Bio-Rad Microassay, Bio-Rad Labs, 2000 Alfred Noble Dr., Hercules, Calif. 94547, 1-800-4BIORAD), with BSA diluted in Buffer C as the standard. Perform step dialysis of the protein in the cold (4° C.) beginning with Buffer C and reducing the molarity of the urea by whole number increments. Dialyze for one hour in each solution, ending in 1× PBS. Analyze the protein by (10%) SDS-PAGE running ~2 µl protein per well to verify protein size and quantity. The molecular weight of RIHisEae is 101 kDa.

Alternatively, add protein to dialysis tubing, dialyze straight into 1× PBS. Quantitate the protein using a standard commercial protein quantitation kit (Pierce BCA Protein Assay Kit, Pierce, P.O. Box 117, Rockford, Ill. 61105), aliquot, and store at −20° C. As with the first alternative, analyze the protein by (10%) SDS-PAGE running ~2 µl protein per well to verify protein size and quantity.

Upon enrichment of his-tagged intimin, the material derived is analyzed for level of purity by SDS-PAGE. A 10% SDS-PAGE gel is loaded with a 2 µl sample of enriched his-tagged intimin and electrophoresed at 200 V for one hour. Molecular weight markers are included on the gel for size comparison. When the gel is stained with Colloidal Coomasie stain (Sigma, St. Louis, Mo.), the most prominent appears at ~101 kDa. Several other less prominent high molecular weights bands also appear. When the gel is stained with silver stain (BioRad, Richmond, Calif.) according to the instructions of the manufacturer, very slight high molecular weight bands appear, as well as several more prominent bands at low molecular weights, the most prominent band appearing around 29kDa. The enriched product preferably contains approximately 70–80% of the full-length (i.e., 900 out of 935 predicted amino acids) intimin. Preferably the enriched product contains no more than 25% contaminants (i.e., non-intimin related molecules), more preferably no more than 20% contaminants, still more preferably no more than 10% contaminants.

EXAMPLE III

Purification of Enriched Histidine-Tagged Intimin

An enriched preparation of his-tagged intimin, generated as described in Example II above, is purified by techniques known to those skilled in the art, including, but not limited to, high performance liquid chromatography (HPLC), gel column chromatography, and SDS-PAGE.

With the SDS-PAGE method, an enriched preparation of his-tagged intimin is separated on a 10% polyacrylamide gel and visualized, for example, by staining an analytical lane with Colloidal Coomasie strain (Sigma, St. Louis, Mo.). The high molecular weight full-length intimin band can be excised from the preparative gel with a razor, and stored at 4° C. prior to immunization. Less than full-length fragments of intimin, i.e. portions of intimin, and/or intimin conjugated to one or more antigens can similarly be excised from the gel.

Regardless of the method used to purify intimin, or portion thereof, the purified protein as used herein refers to a population of polypeptides consisting solely of intimin or portions or intimin, optionally tagged with histidine. It has been recognized in the art that the population of polypeptides expressed from a fragment of DNA containing only one open reading frame encoding intimin (and intimin-like proteins) can separate into multiple bands on an SDS-PAGE gel. McKee et al., Infection & Immunity, 64(6):2225–2233 (1996), Jerse et al., Proc. Natl. Acad. Sci. USA 87:7839–7843 (1990), and Isberg, Cell 50:769–778 (1987). Thus, purified intimin, as well as portions of intimin and intimin conjugated with one or more antigens, may be visualized as multiple bands on an SDS-PAGE gel.

EXAMPLE IV

A. Adherence Assay.

Adherence of *E. coli* to either HEp-2 or HCT-8 cells is assessed by a modification of the method of Carvioto et al. Curr. Microbiol. 3: 95–99 (1979). Specifically, overlay semiconfluent monolayers of HEp-2 cells on glass coverslips in 24 well tissue culture dishes or in 8 well Permanox Chamber Slides (Nunc, Naperville, Ill.) with adherence assay medium (EMEM, or Eagle's Minimum Essential Medium supplemented with 0.4% sodium bicarbonate and 1% mannose) which contain 20 µl/ml (v/v) of an overnight culture of the bacteria to be tested in LB broth.

Each inoculum contains $\geq 10^7$ bacteria (described below) which results in an approximate multiplicity of infection (MOI) of 100:1. The infected monolayers are incubated at 37° C. in a 5% $CO_2$ atmosphere. After three hours, the medium, which contains the nonadherent bacteria, is aspirated and the monolayers washed once with sterile 10 mM phosphate buffered saline, pH 7.4 (PBS: sodium chloride, sodium phosphate dibasic, and potassium phosphate monobasic).

Fresh adherence assay medium is added to the cells with adherent bacteria, and the infected cells are then incubated for an additional 3 hours. The monolayers are then washed six times with PBS to remove nonadherent bacteria. Each wash is gently removed by aspiration in an attempt to avoid disturbing the monolayers. Each assay is done $\geq 2$ times and duplicate slides are prepared to permit both Giemsa and FITC-phalloidin (FAS) staining to visualize binding and associated sequelae.

For Giemsa staining, the HEp-2 cells and adherent bacteria are fixed with 70% (v/v) methanol (glass coverslips) or graded acetone washes (chamber slides) and stained with 1:10 Giemsa (Sigma) for 20 minutes. To assess the FAS phenotype, the FITC-Phalloidin (Sigma) staining procedure of Knutton et al. Infect. Immun. 57: 1290–1298 (1989) is used. Phalloidin is a mushroom phallotoxin that specifically binds filamentous, not globular, actin. FITC-phalloidin-stained preparations are examined by both phase contrast and fluorescent microscopy using an Olympus model GHS microscope with a model BH2-RFL reflected light fluorescence attachment (Olympus Optical Co., Ltd., Tokyo, Japan).

Adherence assays with HCT-8 cells are done by the procedure described above for HEp-2 cells, but the bacteria are allowed to interact with the HCT-8 cells for 2.5 hours before the first wash and an additional 2.5 hours before terminating the assay. All assays with HCT-8 cells are carried out in 8 well permanox Chamber Slides.

B. Construction of a Bacteria for Use in the Assay: An EHEC eae mutant.

Figure 13:
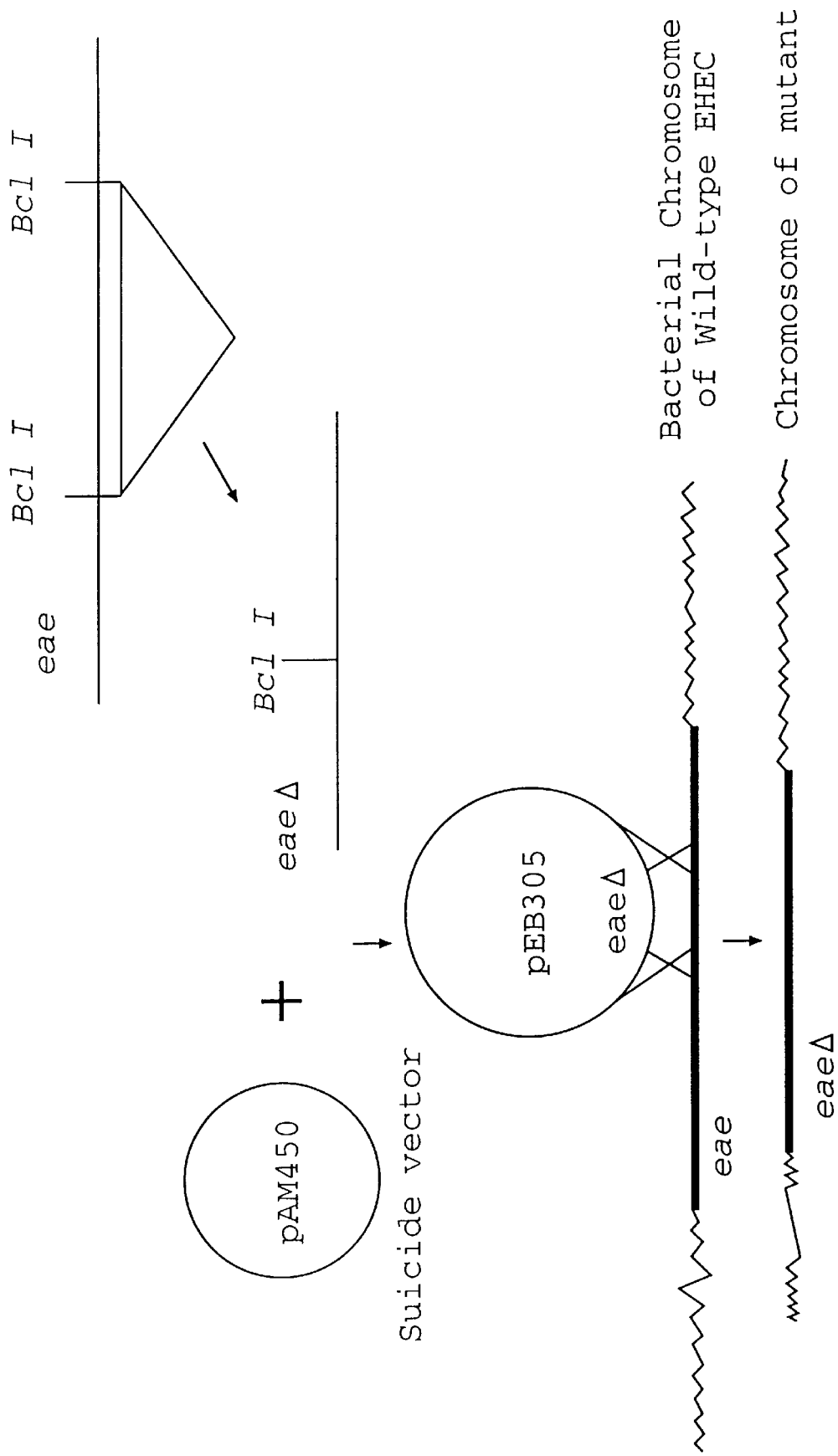
Figure 14:
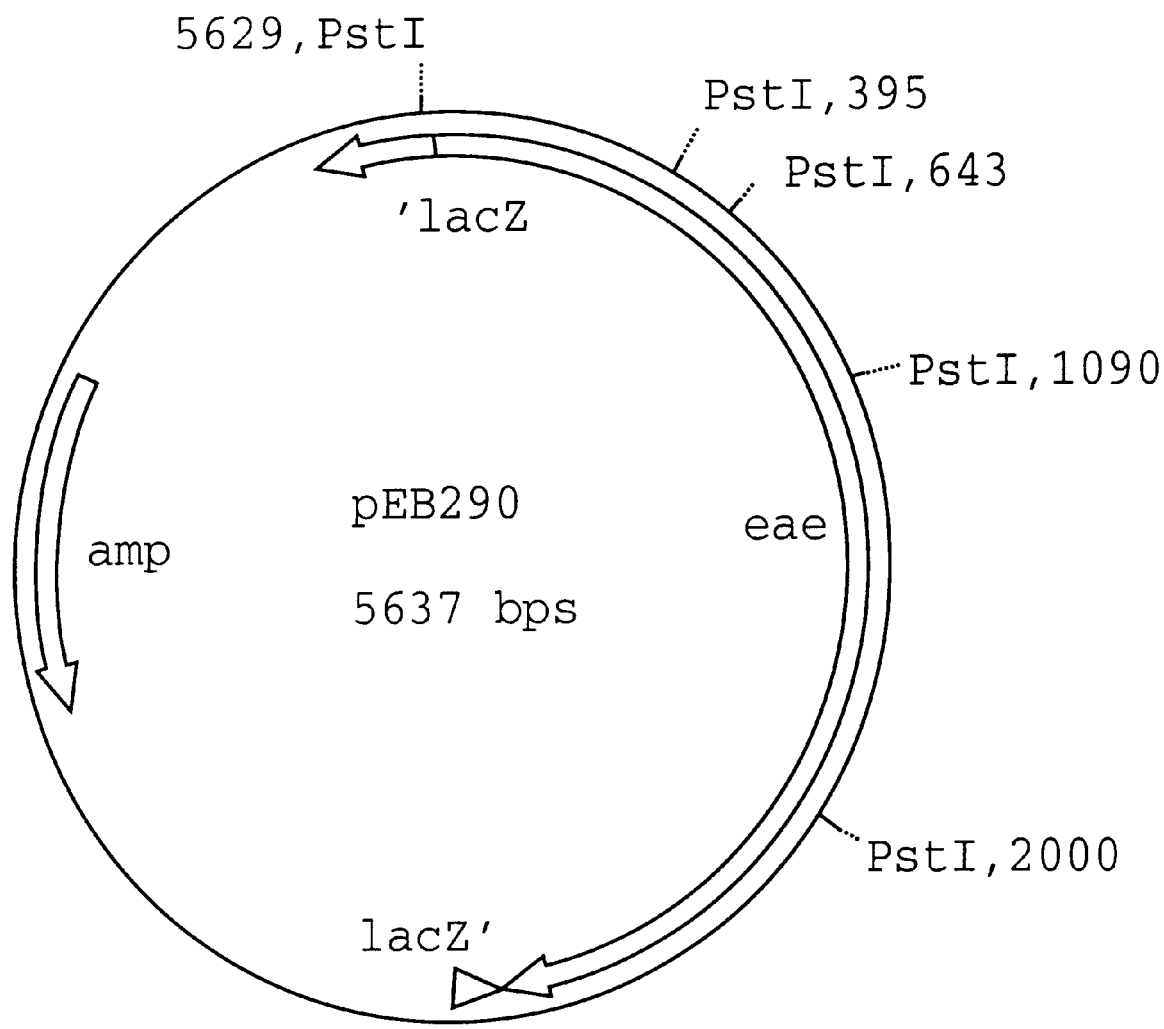

To create an in-frame deletion in the chromosomal copy of the eae gene in a particular strain of EHEC, strain 86-24, the wild-type copy of the gene is replaced by double homologous recombination with an internally-deleted copy of eae (FIG. 13). Plasmid pEB290 (FIG. 14) encloses most of the eae structural gene and is constructed from a PCR product amplified from the 86-24 chromosome with primer MM1 (MM1=ATAACATGAGTACTCATGGTTG (SEQ ID NO:18); starts at the second codon of the eae structural gene and includes a ScaI restriction site), in combination with primer MM2 (MM2=TCTAGAGAGAAAACGTGAATGTTGTCTCT (SEQ ID NO:2)). The resultant 2,953 base pair fragment derived by PCR is digested with the ScaI and XbaI and ligated into pBluescript SK+ (Stratagene) that is restricted with SmaI and XbaI. DNA sequencing of the ends of the pEB 290 insert reveals that the 3' 250 base pairs are lost.

Figure 15:
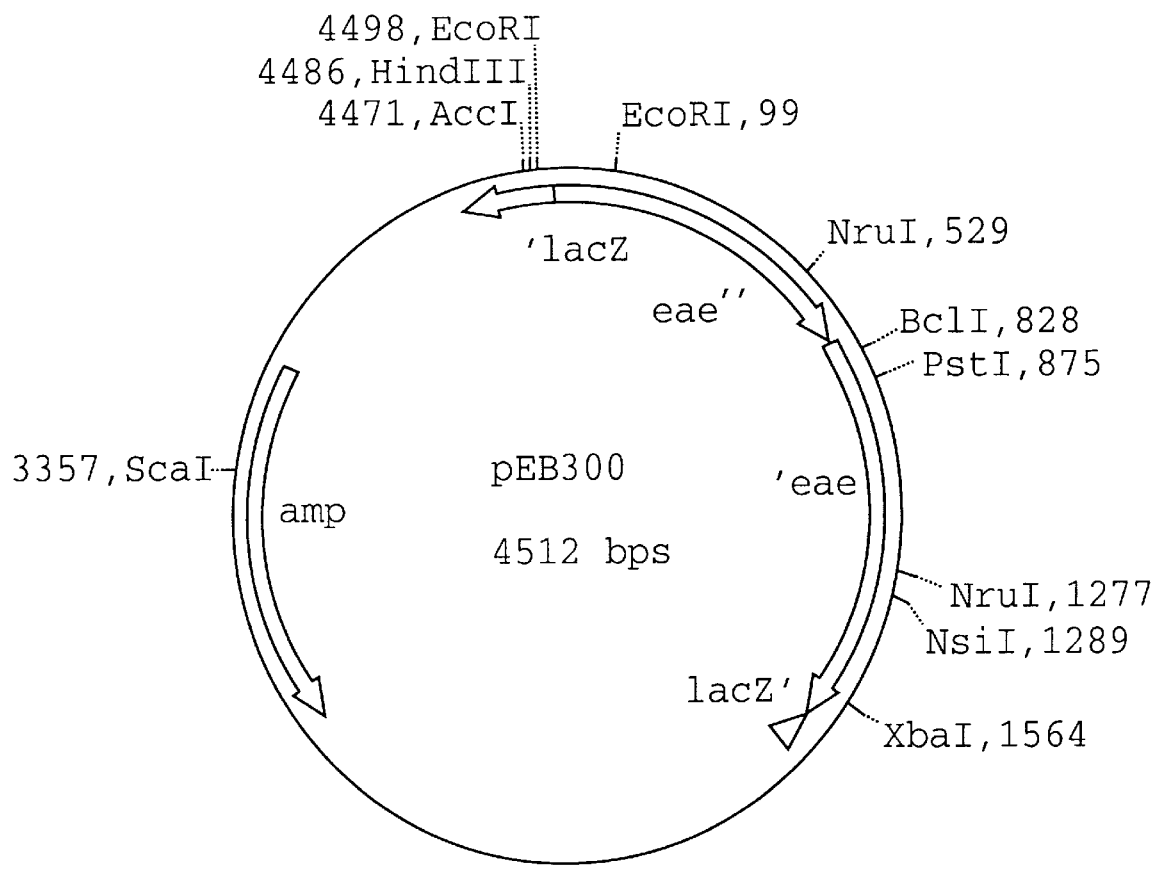

Plasmid pEB290 is transformed into *E. coli* strain GM119 [dam-6, dcm-3, [Arraj], J. A. and Marinus, M. G. J. Bacteriol. 153:562–565 (1983)] to obtain unmethylated DNA which is sensitive to the restriction endonuclease BclI. Plasmid DNA is isolated (Maniatis, et al., Molecular cloning: a laboratory manual. Cold Spring Harbor (1982)) and restricted with BclI to remove an internal 1125 bp fragment from the gene. The resulting sticky ends are ligated to each other to create pEB300 (FIG. 15).

Figure 16:
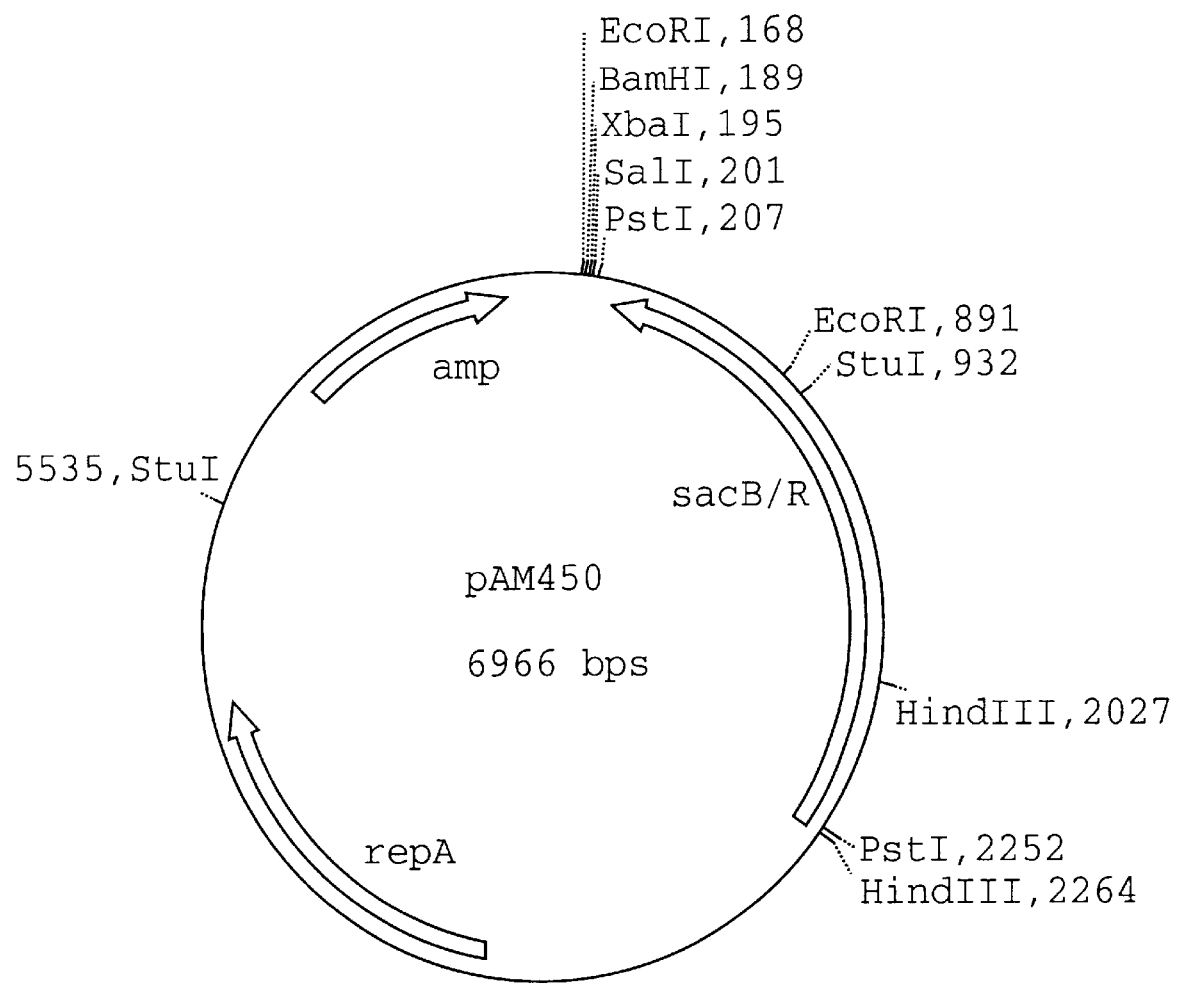
Figure 17:
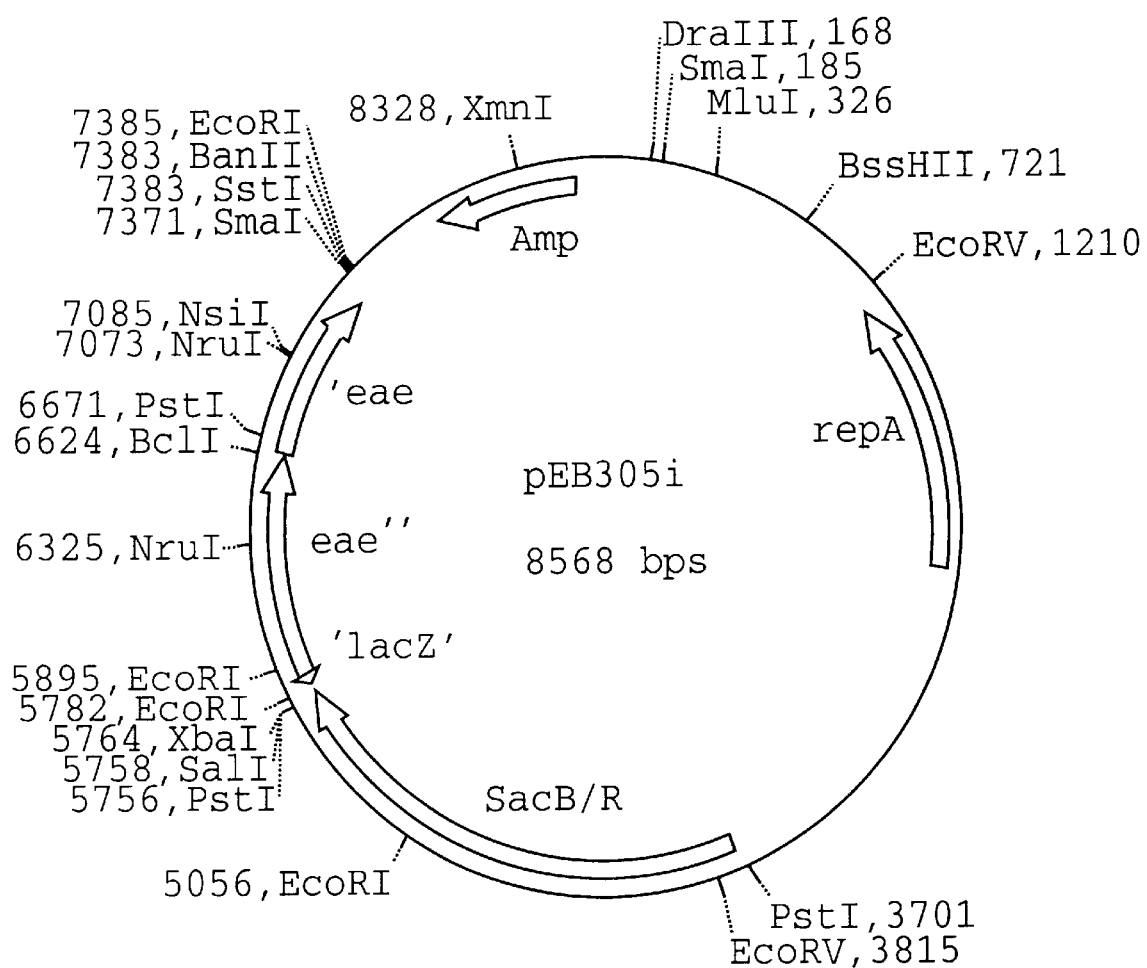

The deleted eae gene is excised by digesting pEB300 with XbaI and HindIII, and the fragment containing the eae sequence is ligated into the BamHI site of the suicide vector, pAM450 (FIG. 16) to form pEB305. Plasmid pAM450 is a derivative of pMAK705 (Hamilton et al., J. Bacteriol., 171:4617–4622 (1989)) with three features. First, it has a temperature sensitive (ts) origin of replication. Second, the plasmid carries the sacB/R locus from *Bacillus subtilis*, rendering the host strain sensitive to sucrose (Gay et al., J. Bacteriol 164:918–921 (1985)); Lepesant et al., Marburg. Mol. Gen. Genet. 118:135–160 (1972)). Third, the plasmid encodes ampicillin resistance. These features allow homologous recombination and positive selection for a second recombination event resulting in resolution and loss of vector sequences. The insertion of the deleted eae gene (from pEB300) into the suicide vector (pAM450) results in the plasmid called pEB305 (FIG. 17).

The suicide:eae construct, pEB305, is transformed into wild type EHEC strain 86-24 by electroporation (Sizemore, et al., Microb. Pathog. 10:493–499 (1991)). Double recombinants that have been cured of the vector sequences are selected by growth on medium containing sucrose and then screened for ampicillin sensitivity (Blomfield et al., Mol. Microbiol., 5:1447–1457 (1991)). Transformants that have been cured of the suicide vector sequences are sucrose resistant, ampicillin sensitive, and able to grow equally well at 30° and 42° C. Deletion of the chromosomal eae sequences is confirmed by: (i) the reduced size of the eae fragment after PCR amplification with primers MM1 and MM2; (ii) Southern blot analysis of the mutated chromosomal DNA; (iii) loss of restriction sites within the deleted region of the eae gene; and (iv) the inability of an internal probe to recognize the mutated chromosome.

The resulting in-frame deletion mutant of EHEC strain 86-24 strain is designated 86-24eaeΔ10. The mutation is confirmed to be in frame by in vitro transcription and translation analysis of the PCR-derived product from 86-24eaeΔ10. A truncated protein product of the predicted size, about 68,000 Da, is identified by [$^{35}$S] methionine labeling of the translation product. The eae mutant strain is identical to wild type 86-24 in all characteristics, including: growth in LB broth, agglutination with 0157 and H7 antisera, inability to ferment sorbitol, and growth on Mac-Conkey agar at 37° C.

Those of ordinary skill in the art will recognize that other methods of creating strains of EHEC that are mutated in eae and do not retain binding ability are possible and may be substituted.

C. The Role of eae in EHEC Adherence in Vitro.

The isogenic strains, 86-24, 86-24eaeΔ10 and 86-24eaeΔ10 carrying pEB310 are tested for adherence to HEp-2 and HCT-8 cells. Wild type 86-24 forms microcolonies when the bacteria interact with HEp-2 or HCT-8 cells. M. L. McKee & A. D. O'Brien, Infection & Immunity 63:2070 (1995). This localized adherence is FAS (fluorescence actin staining) positive which indicates the polymerization of F-actin at the site of bacterial attachment (i.e., the expected result). The mutant 86-24eaeΔ10 is unable to adhere to HEp-2 cells. When eae is introduced into 86-24eaeΔ10 on either pEB310 or pEB311, the LA/FAS (LA=localized adherence or microcolony formation) phenotype is fully restored, an observation which demonstrates that intimin alone complements the eae mutation. Since both of the clones complement the eae mutant, the native promoter for eae is present in the PCR amplified sequences.

D. Effect of Adding Exogenous His-intimin Fusion Proteins

The adherence assay also may be used to evaluate the effect of exogenously added His-intimin fusion proteins on the binding capability of 86-24eaeΔ10 and the binding capability of wild-type strain 86-24. In this case, the purified His-intimin fusion proteins are added to the epithelial cell monolayers before addition of bacteria as indicated in each experiment.

HEp-2 cells are incubated with 20 μg–20 μg of RIHisEae for 30 minutes prior to the addition of 86-24 to the monolayer. The infected monolayers are then washed extensively, stained with FITC-phalloidin, and observed microscopically. The fusions enhance binding wild type strain of 86-24 to HEp-2 cells. The size of the 86-24 microcolony as well as the total number of HEp-2 cells with adherent microcolonies increases as the concentration of RIHisEae increases. At high doses (20 μg), the fusion protein causes the HEp-2 cells to show aberrant appendages and processes. For this reason, 1–2 μg is the most preferred dose for further studies.

When added exogenously to HEp-2 cells, RIHisEae complements the HEp-2-cell binding defect (or restores binding capability) of 86-24eaeΔ10. The shorter fusion protein, RVHdHisEae, also complements for adherence. A similar amino terminal fusion of histidine residues to mouse dihydrofolate reductase (His-DHFR) does not enhance the adherence of 86-24. Moreover, the plasmids that encode the intimin fusion proteins, pEB312 and pEB313, are able to complement 86-24eaeΔ10 for attachment in vitro. Thus, such studies indicate that the proteins encoded by pEB312 and pEB313 are sufficient to confer adherence.

As noted above in Example I, the fusion proteins localize to the insoluble pellet fraction after sonic disruption of the host strains, indicating that these proteins are localized to the membrane. Plasmid pQE16, which encodes the His-DHFR fusion, does not complement 86-24eaeΔ10 (data not shown). That the irrelevant protein fusion with the histidine residues does not confer HEp-2 cell adherence on the eae mutant indicates that the histidine residues added to intimin are not responsible for the activity observed for the exogenously added His-intimin fusions. The enhancement or complementation of EHEC binding to HEp-2 cells observable with exogenous RIHisEae and RVHdHisEae indicates that intimin interacts with both the bacteria and the epithelial cell.

EXAMPLE V

The Role of eae in vivo—Gnotobiotic Piglet Infection Model

The role of intimin in intestinal colonization, A/E lesion formation, and EHEC-mediated colitis and diarrhea in the gnotobiotic piglet is evaluated by the method of Francis, et al. (Francis et al.,Infect. Immun., 51:953–956 (1986)). Both pairs of piglets inoculated with the wild-type parent strain, 86-24 develop diarrhea and have edema in the mesentery of the spiral colon at necropsy.

Histologically, strain 86-24 primarily colonizes the cecum and spiral colon. Histologically and by culture, no evidence of bacterial dissemination to the liver, kidney, lung, or brain is detected. Intimate bacterial adherence and A/E lesions, as described by Staley (Staley et al., Vet. Pathol. 56:371–392 (1969)) and Moon (Moon et al., Infect. Immun., 41:1340–1351 (1983)) for EPEC, are evident by both light and election microscopy examination of cecum and colon of piglets infected with 86-24. A/E lesions include the accumulation of electron-dense material at the site of attachment. In some areas, sloughed enterocyte fragments and microvilli with attached bacteria are noted in the gut lumen. In histologic sections of the cecum and spiral colon of piglets infected with 86-24 , an inflammatory infiltrate is seen. Inflammation is characterized by scattered neutrophils in the lamina propria and mild diffuse accumulation of serous fluid and perivascular lymphocytes and macrophages in the submucosa.

Both piglets inoculated with the mutant strain, 86-24eaeΔ10 have formed feces at necropsy. Histologically and by EM examination, there is no evidence that strain 86-24eaeΔ10 is able to colonize piglet intestine and cause the A/E lesion. The few bacteria seen by light and EM examination are in the mucus overlying the mucosal epithelium of the cecum and spiral colon. One of two piglets inoculated with 86-24eaeΔ10 has slight mesocolonic edema, but no other gross or microscopic lesions are seen in either piglet.

Piglets inoculated with 86-24eaeΔ10(pEB310) have pasty feces and mesocolonic edema at necropsy. Strain 86-24eaeΔ10(pEB310) intimately adheres to mucosal enterocytes and causes A/E lesions in the cecum and spiral colon. Histologically, perivascular lymphohistiocytic typhlocolitis, similar to that caused by wild type 86-24 is also seen.

Similar experiments are conducted in a colostrum-deprived newborn calf model, showing that intimin is necessary to provoke A/E lesions in the gut as well as to evoke *E. coli* O 0157:H7 strain 86-24-mediated diarrhea. (A. D. O'Brien, M. R. Wachtel, M. L. McKee, H. W. Moon, B. T. Bosworth, C. Neal Stewart, Jr., and E. A. Dean-Nystrom. "Intimin: Candidate for an *Escherichia coli* O157:H7 Anti-Transmission Vaccine". Abstract of the 32nd Joint Conference on Cholera and Related Diarrheal Diseases, Nagasaki, Japan, Nov. 14–16, 1996, the disclosure of which is incorporated herein by reference.) These experiments also demonstrate that by 2 days post-infection the numbers of infecting organisms in the lower bowel are significantly less in the animals fed the eae mutant or a non-pathogenic *E. coli* strain than in the calves fed the wild type or the eae mutant with the complementing clone.

EXAMPLE VI

Recognition of EHEC Proteins by HC Patient Sera.

Convalescent immune sera tested from hemorrhagic colitis patients (kindly provided by T. Barrett at the Centers for Disease Control and Prevention, Atlanta, Ga.) react with $P_{T7}$-expressed intimin preparations (i.e., his-intimin expressed by pEB310 and pEB311) in a Western immunoblot. To decrease reactivity of the hemorrhagic colitis patients' sera with *E. coli* proteins in the expression system, sera samples are adsorbed with whole cell extracts of DH5α transformed with pGP1-2 and pBRKS⁻ (the expression vector). After adsorption, the normal sera controls recognize only proteins in the ammonium sulfate concentrated fraction of the intimin preparations but no longer react with proteins expressed from pEB310 or the vector control. After adsorption, the HC patient sera still recognize many *E. coli* proteins, but the reaction with intimin remains strong.

EXAMPLE VII

Administration of His-intimin to Patients

The following example provides the administration of his-intimin to patients in order to stimulate a protective immune response. A protective immune response is one that elicits sufficient antibody to permit a patient to avoid infection, decrease the significance or severity of an infection, or decrease the ability of bacteria to colonize the gastrointestinal tract.

Methods of administration of his-intimin include, but are not limited to, injection (including, but not limited to, intraperitoneal, intravenous, subcutaneous, and intramuscular) of his-intimin directly into the patient to elicit an immune response, ingestion or by gavage of his-intimin alone or with food, and intra-nasal inoculation with his-intimin, which promotes binding of intimin to receptors of epithelial cells in the naso-pharynx.

When the his-intimin is ingested, the protein is contained within a gel capsule, liposome, or attached to an inert substance to aid in passage of the inoculum through the stomach. As the fusion protein is acid stable, it also is ingested by itself or may be mixed into a food product. A preferred method of administration is in a fusion protein of his-intimin and SLT (Shiga-like toxin). A his-intimin-SLT fusion protein is bound to SYNSORB (SynSorb Biotech, Inc., 1204 Kensington Rd, N. W., Calgary, Alberta, Canada, T2N3P5), which has a receptor for SLT, via the SLT-receptor interaction. The SYNSORB construct is mixed with chocolate pudding and fed to children.

Purified RiHisEae (His-tagged Eae, 900/935 amino acids), as well as the third third portion of intimin (encoded by pMW103), are stable after incubation at pH 2.0 at 37° C. for 24 hr. This indicates that a His-Eae fusion can pass through the stomach unharmed or undegraded. Moreover, in nature Eae is expressed on the outer membrane of the bacterium and it still promotes intimate adherence after passing through the stomach, indicating its resistance to acidic environments.

Ingestion or intra-nasal inoculation stimulates local immunity, which thwarts future colonization by EHEC and EPEC. Cross-immunity through homology is stimulated to *Hafnia alvei* and *Citrobacter rodentium*, Yersinia sp. and other bacterial species having intimin-like proteins. Although it is not necessary to quantitate the degree of cross-immunity conferred by administration of intimin in order to benefit from a protective immune response to infection by bacteria other than EHEC that express intimin-related proteins, an assay for such protection is described in Example IX. The assay permits assessment of the efficacy of intimin antibodies on blocking interaction with epithelial cells by pathogens known to have intimin-like binding proteins.

In another embodiment, injection of his-intimin into cow udders leads to an immune response in the cow. Antibodies against the protein are present in the cow's milk. Calves that drink the milk are passively immunized until they can be actively immunized by the method of choice. Alternatively, his-intimin may be fed to cows or introduced into the cow's feed. The presence of his-intimin introduced in this way also stimulates an antibody response in the cows so that antibodies are produced and appear in the cows' milk.

Another embodiment involves the administration of nucleic acid vaccines. His-intimin is injected into a patient as naked eae DNA, or the DNA is delivered to the body by a carrier system such as retroviruses, adenoviruses, or other carriers known in the art. Following administration, the patient mounts an immune response against transiently expressed foreign antigens.

Currently nucleic acid vaccines, in general, are nearing clinical trials. This approach to vaccines involves delivering the DNA encoding the desired antigen into the host by inserting the gene into a nonreplicating plasmid vector (Marwick, C. JAMA 273:1403 (1995); reviewed in Vogel, F. R. and N. Sarver. Clin. Microbiol. Rev. 8:406 (1995)).

The first published demonstration of the protective efficacy of such a vaccine has shown that intramuscular injection of plasmid DNA encoding influenza A virus (A/PR/8/34) nucleoprotein (NP) elicited protective immune responses in BALB/c mice against a heterologous strain of influenza virus (A/HK/68) (Ulmer, J. B. et al. Science 259:1745 (1993)). Immunized animals had reduced virus titers in their lungs, decreased weight loss, and increased survival compared with challenged control mice. Both NP-specific cytotoxic T lymphocytes (CTL's ) and NP antibodies were generated. The NP antibodies were ineffective at conferring protection, but the CTL's killed virus-infected cells and cells pulsed with the appropriated major histocompatibility complex class I-restricted peptide epitope.

Another study has shown that intramuscular injection of plasmid DNA encoding influenza virus A/PR/8134 hemagglutinin resulted in the generation of neutralizing antibodies that protected mice against a heterologous lethal influenza virus challenge (Montgomery, D. L. et al. DNA Cell Biol. 12:777 (1993)).

Practice of the invention by this method can be accomplished by reference to the aforementioned articles incorporated herein by reference, in particular Montgomery, D. L. et al. DNA Cell Biol. 12:777 (1993). The eae locus is described in FIG. 5 according to restriction sites and according to its sequence in FIG. 3, for strain CL8, and its sequence in strain 933, shown in FIG. 4.

EXAMPLE VIII

A. Conjugation of Antigens from Various Pathogens to His-intimin to Elicit an Immune Response Against Both Eae and the Conjugated Antigen.

Antigens (Ag) and haptens from various pathogens are conjugated to a histidine-tagged intimin molecule. This fusion protein is used as an inoculum with intimin acting as the carrier to target binding to intestinal epithelial cells. This conjugate protein can be designed in any of the following configurations: N-His-intimin-Ag-C, N-Ag-intimin-His-C, N-His-Ag-intimin-C, N-intimin-Ag-His-C, N-intimin-His-Ag-C, or N-Ag-His-intimin-C.

The size of intimin varies with the size of the antigen that is to be fused, and the number of antigens to which the intimin is fused as would be recognized by those in the art. The variables to be considered in the design of such a fusion protein are: (1) foreign antigen; (2) size of intimin used, which can be of whatever size that retains binding function as described above; (3) fusion order N→C; and (4) method of conjugation, such as genetic, as in cloning and expressing a fusion protein, and chemical, although additional methods are readily apparent to those ordinarily skilled in the art. (D. V. Goeddel, "Systems for Heterologous Gene Expression," Meth. Enzymol., Vol. 185, Academic Press, New York, 1990.; K. Itakura, "Expression in *E. coli* of a chemically synthesized gene for the hormone somatostatin," Science, 198: 1056–1063 (1977); and D. V. Goeddel et al., "Expression of chemically synthesized genes for human insulin," Proc. Natl. Acad. Sci. USA, 281: 544–548 (1979)).

Delivery of this coupled antigen occurs using the same mechanisms as that of a histidine-tagged intimin alone, as set forth above in Example VII.

Haptens and antigens may derive from but are not limited to bacteria, rickettsiae, fungi, viruses, parasites, drugs, or chemicals. They may include, for example, small molecules such as peptides, oligosaccharides, and toxins. Certain anti-microbial drugs, chemotherapeutic drugs having the capacity of being absorbed on the mucosal surface may also be coupled to intimin. The antigens and polysaccharides that may be coupled to intimin and administered to stimulate a protective immune response may include those shown below in Table 1.

TABLE 1

| Antigens and/or polysaccharides from: |
|---|
| *Bordetella pertussis* |
| *Borellia burgdorferi* |
| Campylobacter sp., including *C. jejuni* |
| *Candida albicans*, other Candida |
| *Chlamydi trachomatis* and *pneumoniae* (TWAR) |
| *Citrobacter rodentium* |
| Clostridium sp., including *C. botulinum, C. difficile, C. perfringens, C. tetani*, (including tetanus toxoid vaccine) |
| Coronaviruses |
| *Corynebacterium diphtheriae*, including diptheria toxoid vaccine |
| *Cryptococcus neoformans* |
| *Entamoeba histolytica* |
| *Escherichia coli* sp. including |
| ETEC (enterotoxigenic *E. coli*), |
| EAggEC (enteroaggregative *E. coli*), |
| EPEC (enteropathogenic *E. coli*), |
| EHEC (enterohemmorhagic *E. coli*), EHEC SLT subunits or toxoid |
| EIEC (enteroinvasive *E. coli*), |
| UPEC (uropathogenic *E. coli*), including *E. coli* endotoxin, |
| J5 antigen (LPS, Lipid A, Gentabiose), |
| O polysaccharides (serotype specific) |
| EHEC |
| *Haemophilus influenza*, including *H. influenza* type b (polyribose phosphate) |
| *Hafnia alvei* |
| *Helicobacter pylori* |
| Hepatitis A, B, A, and others |
| Human immunodeficiency virus I and II (GP120, GP41, GP160, p24, and others) |

TABLE 1-continued

| Antigens and/or polysaccharides from: |
|---|
| *Histoplasma capsulatum* |
| Klebsiella species, including polysaccharides (serotype specific) |
| Legionella species, including *L. micdadei, L. pneumophila* |
| *Listeria monocytogenes* |
| Mycobacterium species, including *M. avium, M. kansasii, M. tuberculosis* |
| Mycoplasma |
| Neisseda species, including *N. gonorrhoeae, N. meningitidis* (including serotype specific or protein antigens) |
| *Nocardia asteroides* |
| Plasmodium species |
| *Pneumocystis carinii* |
| Polio virus |
| *Pseudomonas aeruginosa*, including serotype specific polysaccharides |
| Rabies virus |
| Rhinovirus |
| Rickettsia |
| Rotavirus |
| Salmonella sp., including *S. cholerasuis, S. enteriditis, S. typhi, S. typhimurium* |
| Shigella species, including *S. flexneri, S. sonnei, S. boydii, S. dysenteriae* |
| Staphylococcus sp., including *S. aureus*, polysaccharides from types 5 and 8 (serotype specific and common protective antigens), *S. epidermidis*, serotype polysaccharide I, II, and III (and common protective antigens) |
| Streptococcus species, all serotypes including *S. pneumoniae* (all serotypes), *S. pyogenes*, including group A, group B (serotypes Ia, Ib, II, and III) |
| *Treponema pallidum* |
| *Varicella zoster* |
| *Vibrio cholerae* |
| Yersinia species, including *Y. pestis, Y. pseudotuberculosis, Y. enterocolitica* |

The sizes of his-intimin that may be conjugated to antigens appearing in Table 1 include RIHisEae (900/935 aa, EcoRI-HindIII fragment of pEB313) and RVHindHis (604/935 aa, EcoRV-HindIII fragment of pEB313), as set forth above in Example I. Those of ordinary skill in the art will recognize that additional fragments of varying lengths having adherence activity may be selected within the spirit and scope of the invention. The efficacy of the fragments considered for selection may be assessed according to the procedures described in Example IV.

B. Construction of a Plasmid Expressing N-His-IcsA-intimin-C.

*Shigella flexneri* causes bacillary dysentery in humans by invading epithelial cells of the colonic mucosa (Labrec et al. J. Becteriol. 88:1503–1518, (1964)). A 120 kDa outer membrane protein, called IcsA, is necessary for intra- and intercellular spread of this organism (Bernardini et al. Proc. Natl. Acad. Sci. USA.86:3867–3871, (1989); Lett et al. J. Bacteriol. 171:353–359, (1989)). An iscA mutant (SC560) was reasonably well tolerated by orally infected macaque monkeys and elicited protection against homologous challenge (Sansonetti et al. Vaccine 9:416–422, 1991).

The following protocol may be used (FIG. 18):

Transform pEB313 into a $dam^-$ host, such as DM1 (Gibco BRL, P.O. Box 68, Grand Island, N.Y. 14072, 1-800-828-6686). Digest pEB313/ClaI/HindIII, isolate 1796 bp fragment (this fragment encodes the last 547 amino acids of intimin). Ligate into pBluescriptSK+/ClaI/HindIII (pBluescriptSK+available from Stratagene, 11011 N. Torrey Pines Rd., La Jolla, Calif. 92037, 1-800-424-5444). Call this plasmid pEae1. Digest pHS3192 with AvaI, fill in the end with Klenow fragment, digest with ClaI, isolate 2490 bp fragment [this fragment encodes 2923 bp or 974 aa's from base pair #706–3629; the ORF of icsA spans from bp#574-3880, this is 3306 bp and encodes 1102 aa's; reference for sequence of icsA is Lett et al., J. Bacteriol. 171:353 (1989)]

(pHS3192 available from P. Sansonetti (ref Bernardini, M. L. et al. Proc. Natl. Acad. Sci. USA. 86:3876 (1989)). Ligate the 2490 bp fragment into pEae1digested with ClaI and HincII, producing a plasmid called pEae2. Using these restriction enzymes, the reading frames of icsA and eae remain in frame. Digest pEae2 with XhoI and HindIII, isolate the 4286 bp fragment; ligate into pQE 32 (QIAGEN) digested with SmaI and HindIII. This ligation will maintain the proper reading frame of both genes with the promoter. The resulting plasmid is called picsA-Eae.

Alternatively, one could fuse two genes in frame by cloning with PCR, followed by ligation into the appropriate pQE vector. This technique is well known to those of ordinary skill in the art.

C. Preparation of a Conjugate Vaccine Using His-intimin as the Protein Carrier.

While any polysaccharide could be used, in this vaccine the capsular Vi polysaccharide of *Salmonella typhi* is used. Purify His-intimin as in Example II; this would be conjugated to Vi (purified from *S. typhi* according to established procedures (Szu et al. J. Exp. Med. 166:1510 (1987)). The conjugation will proceed using standard protein-polysaccharide conjugation technology well known to those in the art. Methods of conjugation are well known to those of ordinary skill in the art, and include the heteroligation techniques of Brunswick, M. et al., J. Immunol. 140:3364, 1988. See also Chemistry of Protein conjugates and Crosslinking CRC Press, Boston (1991).

Techniques to conjugate moieties to primary or secondary carriers are well known to those skilled in the art, and include, in part, coupling through available functional groups (such as amino, carboxyl, thio and aldehyde groups). See S. S. Wong, Chemistry of Protein Conjugate and Crosslinking CRC Press (1991); and Brenkeley et al. Brief Survey of Methods for Preparing Protein Conjugates With Dyes, Haptens and Cross-linking Agents, Bioconjugate Chemistry 3 #1 (January 1992).

A vaccine such as that described in this example would provide a prevention of diarrheal pathogens to include both those organisms that express intimin (or intimin-like proteins), as well a diarrheal pathogen that expresses Vi.

Any combination of intimin plus other antigens from other diarrheal pathogens can be combined. In addition, if polysaccharides were used from organisms that produce other diseases, such as pneumococcal polysaccharides, the intimin-polysaccharide vaccine would be useful for prevention of multiple diseases. Delivery of a vaccine against respiratory pathogens will preferentially be done directly to the respiratory tract; ingested pathogens through ingestion.

EXAMPLE IX

Generation and Testing of Adherence-blocking Anti-intimin Antibodies: Polyclonal and Monoclonal High titer polyclonal anti-intimin antisera are elicited upon intraperitoneal injection of RIHisEae into mice, rabbits, and goats. Testing of antibody titer and an antibody effectiveness assay are shown. The generation of monoclonal antibodies is also described.

A. Generation of Polyclonal Antibodies

Various techniques can be used to prepare antibodies against full-length intimin or various portions thereof in various animals. Several of these techniques are described below. As would be recognized by one skilled in the are, polyclonal antibodies can be generated from intimin and portions of intimin that are not his-tagged and from intimin-like proteins and portions thereof.

1. Generation of Mouse Anti-RIHisEae Polyclonal Antibodies

The technique of Harlow, E. and D. Lane (eds) *Antibodies—a Laboratory Manual.* Cold Spring Harbor, N.Y. (1988) may be followed. The general procedure is outlined herein. Take pre-bleeds of each mouse to be immunized: Bleed from the tail vein into an eppendorf tube. Incubate at 37° C. for 30 min, stir gently with a sterile toothpick (to loosen the clot), store overnight at 4° C. In the morning, spin 10 min/10,000 rpm in the microfuge, and collect the serum (i.e., supernatant; red blood cells are the pellet). Store the serum at −20° C. The sera obtained will be used as a negative control after the mice are immunized.

Inject a BALB/c mouse intraperitoneally with 25 $\mu$g of RIHisEae (using TITERMAX® an adjuvant such as Freund's complete adjuvant, according to the instructions of the manufacturer (CytRx Corp., 154 Technology Pkwy., Norcross, Ga. 30092, 800-345-2987). Wait 2 weeks, boost with an identical shot, wait 7 days and bleed from the tail vein into an eppendorf tube. Incubate at 37° C. for 30 min, stir gently with a sterile toothpick (to loosen the clot), store overnight at 4° C. In the morning, spin 10 min/10,000 rpm in the microfuge, and collect the serum. Store the sera at −20° C.

2. Generation of Mouse anti-third third portion of Intimin polyclonal sera:

Mice are prebled by the tail vein as described above in Example IX, part A. The third third portion of intimin is enriched and dialyzed as described above in Example II. Mice are injected with the third third portion of intimin mixed with TitreMax adjuvant, as described in Example IX, part A. After 3 boosts, mice are bled via the retro-orbital sinus, and sera prepared in described Example IX, part A. Sera is tested by Western blot analysis, as described for the goat polyclonal sera in section 4 below. Sera is assayed for the capacity to block EHEC adherence to HEp-2 cells as described above in Example IX, part C.

3. Generation of Rabbit polyclonal anti-Intimin antibodies

Rabbit polyclonal sera is generated against the (1) first third, (2) second third, and (3) third third portions of intimin. Each specific sera is separately assayed in HEp-2 adherence assays for the capacity to block adherence of EHEC to HEp-2 cells.

Preparation of First Third Portion of Intimin for Rabbit Immunization

Clone pMW101 is transformed into strain DH5$\alpha$F'lacI$^Q$. Induction of protein expression and purification of the His-tagged intimin fragment over the Ni-NTA affinity resin is performed as described in the Qiagen manual that accompanies their QlAexpressionist Ni-NTA resin purification kit (Qiagen Inc., Chatsworth, Calif.). Eluted fractions are monitored for protein content by $A_{280}$ and by Bradford analysis, using a dye reagent from Bio-Rad (Hercules, Calif.). Peak fractions eluted from the Ni-NTA column (with 250 mM imidazole) are electrophoresed on 15% polyacrylamide gels with SDS for analysis and purification. To visualize the proteins on the gels for analysis, both silver (Bio-Rad) and Coomassie Blue G-250 (Sigma) staining are used.

To purify the protein for immunization of animals to obtain antisera, the peak column fractions are run on preparative SDS polyacrylamide gels, and proteins are visualized with Copper stain (Bio-Rad). The band of protein corresponding to the intimin fragment is excised from the gel with a clean razor blade, and the gel slice is destained according to the instructions provided with the Copper stain reagent. Protein is then eluted from the gel slice using an Electro-Eluter Model 422 (Bio-Rad) according to the manufacturer's instructions. The protein is then concentrated using a Centricon-10 concentrator from Amicon (Beverly, Mass.). The majority of the SDS in the eluted protein sample is removed by one of two methods. The first method involves addition of phosphate-buffered saline (PBS) to the protein sample, which causes precipitation of SDS. The majority of the protein does not precipitate, and the precipitate is not analyzed to determine what ions may also have precipitated. The SDS is pelleted by centrifugation; and the supernatant, which contains most of the protein and possibly some residual SDS, is removed and concentrated using a Centricon-10 concentrator from Amicon (Beverly, Mass.).

The second method for removal of SDS involves preparing a column of Extracti-Gel$^R$D Detergent Removing Gel, purchased from Pierce (Rockford, Ill.). The Extracti-Gel$^R$D Detergent Removing Gel is used according to the instructions of the manufacturer. The purified protein is concentrated as described above. Protein concentrations are determined by Bradford analysis using dye reagent purchased from Bio-Rad and also by running different volumes of purified protein on a gel adjacent to aliquots of varying amounts of the original column fractions to compare the amounts of proteins visually. Fractions of this purified protein are analyzed by SDS-PAGE using both silver and Coomassie staining.

Preparation of Second Third Portion of Intimin for Rabbit Immunization

Purification of the His-tagged middle third fragment of the intimin protein expressed from clone pMW102 is performed with the same methods used for the N-terminal third, with the following instructions. SDS-AGE analysis is done using 12.5% acrylamide gels. For gel-purification of the protein and electrolution, most of the preparative gels are stained with Copper stain as above; and one gel was stained with Coomassie brilliant blue dissolved in water as described in Harlow, E. and D. Lane (eds.) *Antibodies—a Laboratory Manual*. Cold Spring Harbor, N.Y. (1988). Much of the SDS in the electroeluted protein fractions is precipitated out by addition of PBS buffer. For concentration of the protein, Amicon Centricon-30 concentrators are used (Amicon).

Preparation of Third Third Portion of Intimin for Rabbit Immunization

The third third intimin protein is enriched and dialyzed as described above in Example II. One mg of protein is run by SDS-PAGE on four BioRad MiniProtean II gels. Protein is negatively stained with copper stain (BioRad, cat # 161–0470, Richmond, Calif.) according to the instructions of the manufacturer as follows: the gel is rinsed in dH$_2$O for 45 seconds, stained in 1× copper stain for 5 minutes, and rinsed in dH$_2$O for 3 minutes. The gel is visualized against a black background, and the ~37 kDa protein band is cut form the gel with a razor. Purified gel slices are then de-stained in buffer (25 mM Tris base, 192 mM glycine, 3×/10 min), wrapped in plastic wrap and stored at −20° C. prior to immunization Immunization of Rabbits New Zealand white female rabbits (5 to 6 lbs) are immunized separately with the antigens prepared as described above according to a schedule that could be readily determined by one skilled in the art. An example of such a schedule is as follows:

| DAY | PROCEDURE |
|-----|-----------|
| 0 | Prebleed/initial Inoculation, 100 µg Ag mixed with complete Freund's adjuvant |
| 14 | Boost, 50 µg mixed with incomplete Freund's adjuvant |
| 21 | Boost, 50 µg mixed with incomplete Freund's adjuvant |
| 35 | Test Bleed |
| 45 | Boost, 50 µg mixed with incomplete Freund's adjuvant |
| 56 | Test Bleed |

The route of injection can be subcutaneous and/or intermuscular at multiple sites. Sera derived from test bleeds is tested for specific recognition of the antigen by Western Blot analysis, as described for the goat polyclonal sera in section 4 below. When high titer recognition of the antigen is achieved, as recognizable by one skilled in the art, the rabbit is exsanguinated to recover the antibodies. The large volume sample of blood is verified for specific recognition of the antigen by Western Blot analysis.

Affinity Purification of Rabbit Anti-intimin Polyclonal Sera by Western Blot

Rabbit anti-intimin polyclonal sera is affinity purified to remove cross-reacting antibodies not specific for intimin or intimin-like proteins from the sera. (Harlowe, E. and D. Lane (eds) *Antibodies—a Laboratory Manual*. Cold Spring Harbor, N.Y. (1988), p. 498 or S. H. Lillie and S. S. Brown. Yeast. 3:63 (1987)). RIHisEae (0.250 mg) is electrophoresed by SDS-PAGE (size: BioRad MiniProtean II minigel, BioRad, Richmond, Calif.), transferred to nitrocelullose, and stained with Ponceau S (Sigma, St. Louis, Mo.). A strip of nitrocellulose containing the full length His-intimin band (about 100 kDa) is excised with a razor, and the nitrocellulose strip containing the protein is incubated overnight at 4° C. in 2% milk/TBS-0.2% Tween, shaking gently. The nitrocellulose strip is washed briefly in TBS-Tween, and placed in a container on top of a piece of Parafilm (American National Can, Greenwich, Conn.). Rabbit sera is pipetted onto the mini-Western blot (as much volume as will fit, about 400–500 µl), and wet paper towels are placed over the containing, not touching the nitrocellulose strip, followed by plastic wrap. The blot is shaken gently for 5 hours, after which the sera (now called "depleted sera") is removed and saved for analysis. The strip is washed 3 times in PBS for 10 minutes, and glycine buffer (150 mM NaCl, pH 2.3-with HCl) is added (as much volume as will fit onto the strip) for 30 minutes. Affinity purified antibodies are pipetted off, and ¹⁄₁₀ volume Tris-HCl, pH 8.0 is added. Antibodies so recovered are then neutralized with 1 N NaOH and tested by Western blot analysis as described below.

Affinity Purification of Rabbit anti-intimin Polyclonal Sera by Antigen Affinity Column Rabbit anti-intimin polyclonal sera is affinity purified to remove cross-reacting antibodies not specific for intimin from the sera. Antisera raised against intimin or various portions thereof is purified using an antigen affinity column using techniques known to those skilled in the art, such as those described in Harlow, E. and D. Lane (eds.) *Antibodies—a Laboratory Manual*. Cold Spring Harbor, N.Y. (1988).

The antigens (intimin or portions of intimin) are enriched as described above in Example II. Antigens may be further purified by electrophoresis on an acrylamide gel followed by electroelution from a gel slice containing the protein as described below in part 4. Other methods may be substituted for gel-purification and electroelution to further purify the protein after elution from the Ni-NTA resin. These methods may include, but are not limited to, ion-exchange column chromatography and gel filtration chromatography. After purification, the intimin protein may need to be dialyzed into an appropriate buffer for coupling to activated beads to form the affinity resin for antisera purification.

Activated beads appropriate for coupling to the antigen are selected based on several properties: coupling reagent, binding group or matrix, ligand attachment, and stability of the final matrix (as listed in Harlow, E. and D. Lane (eds.) *Antibodies—a Laboratory Manual*. Cold Spring Harbor, N.Y. (1988)). For example, the purified intimin (or portion of intimin) protein antigen is coupled to Affigel beads (Bio-Rad, Richmond, Calif.) according to the instructions of the manufacturer. A column of the activated beads coupled to the antigen is prepared and washed according to instructions of the manufacturer of the beads. The column is then washed according to the method described in Harlow, E. and D. Lane (eds.) *Antibodies—a Laboratory Manual*. Cold Spring Harbor, N.Y. (1988).

Ammonium sulfate precipitation is used to partially purify the sera in preparation for the affinity column. Ammonium sulfate precipitation, resuspension of the protein pellet in PBS, dialysis of the solution versus PBS, and centrifugation to clarify the solution are performed as described in Harlow, E. and D. Lane (eds.) *Antibodies—a Laboratory Manual*. Cold Spring Harbor, N.Y. (1988).

Antisera that has been partially purified by ammonium sulfate precipitation and dialysis versus PBS is passed over the antigen affinity column as described in Harlow, E. and D. Lane (eds.) *Antibodies—a Laboratory Manual*. Cold Spring Harbor, N.Y. (1988). The antisera may be passed over the column multiple times, as this may lead to more complete binding of antibodies to the column. The column is then washed and the affinity-purified antibodies are eluted and dialyzed against PBS as described in Harlow, E. and D. Lane (eds.) *Antibodies—a Laboratory Manual*. Cold Spring Harbor, N.Y. (1988).

Adherence Assays

Affinity purified polyclonal sera is assayed in HEp-2 cell adherence assays for the capacity to block bacterial binding to HEp-2 cells using the method described below in Example IX, part C.

4. Generation of Goat anti-RIHisEae polyclonal antibodies

Pre-bleeds are taken of potential goats to be immunized. Blood is collected from the jugular vein with indirect vacuum. Sera is separated from the whole blood, as described above in Example IX, section A, and tested by ELISA using RIHisEae as the adsorbent (as described in Example IX, section B, below for the ELISA and Example II above for the enrichment of RIHisEae), or by Western blot analysis as described below. The goat chosen for immunization has pre-immune sera with both (a) the lowest recognition of intimin by Western blot analysis and (b) the lowest titer against intimin by ELISA, and does not have the habit of jumping out of the pasture.

Western Blot Analysis of Goat Anti-RIHisEae Polyclonal Sera a. Generation of whole cell lysates Desired strains (for example: 86-24, 86-24eaeΔ10, DH5, M15 pREP4 pEB313) are grown overnight in LB containing the appropriate antibiotics at 37° C., with shaking. Cells (4.5 ml) are pelleted in an eppendorf tube, and 500 µl sonication buffer (50 mM Na-phosphate pH 7.8, 300 mM NaCl) are added. Cells are sonicated in 15 second pulses on ice, aliquoted and frozen at −20° C.

b. Western blot analysis

Whole cell lysates generated as described above (2–5 µl) or purified RIHisEae (2 µl) are run by SDS-PAGE, transferred to nitrocellulose, and used for Western blot analysis of goat sera. The sera (primary antibody) is typically diluted 1:500 or 1:1000 for this purpose. The secondary antibody used is swine anti-goat IgG conjugated to horseradish peroxidase (Boehringer Mannheim, Indianapolis, Ind.), diluted 1:2000. Pre-bleeds of goat sera usually contain several cross-reactive bands that are removed later by affinity purification.

Preparation of Purified RIHisEae (Antigen) for Immunization into Goat

One mg of RIHisEae, generated as described in Example II above, is run by preparative SDS-PAGE. A small analytical lane is stained with Colloidal Coomasie strain (Sigma, St. Louis, Mo.) and used for comparison to the rest of the preparative gel. The high molecular weight full-length intimin band (not stained, running at about 100 kDa) is excised from the preparative gel with a razor, and stored at 4° C. prior to immunization.

Immunization of Goats with Antigen

Female goats (approximately one and a half years old, purebred Saanan or Saanan X LaMANCHA) are immunized separately with the antigens prepared as described above according to a schedule that could be readily determined by one skilled in the art. For example, the goat is given a primary immunization of 500 µg of prepared RIHisEae mixed with Complete Freunds adjuvant. At two week intervals the goat is boosted with 250 µg Ag mixed with incomplete Freunds adjuvant. Test bleeds are begun after the goat has been immunized for a month, and continue until a high anti-intimin titer is reached, as defined by Western blot analysis, described above. When the sera recognizes intimin by Western blot, large blood samples are taken (500 mls, resulting in about 250 mls sera) per session, with two week intervals between large bleeds. Resulting large-volume sera samples are verified for recognition of intimin by Western blot analysis, as described above.

Affinity Purification of Goat anti-intimin Polyclonal Sera by Western Blot

Goat anti-intimin polyclonal sera is affinity purified to remove cross-reacting antibodies not specific for intimin from the sera. (Harlowe, E. and D. Lane (eds) *Antibodies—a Laboratory Manual*. Cold Spring Harbor, N.Y. (1988), p. 498 or S. H. Lillie and S. S. Brown. Yeast. 3:63 (1987)). RIHisEae (0.250 mg) is electrophoresed by SDS-PAGE (size: BioRad MiniProtean II minigel, BioRad, Richmond, Calif.), transferred to nitrocelullose, and stained with Ponceau S (Sigma, St. Louis, Mo.). A strip of nitrocellulose containing the full length His-intimin band (about 100 kDa) is excised with a razor, and the nitrocellulose strip containing the protein is incubated overnight at 4° C. in 2% milk/TBS-0.2% Tween, shaking gently. The nitrocellulose strip is washed briefly in TBS-Tween, and placed in a container on top of a piece of Parafilm (American National Can, Greenwich, Conn.). Goat sera is pipetted onto the mini-Western blot (as much volume as will fit, about 400–500 µl), and wet paper towels are placed over the containing, not touching the nitrocellulose strip, followed by plastic wrap. The blot is shaken gently for 5 hours, after which the sera (now called "depleted sera") is removed and saved for analysis. The strip is washed 3 times in PBS for 10 minutes, and glycine buffer (150 mM NaCl, pH 2.3-with Hcl) is added (as much volume as will fit onto the strip) for 30 minutes. Affinity purified antibodies are pipetted off, and 1/10 volume Tris-HCl, pH 8.0 is added. Antibodies are then neutralized with 1 N NaOH and tested by Western blot analysis as described above.

Affinity Purification of Rabbit Anti-intimin Polyclonal Sera by Antigen Affinity Column Rabbit anti-intimin polyclonal sera is affinity purified to remove cross-reacting antibodies not specific for intimin from the sera. Antisera raised against intimin or various portions thereof is purified using an antigen affinity column using techniques known to those skilled in the art, such as those described in Harlow, E. and D. Lane (eds.) Antibodies—a Laboratory Manual. Cold Spring Harbor, N.Y. (1988).

The antigens (intimin or portions of intimin) are enriched as described above in Example II. Antigens may be further purified by electrophoresis on an acrylamide gel followed by electroelution from a gel slice containing the protein as described below in part 4. Other methods may be substituted for gel-purification and electroelution to further purify the protein after elution from the Ni-NTA resin. These methods may include, but are not limited to, ion-exchange column chromatography and gel filtration chromatography. After purification, the intimin protein may need to be dialyzed into an appropriate buffer for coupling to activated beads to form the affinity resin for antisera purification.

Activated beads appropriate for coupling to the antigen are selected based on several properties: coupling reagent, binding group or matrix, ligand attachment, and stability of the final matrix (as listed in Harlow, E. and D. Lane (eds.) Antibodies—a Laboratory Manual. Cold Spring Harbor, N.Y. (1988)). For example, the purified initimin (or portion of intimin) protein antigen is coupled to Affigel beads (Bio-Rad, Richmond, Calif.) according to the instructions of the manufacturer. A column of the activated beads coupled to the antigen is prepared and washed according to instructions of the manufacturer of the beads. The column is then washed according to the method described in Harlow, E. and D. Lane (eds.) Antibodies—a Laboratory Manual. Cold Spring Harbor, N.Y. (1988).

Ammonium sulfate precipitation is used to partially purify the sera in preparation for the affinity column. Ammonium sulfate precipitation, resuspension of the protein pellet in PBS, and dialysis of the solution versus PBS and centrifugation to clarify the solution is performed as described in Harlow, E. and D. Lane (eds.) Antibodies—a Laboratory Manual. Cold Spring Harbor, N.Y. (1988).

The antisera that has been partially purified by ammonium sulfate precipitation and dialysis versus PBS is passed over the antigen affinity column as described in Harlow, E. and D. Lane (eds.) Antibodies—a Laboratory Manual. Cold Spring Harbor, N.Y. (1988). The antisera may be passed over the column multiple times, as this may lead to more complete binding of antibodies to the column. The column is then washed and the affinity-purified antibodies are eluted and dialyzed against PBS as described in Harlow, E. and D. Lane (eds.) Antibodies—a Laboratory Manual. Cold Spring Harbor, N.Y. (1988).

Adherence Assays

Affinity purified polyclonal sera is assayed in HEp-2 cell adherence assays for the capacity to block bacterial binding to HEp-2 cells using the method described below in Example IX, part C.

B. ELISA to Test Titer of Antibodies

The technique of Harlow, E. and D. Lane (eds) Antibodies—a Laboratory Manual. Cold Spring Harbor, N.Y. (1988) may be followed. The general procedure is outlined below:

(1) bind RIHisEae to plastic microtiter plates at 50 $\mu$g/well in PBS. Incubate 2 h/RT (room temp) or overnight at 4° C.

(2) wash plate 2× with PBS.

(3) block wells with 100 $\mu$l blocking solution [3% bovine serum albumin (Sigma Chemical, St. Louis, Mo.), 0.02% sodium azide (Sigma) in PBS—store stock at 4° C.] for 1–2 h at RT.

(4) wash plate 2× with PBS.

(5) primary Ab=50 $\mu$l test sera diluted in blocking solution for example, start with 1:50 and do eleven 1:2 dilutions, or start with 1:50 and do eleven 1:10 dilutions), incubate 2 h/RT.

(6) wash 4× with PBS.

(7) secondary Ab=goat horseradish-conjugated anti-mouse Ig, affinity purified (Boehringer Mannheim Corp., 9115 Hague Rd., P.O. Box 50414, Indianapolis, Ind. 46250, 800-262-1640). Add secondary Ab diluted 1:500 in blocking solution without azide. Incubate 1 h/RT.

(8) wash 4× with PBS.

(9) add 100 $\mu$l TMB Peroxidase substrate to each well (prepared according to the instructions of the manufacturer, BioRad Labs, 3300 Regatta Blvd., Richmond, Calif. 94804). Allow blue color to develop (no more than 10 min). Stop the reaction with 100 $\mu$l $H_2SO_4$. Read the plate at 450 nm.

A titer is defined as an absorbance value $\geq 0.2$ units above that obtained for mouse pre-immune sera.

Anti-intimin antibodies may be administered to provide passive immune protection to a patient in need thereof. Moreover, anti-intimin antibodies obtained from animals may be used clinically in humans. In such cases, it is preferable to humanize the antibody. Such techniques are well known to those of ordinary skill in the art. G. Winter et al., "Man-made antibodies," Nature, 349: 293–299 (1991); P. T. Jones et al., "Replacing the complementarity-determining regions in a human antibody with those from a mouse," Nature, 321: 522–525 (1986); P. Carter et al., "Humanization of an anti-p185$^{HER2}$ antibody for human cancer therapy," Proc. Natl. Acad. Sci. USA, 89: 4285–4289 (1992). Such antibodies may be given to the sibling of an infected patient to reduce the risk of infection of the sibling.

C. Western Blot Analysis of Anti-RIHisEae Polyclonal Sera

Polyclonal sera is assayed by Western blot analysis to verify recognition of intimin.

1. Generation of whole cell lysates

Desired strains (for example: 86-24, 86-24eae$\Delta$10, DH5$\alpha$, M15 pREP4 pEB313) are grown overnight in LB containing the appropriate antibiotics at 37° C., with shaking. Cells (4.5 ml) are pelleted in an eppendorf tube, and 500 $\mu$l sonication buffer (50 mM Na-phosphate pH 7.8, 300 mM NaCl) are added. Cells are sonicated in 15 second pulses on ice, aliquoted and frozen at −20° C.

2. Western blot analysis

Whole cell lysates generated as described above (2–5 $\mu$l) or purified RIHisEae (2 $\mu$l) are run by SDS-PAGE, transferred to nitrocellulose, and used for Western blot analysis of sera. The sera (primary antibody) is typically diluted 1:500 or 1:1000 for this purpose. The secondary antibody is specific for the animal that is the source of the primary antibody and is conjugated to horseradish peroxidase. Pre-bleeds of sera may contain several cross-reactive bands that are removed later by affinity purification.

D. Affinity Purification of Anti-intimin Polyclonal Sera by Western Blot

Anti-intimin polyclonal sera is affinity purified to remove cross-reacting antibodies not specific for intimin from the sera. (Harlowe, E. and D. Lane (eds) Antibodies—a Laboratory Manual. Cold Spring Harbor, N.Y. (1988), p. 498 or S. H. Lillie and S. S. Brown. Yeast. 3:63 (1987)). RIHisEae (0.250 mg) is electrophoresed by SDS-PAGE (size: BioRad MiniProtean II minigel, BioRad, Richmond, Calif.), transferred to nitrocelullose, and stained with Ponceau S (Sigma, St. Louis, Mo.). A strip of nitrocellulose containing the full length His-intimin band (about 100 kDa) is excised with a razor, and the nitrocellulose strip containing the protein is incubated overnight at 4° C. in 2% milk/TBS-0.2% Tween, shaking gently. The nitrocellulose strip is washed briefly in TBS-Tween, and placed in a container on top of a piece of Parafilm (American National Can, Greenwich, Conn.). Sera is pipetted onto the mini-Western blot (as much volume as will fit, about 400–500 µl), and wet paper towels are placed over the containing, not touching the nitrocellulose strip, followed by plastic wrap. The blot is shaken gently for 5 hours, after which the sera (now called "depleted sera") is removed and saved for analysis. The strip is washed 3 times in PBS for 10 minutes, and glycine buffer (150 mM NaCl, pH 2.3-with Hcl) is added (as much volume as will fit onto the strip) for 30 minutes. Affinity purified antibodies are pipetted off, and ⅟₁₀ volume Tris-HCl, pH 8.0 is added. Antibodies are then neutralized with 1N NaOH and tested by Western blot analysis as described above.

E. Affinity Purification of Anti-intimin Polyclonal Sera by Antigen Affinity Column Rabbit anti-intimin polyclonal sera is affinity purified to remove cross-reacting antibodies not specific for intimin from the sera. Antisera raised against intimin or various portions thereof is purified using an antigen affinity column using techniques known to those skilled in the art, such as those described in Harlow, E. and D. Lane (eds.) *Antibodies—a Laboratory Manual*. Cold Spring Harbor, N.Y. (1988).

The antigens (intimin or portions of intimin) are enriched as described above in Example II. Antigens may be further purified by electrophoresis on an acrylamide gel followed by electroelution from a gel slice containing the protein as described below in part 4. Other methods may be substituted for gel-purification and electroelution to further purify the protein after elution from the Ni-NTA resin. These methods may include, but are not limited to, ion-exchange column chromatography and gel filtration chromatography. After purification, the intimin protein may need to be dialyzed into an appropriate buffer for coupling to activated beads to form the affinity resin for antisera purification.

Activated beads appropriate for coupling to the antigen are selected based on several properties: coupling reagent, binding group or matrix, ligand attachment, and stability of the final matrix (as listed in Harlow, E. and D. Lane (eds.) *Antibodies—a Laboratory Manual*. Cold Spring Harbor, N.Y. (1988)). For example, the purified initimin (or portion of intimin) protein antigen is coupled to Affigel beads (Bio-Rad, Richmond, Calif.) according to the instructions of the manufacturer. A column of the activated beads coupled to the antigen is prepared and washed according to instructions of the manufacturer of the beads. The column is then washed according to the method described in Harlow, E. and D. Lane (eds.) *Antibodies—a Laboratory Manual*. Cold Spring Harbor, N.Y. (1988).

Ammonium sulfate precipitation is used to partially purify the sera in preparation for the affinity column. Ammonium sulfate precipitation, resuspension of the protein pellet in PBS, and dialysis of the solution versus PBS and centrifugation to clarify the solution is performed as described in Harlow, E. and D. Lane (eds.) *Antibodies—a Laboratory Manual*. Cold Spring Harbor, N.Y. (1988).

The antisera that has been partially purified by ammonium sulfate precipitation and dialysis versus PBS is passed over the antigen affinity column as described in Harlow, E. and D. Lane (eds.) *Antibodies—a Laboratory Manual*. Cold Spring Harbor, N.Y. (1 988). The antisera may be passed over the column multiple times, as this may lead to more complete binding of antibodies to the column. The column is then washed and the affinity-purified antibodies are eluted and dialyzed against PBS as described in Harlow, E. and D. Lane (eds.) *Antibodies—a Laboratory Manual*. Cold Spring Harbor, N.Y. (1988).

F. Assay for Blocking of Bacterial Binding by Antibodies to Intimin

To assess the effect of anti-intimin antibodies on EHEC adherence, mouse, rabbit, or goat anti-intimin antisera (or normal sera as controls) are added to EHEC bacteria suspended in adherence media, and the bacteria-antisera mixtures are incubated at 37° C. for thirty minutes prior to infection of HEp-2 cells. Antisera are maintained in the adherence media throughout the assay. Adherence and related sequelae are microscopically observed using GIEMSA and FITC-phalloidin (FAS) staining as described above.

To assess the effect of anti-intimin antibodies on adherence of other bacteria having intimin-like proteins, mouse, rabbit, or goat anti-intimin antisera (or normal sera as controls) are added to EHEC bacteria suspended in adherence media, and the bacteria-antisera mixtures are incubated at 37° C. for thirty minutes prior to infection of HEp-2 cells.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

G. Raising Monoclonal Antibodies Specific for Intimin

Monoclonal antibodies directed against intimin are used to passively protect a patient against colonization by EHEC (or bacteria expressing intimin-like proteins). Monoclonal antibodies are generated from mouse cells, and the specificity of these antibodies are changed for use in humans. G. Winter et al., "Man-made antibodies," *Nature*, 349: 293–299 (1991); P. T. Jones et al., "Replacing the complementarity-determining regions in a human antibody with those from a mouse," *Nature*, 321: 522–525 (1986); P. Carter et al., "Humanization of an anti-p185HER$^2$ antibody for human cancer therapy," Proc. Natl. Acad. Sci. USA, 89: 4285–4289 (1992). Monoclonal Abs represent a more "pure" antibody for administration to a patient.

1. Generation of anti-Eae monoclonal antibodies

Two examples of methods for generating anti-intimin monoclonal antibodies are described below.

a. Method 1

Generation of Anti-Eae mAbs

The procedure outlined in Harlow, E. and D. Lane, Antibodies, *A Laboratory Manual*, Cold Spring Harbor, N.Y. (1988) is followed with modifications. Nine week old female BALB/c (Harlan Spraque-Dawley, Indianapolis, Ind.) are used for the production of monoclonal antibodies. Prior to immunization, a serum sample is obtained from each mouse via the retro-orbital sinus. The whole blood is placed into a microfuge tube and allowed to cool at 4° C. for between 4 and 16 hours. Serum is prepared by centrifugation of the whole blood at 1000–1200×g for 15 minutes at 10–15° C. The serum is transferred to new microfuge tubes using a micropipettor and sterile pipets tips. The serum is stored at −20° C. until use.

The antigen is obtained from SDS-PAGE gels of RIHisEae, obtained as described above in Example II. The high molecular weight intimin band is excised with a razor, as described above in Example IX, section A, part 4. One mg of RIHisEae is run onto four MiniProtean II gels (BioRad, Richmond, Calif.) for this purpose. Protein excised from the gels are made into a slurry in approximately 8 mls of phosphate buffered saline (PBS) using a mortar and pestle. On experimental day 0, a 0.8 ml portion of the slurry is mixed with 1.2 mls of complete Freund's adjuvant (CFA) and injected in 0.2 ml aliquots subcutaneously into each of four mice. A 0.5 ml portion of the slurry is mixed with 0.5 mls of RIBI T-700 adjuvant (RIBI Immunochem, Hamilton, Mont.) and 0.2 mls is injected into each of four additional mice.

Mice receive booster injections on experimental days 21 and 42. The antigen is prepared as described above, with the exception that incomplete Freund's adjuvant (IFA) is used instead of CFA.

Serum samples are obtained as described above on experimental days 14, 35 and 49.

Serum samples are tested by immunoassay (as described below) to identify mice producing serum with the strongest response to Eae, as would be recognized to those skilled in the art. The reactivity of the serum samples is verified by Western blot analysis as described above in Example IX, section A, part 4. Three days prior to fusion (on experimental day 59), the mouse chosen for fusion is immunized with a 50% mixture of supernatant from the intimin slurry in PBS. A total of 0.1 mls of this slurry is injected intravenously via the tail vein.

Spleen cells from the chosen mouse are fused with SP2/0 myeloma cells (Cat #CRL1581 American Type Culture Collection, Rockville, Md. 20850, 301-881-2600). A ratio of 10 spleen cells: 1 myeloma is used for the fusion. Fusion is accomplished by the use of polyethylene glycol (Cat # 783 641 Boehringer-Mannheim Corp., 9115 Hague Road, PO Box 50414, Indianapolis, Ind. 46250, 800-262-1640). Fused cells are distributed into 96-well tissue culture dishes for growth. Hybridomas are selected by growth of the cultures for 10 days in medium containing hypoxanthine, aminopterin and thymidine. Hybridomas secreting anti-intimin specific antibodies are identified from the 96-well tissue culture dishes by immunoassay as described below. Cultures positive for antibodies reactive with Eae are expanded by transfer to 24-well dishes, retested for reactivity with Eae by immunoassay and cloned twice by limiting dilution.

Immunoassay (ELISA) of Mouse Polyclonal Anti-Intimin Serum and Hybridoma Supernatants (Anti-Intimin Monoclonal Antibodies)

A three ml portion of the intimin slurry used for immunization is centrifuged at approximately 1000×g for 15 minutes at room temperature. A sample of the resulting, clarified supernatant is used to coat immunoassay plates. Briefly, the intimin-containing supernatant is diluted 1:300 in PBS and used as a coating antigen. Nunc Maxisorp Stripwells are coated with 100 μl/well of the diluted supernatant for 2–24 hours at room temperature.

Unbound material is washed from the wells with four washes of PBS containing 0.5% Tween-20 (PBS-T). For assays of serum samples, multiple dilutions of each sample are prepared in PBS-T and added to replicate wells. For assays of culture supernatants from 96-well dish cultures, each supernatant is diluted 1:2 in PBS-T and added to a single well. Supernatants from 24-well dish cultures are also diluted 1:2 in PBS-T and tested in duplicate. Assays of serum samples include a buffer control and a known polyclonal anti-intimin control. Assays of supernatants include a buffer control, medium control and a known polyclonal anti-intimin control.

Serum and supernatants are allowed to incubate in a draft-free environment at room temperature for 30–60 minutes on the intimin-coated wells and unbound antibodies and extraneous material (such as serum proteins) are washed from the wells with four washes of PBS-T. Each well then receives 100 μl of rabbit anti-mouse IgG (gamma specific)-HRP (Zymed, South San Francisco, Calif.), diluted 1:4000 in PBS-T.

The plates are again allowed to incubate in a draft-free environment at room temperature for 30–60 minutes. Each well then receives 100 μl of one-component (tetramethylbenzidine) Kirkegaard and Perry Labs, Gaithersburg, Md. 20878, 301-948-7755). The reaction is allowed to proceed for 15 minutes in the dark and then stopped by the addition of 80 μl/well of TMB stop reagent (Kirkegaard and Perry Labs, Gaithersburg, Md. 20878, 301-948-7755).

b. Method 2

The procedure outlined in Harlow, E. and D. Lane, *Antibodies. A Laboratory Manual*. Cold Spring Harbor, N.Y. (1988) is followed: Five 4- to 5-week old female BALB/cJ mice are prebled, and immunized intraperitoneally with 25 μg RIHisEae suspended in 100 μl of TiterMax. Mice are boosted twice in two week intervals, intraperitoneally with 25 μg RIHisEae suspended in 100 μl of TiterMax. Seven days after each boost, blood (~300–500 μl) is collected from the tail vein. Sera are assayed for the presence of anti-RIHisEae antibody by ELISA (as described above).

Mice producing high titers of anti-RIHisEae antibodies are boosted both intravenously and intraperitoneally with 25 μg of RIHisEae in 100 μl of PBS, sacrificed three days later, and sera collected. Spleen cells are isolated and fused to Sp2/0-Ag mouse myeloma cells (ATCC #CRL1581) at a ratio of 10 spleen cells to 1 myeloma cell. Fused cells are distributed into microdilution plates, and culture supernatants are assayed by ELISA after 3–4 weeks of culture for RIHisEae antibodies. Cultures positive for production of anti-RIHisEae antibodies are expanded and cloned twice by limiting dilution.

2. Determination of whether anti-RIHIsEae mAbs recognize conformational or linear epitopes Reactivities of the mAbs are compared by: 1) ELISA in which native RIHisEae is used as the adsorbent; and 2) immunoblot of RIHisEae denatured and separated by SDS-PAGE. Several pools of mAbs are obtained: 1) those that recognize only conformational epitopes and react positively by ELISA but not by immunoblot analysis; 2) those that recognize linear epitopes and react in both assays; and 3) those that recognize linear epitopes and react positively by immunoblot analysis, but not by ELISA. In addition, colony immunoblots of unlysed cells are done to determine if the mAbs recognize Eae expressed on the surface of the wild type strain 86-24.

3. Testing of anti-Eae mAbs for capacity to block adherence of strain 86-24 to HEp-2 cells Strain 86-24 is subjected to a qualitative adherence assay on HEp-2 cells and tested in parallel with bacteria that have been pre-incubated with various dilutions of anti-RIHisEae mAbs.

Selected adherence-blocking and conformational mAbs are subjected to isotype determination (Immunopure mAb Typing Kit, Pierce, Rockford, Ill.). Unique antibodies are then purified by affinity chromatography on a Protein G Sepharose column (Pharmacia, Piscataway, N.J.). The resulting affinity-purified mAbs are re-tested for capacity to block adherence of strain 86-24 to Hep-2 cells to ensure that the antibody remains functional after purification.

H. Use of Polyclonal and Monoclonal Anti-intimin Antibodies in Diagnostic Kits.

Diagnostic kits can be used to detect intimin-expressing bacteria, preferably EHEC. A general description of the preparation and use of such kits is provided in copending U.S. Application Ser. No. 08/412,231, filed Mar. 10, 1995, the disclosure of which is incorporated herein by reference.

EXAMPLE VIII

High titer polyclonal anti-intimin antisera are elicited upon intraperitoneal injection of 25 μg RIHisEae into mice and rabbits, using Titremax adjuvant (CytRx Corp., 154 Technology Parkway, Technology Park/Atlanta, Norcross, Ga. 30092, 800-345-2987). Testing of antibody titer and an antibody effectiveness assay are shown. Monoclonal antibodies are also described.

A. Making Polyclonal Antibodies

The technique of Harlow, E. and D. Lane (eds) *Antibodies—a Laboratory Manual*. Cold Spring Harbor, N.Y. (1988) may be followed. The general procedure is outlined herein. Take pre-bleeds of each mouse to be immunized: Bleed from the tail vein into an eppendorf tube. Incubate at 37° C. for 30 min, stir gently with a sterile toothpick (to loosen the clot), store overnight at 4° C. In the morning, spin 10 min/10,000 rpm in the microfuge, and collect the serum (i.e., supernatant; red blood cells are the pellet). Store the serum at −20° C. The sera obtained will be used as a negative control after the mice are immunized.

Inject a BALB/c mouse intraperitoneally with 25 μg of RIHisEae (using Titremax adjuvant, according to the instructions of the manufacturer (CytRyx Corp., 154 Technology Pkwy., Norcross, Ga. 30092, 800-345-2987). Wait 2 weeks, boost with an identical shot, wait 7 days and bleed from the tail vein into an eppendorf tube. Incubate at 37° C. for 30 min, stir gently with a sterile toothpick (to loosen the clot), store overnight at 4° C. In the morning, spin 10 min/10,000 rpm in the microfuge, and collect the serum. Store the sera at −20° C.

B. ELISA to Test Titer of Abs.

The technique of Harlow, E. and D. Lane (eds) *Antibodies—a Laboratory Manual*. Cold Spring Harbor, N.Y. (1988) may be followed. The general procedure is outlined below:

(1) bind RIHisEae to plastic microtiter plates at 50 ng/well in PBS. Incubate 2 h/RT (room temp) or overnight at 4° C.

(2) wash plate 2× with PBS.

(3) block wells with 100 μl blocking solution [3% bovine serum albumin (Sigma Chemical, St. Louis, Mo.), 0.02% sodium azide (Sigma) in PBS—store stock at 4° C.] for 1–2 h at RT.

(4) wash plate 2× with PBS.

(5) primary Ab=50 μl test sera diluted in blocking solution for example, start with 1:50 and do eleven 1:2 dilutions, or start with 1:50 and do eleven 1:10 dilutions), incubate 2 h/RT.

(6) wash 4× with PBS.

(7) secondary Ab=goat horseradish-conjugated anti-mouse Ig, affinity purified (Boehringer Mannheim Corp., 9115 Hague Rd., P.O. Box 50414, Indianapolis, Ind. 46250, 800-262-1640). Add secondary Ab diluted 1:500 in blocking solution without azide. Incubate 1 h/RT.

(8) wash 4× with PBS.

(9) add 100 μl TMB Peroxidase substrate to each well (prepared according to the instructions of the manufacturer, BioRad Labs, 3300 Regatta Blvd., Richmond, Calif. 94804). Allow blue color to develop (no more than 10 min). Stop the reaction with 100 μl $H_2SO_4$. Read the plate at 450 nm.

A titer is defined as an absorbance value ≧0.2 units above that obtained for mouse pre-immune sera.

Anti-intimin Abs obtained from animals may be used clinically if one changes the specificity of the antibody to human. Such techniques are well known to those of ordinary skill in the art. G. Winter et al., "Man-made antibodies," *Nature*, 349: 293–299 (1991); P. T. Jones et al., "Replacing the complementarity-determining regions in a human antibody with those from a mouse," *Nature*, 321: 522–525 (1986); P. Carter et al., "Humanization of an anti-p185$^{HER2}$ antibody for human cancer therapy," *Proc. Natl. Acad. Sci. USA*, 89: 4285–4289 (1992). Such antibodies may be given to the sibling of an infected patient to reduce the risk of infection of the sibling.

C. Assay for Blocking of Bacterial Binding by Antibodies to Intimin

To assess the effect of anti-intimin antibodies on EHEC adherence, mouse or rabbit anti-intimin antisera (or normal sera as controls) are added to EHEC bacteria suspended in adherence media, and the bacteria-antisera mixtures are incubated at 37° C. for thirty minutes prior to infection of HEp-2 cells. Antisera are maintained in the adherence media throughout the assay. Adherence and related sequelae are microscopically observed using GIEMSA and FITC-phalloidin (FAS) staining as described above.

To assess the effect of anti-intimin antibodies on adherence of other bacteria having intimin-like proteins, mouse or rabbit anti-intimin antisera (or normal sera as controls) are added to EHEC bacteria suspended in adherence media, and the bacteria-antisera mixtures are incubated at 37° C. for thirty minutes prior to infection of HEp-2 cells.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

D. Raising Monoclonal Antibodies to Intimin

Monoclonal antibodies directed against intimin are used to passively protect a patient against colonization by EHEC (or bacteria expressing intimin-like proteins). Monoclonal antibodies are generated from mouse cells, and the specificity of these antibodies are changed for use in humans. G. Winter et al., "Man-made antibodies," *Nature*, 349: 293–299 (1991); P. T. Jones et al., "Replacing the complementarity-determining regions in a human antibody with those from a mouse," *Nature*, 321: 522–525 (1986); P. Carter et al., "Humanization of an anti-p185$^{HER2}$ antibody for human cancer therapy," *Proc. Natl. Acad. Sci. USA*, 89: 4285–4289 (1992). Monoclonal Abs represent a more "pure" antibody for administration to a patient.

1. Generation of anti-Eae mAbs: The procedure outlined in Harlow, E. and D. Lane, *Antibodies. A Laboratory Manual*. Cold Spring Harbor, N.Y. (1988) is followed: Five 4- to 5-week old female BALB/cJ mice are prebled, and immunized intraperitoneally with 25 μg RIHisEae suspended in 100 μl of TiterMax. Mice are boosted twice in two week intervals, intraperitoneally with 25 μg RIHisEae suspended in 100 μl of TiterMax. Seven days after each boost, blood (~300–500 μl) is collected from the tail vein. Sera are assayed for the presence of anti-RIHisEae antibody by ELISA (as described above).

Mice producing high titers of anti-RIHisEae antibodies are boosted both intravenously and intraperitoneally with 25 μg of RIHisEae in 100 μl of PBS, sacrificed three days later, and sera collected. Spleen cells are isolated and fused to Sp2/0-Ag mouse myeloma cells (ATCC #CRL1581) at a ratio of 10 spleen cells to 1 myeloma cell. Fused cells are distributed into microdilution plates, and culture supernatants are assayed by ELISA after 3–4 weeks of culture for RIHisEae antibodies. Cultures positive for production of anti-RIHisEae antibodies are expanded and cloned twice by limiting dilution.

2. Determination of whether anti-RIHIsEae mAbs recognize conformational or linear epitopes: Reactivities of the mAbs are compared by: 1) ELISA in which native RIHisEae is used as the adsorbent; and 2) immunoblot of RIHisEae denatured and separated by SDS-PAGE. Several pools of mAbs are obtained: 1) those that recognize only conformational epitopes and react positively by ELISA but not by immunoblot analysis; 2) those that recognize linear epitopes and react in both assays; and 3) those that recognize linear epitopes and react positively by immunoblot analysis, but not by ELISA. In addition, colony immunoblots of unlysed cells are done to determine if the mAbs recognize Eae expressed on the surface of the wild type strain 86-24.

Testing of anti-Eae mAbs for capacity to block adherence of strain 86-24 to HEp-2 cells: Strain 86-24 is subjected to a qualitative adherence assay on HEp-2 cells and tested in parallel with bacteria that have been pre-incubated with various dilutions of anti-RIHisEae mAbs.

Selected adherence-blocking and conformational mAbs are subjected to isotype determination (Immunopure mAb Typing Kit, Pierce, Rockford, Ill.). Unique antibodies are then purified by affinity chromatography on a Protein G Sepharose column (Pharmacia, Piscataway, N.J.). The resulting affinity-purified mAbs are re-tested for capacity to block adherence of strain 86-24 to Hep-2 cells to ensure that the antibody remains functional after purification.

EXAMPLE X

Agrobacterium Tumefaciens-mediated Transformation of Various Plants for Expression of Intimin.

Plants are transformed to express intimin, or functional portions of intimin, and fed to patients. As those of ordinary skill in this art would recognize, the intimin may be his-tagged as described in Example 1, or not. In addition, the intimin may be a fusion protein comprising intimin and one or more antigens against which an immune response is desired to be elicited. (See Example VII.)

Any plant tissue may be transformed with a vector of the present invention. The term "organogenesis," as used herein, means a process by which shoots and roots are developed sequentially from meristematic centers; the term "somatic embryogenesis," as used herein, means a process by which shoots and roots develop together in a concerted fashion (not sequentially). Exemplary tissue targets include leaf disks, pollen, embryos, somatic embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

A. Construction of the Plasmid Containing the eae Gene.

The present example uses the vector, pKYLX $71S^2$ (FIG. 17). This vector is obtained from David Hunt, Dept. of Crop Science, University of Kentucky, Lexington, Ky. but those in the art will recognize that other available vectors may be used or constructed. This vector is an Agrobacterium tumefaciens binary vector containing kanamycin in vivo selectable marker gene (NPTII). A binary vector system contains two plasmids. A tumor-inducing (Ti) plasmid contains DNA (t-DNA), into which the desired coding region is inserted in a multiple cloning region. The other plasmid contains vir genes, which are virulence genes enabling the t-DNA to enter plant cells and integrate into the genome. The pKYLX $71S^2$ vector places the desired coding sequence under the control of a doubled-enhanced cauliflower mosaic virus 35S (CaMV 35S or simply 35S) promoter. In this case, the doubled-enhanced promoter is two ribosomal promoters in tandem.

Agrobacterium vectors are useful for introducing foreign genes into a variety of plant species and particularly useful for the transformation of dicots. Numerous Agrobacterium vectors are known. See, e.g., U.S. Pat. No. 4,536,475 to Anderson, U.S. Pat. No. 4,693,977 to Schliperoort et al.; U.S. Pat. No. 4,886,937 to Sederoff et al.; T. Hall et al., EPO Application 0122791; R. Fraley et al., *Proc. Natl. Acad. Sci. USA* 84, 4803 (1983); L. Herrera-Estrella et al., *EMBO* J. 2, 987 (1983); G. Helmer et al., *Bio/Technology* 2, 5201 (1984); N. Murai et al., *Science* 222, 476 (1983).

The his-eae gene (obtained as described above in Example I) is ligated into vector pKYLX 71 $S^2$, creating the plant transformation vector pINT (FIG. 17), using recombinant techniques well known to those ordinarily skilled in the art.

The his-eae gene (obtained as described above in Example I) is ligated into vector pKYLX $71S^2$, creating the DNA construct pINT (FIG. 17). Such vectors containing heterologous DNA can be constructed using recombinant techniques well known to those ordinarily skilled in the art. For example, DNA from pEB313 (described above in Example I) is prepared with the use of a QIAGEN DNA extraction kit (QIAGEN, Chatsworth, Calif.). The his-eae gene is isolated by digestion of pEB313 with XhoI and NheI, separation on an agarose gel, followed by excision of the 3147 bp eae-containing band with a razor. The purified DNA is extracted from the agarose with GeneClean (Bio101, LaJolla) and ligated into pKYLX$71s^2$ digested with XhoI and XbaI. Liagated plasmids are transformed into DH5αF'Tn5lac$I_Q$, and transformants verified for the presence of inserted DNA by digestion with appropriate restriction enzymes. See also Example I. Any publicly available *Agrobacterium tumefaciens* strains may be used, but strains LBA4404, GV3850 or EHA 105 (obtainable from Stanley Gelvin, Purdue University, West Lafayette, Ind.) are preferred. The pINT plasmid is transferred to *A. tumefaciens* using calcium-chloride ions, followed by freeze-thaw transformation, electroporation, or other methods well known to the art. See, for example, Hanahan, D., J. Mol. Biol. 166:577–80 (1983).

B. Transformation of Tobacco.

Tobacco is used very commonly as a model for plant transformation. A general assumption that had been confirmed by many empirical studies is that if a transgene is expressed in tobacco then it will be expressed in another dicot plant. Recognizing that tobacco is not an edible plant, if a recombinant intimin is produced in tobacco, then it will be expressible in an edible plant such as canola.

Tobacco (*Nicotiana tabacum*) cultivar 'Xanthi' is transformed by Agrobacterium-mediated transformation using a standard and efficient infection protocol (Schardl et al., Gene 61: 1–11 (1987)). Briefly, tobacco leaf discs .5 cm in diameter are wounded and exposed to the *Agrobacterium tumefaciens* containing pINT. Plants are regenerated using an organogenic method under kanamycin selection (200 mg/L) in tissue culture.

Two hundred 0.5 cm leaf disks of tobacco are exposed to *Agrobacterium tumefaciens* harboring pINT. Tissue culture and plant regeneration conditions follow Schardl. et al 1987. Shoots are formed directly from wounded leaf disks under 200 mg/L kanamycin selection and 400 mg/L Timentin to kill Agrobacteria. This system is both highly efficient and not leaky (non-transgenic "escapes" are extremely rare). Three hundred and seventy-five shoots are produced from the experiment and 120 of these are arbitrarily selected for rooting on hormone-free media. All plants are morphologically normal and fertile. These results fall within the typical transformation efficiencies using this system. The high transformation frequencies and the fact that the plants are healthy indicate that intimin is not toxic, and does not interfere with normal plant development and function.

To determine that his-eae is stably integrated into the plant, leaf tissue is processed according to well known methods for Southern (DNA) blot analysis (Stewart et al., Plant Physiol. 112:121–129 (1996); Stewart, C. N., Jr. and Via, L. E., Biotechniques 13: 748–751 (1993). et al.), PCR analysis (Stewart et al., Plant Physiol. 112:121–129 (1996), and Western (protein) blot analysis (Stewart et al., Plant Physiol. 112:121–129 (1996). Southern blotting is performed to verify the presence of the eae gene in the DNA of the leaf tissue. PCR analysis is performed to verify the presence of the eae gene, as well. Primers used may include those mentioned above in Example I part D. For example, PCR amplification of putative eae-containing plant DNA using the primers MW1 (=5' GTACGGATCCGAAT-TCATTTGCAAATGGTG 3') SEQ ID NO:6 and MW2 (=5' GTACGGTACCTGATCAATGAAGACGTTATAG 3' ) SEQ ID NO:7 results in an expected 734 bp band when resolved on an agarose gel. Western blot analysis is performed to determine levels of expression of his-intimin within the leaf. Once expression of his-intimin exceeds 0.1% of total plant protein, the his-intimin protein is isolated using a one step nickel column purification (Stolz et al., Plant Journal 6: 225–233 (1994)). The purification method of Example II is an alternative. His-intimin is subjected to the adherence assay shown in Example III to verify functional binding.

Preparation of Extracts

Protein extracts are recovered from putative transgenic tobacco plants as follows: Five hundred microliters of extraction buffer (20 mls 0.5 M Tris HCl pH 8.0, 4 mls 0.5 M EDTA pH 8.0, 36 mls glycerol, 20 mls β-mercaptoethanol) or 500 µl of phosphate buffer (50 mM Na-phosphate pH 7.8, 300 mM NaCl) are added to 0.2 g of leaf tissue, the mixture is homogenized on ice, and then clarified by a pulse spun in a microfuge. The supernatant recovered, placed into a fresh eppendorf tube and stored at −70° C. Protein extracts are tested by Western blot analysis as described in Stewart et al., Plant Physiol. 112:121–129 (1996), using any of the monoclonal or polyclonal anti-intimin antibodies described in Example IX above.

If expression of his-intimin is hampered by the high Adenine (A)/Thymine (T) content of eae, the gene is rebuilt using methods outlined in Adang et al. (Adang et al., 1993), incorporated herein by reference. Briefly, for the segment of eae contained within pINT, the nucleotide sequence is analyzed to determine the codon specifying each amino acid in the intimin fragment. Capitalizing on the redundancy of the genetic code, the codons are rewritten to replace A or T with C or G without changing the amino acid specified by the codon; thus, codons of heterologous DNA, of bacterial origin, for example, are replaced with codons that are preferred for expression in a plant cell. The preferred substitutions are chosen according to the codon preference for the plant species being used. For instance, see Murray, E. E., et al., Nucleic Acids Res. 17 (2): 477–498 (1989); Dinesh-Kumar, S. P. and Miller, W. A., Plant Cell 5 (6): 679–692 (1993); Kumar, P. A. and Sharma, R. P., J. Plant Chemistry and Plant Biotechnol. 4 (2): 113–115 (1995).

The synthetic gene sequence is divided into regions of 200–300 bp and oligonucleotides are synthesized for each region. Oligonucleotides are synthesized by Research Genetics, Huntsville, Ala. The ordinarily skilled artisan will recognize that the oligonucleotides may be synthesized in many other commercial laboratories. The oligonucleotides are ligated according to the method set forth in Adang et al. Plant Mol. Biol. 21: 1131–1145 (1993) and the reconstructed gene is inserted into pKYLX 71S$^2$. The resulting plasmid, pINTrecCA, is used to transform any one of the preferred *Agrobacterium tumefaciens* strains LBA4404, GV3850 or EHA105. The tobacco is transformed and the expression product analyzed as set forth above.

C. Transformation of Other Plants.

Tobacco is not edible, therefore any intimin expressed in the tobacco plant must be purified to remove alkaloids for safe use. Plants that are part of the normal diet for the patient and are easily engineered are preferred. As examples, which are not intended to be limiting, for cattle, swine, and mutton, either canola (Stewart et al., Insect control and dosage effects in transgenic canola, *Brassica napus* L. (Brassicaceae), containing a synthetic *Bacillus thuringiensis* CryIa(c) gene (Stewart et al., Plant Physiol. 112:115–120 (1996)) or alfalfa (Thomas et al., Plant Cell Rep. 14: 31–36 (1994)) may be transformed to express intimin or an intimin fusion protein. For humans, canola or carrot (Droge et al., 1992) may be transformed.

The patient should ingest the intimin-containing plant or the intimin-containing portion of a plant. The injested portion may be a plant leaf, root, fruit, berry, seed, tuber, corm, inflorescence, stem etc. or combination thereof. The injested portion may also be extracted from a plant as a plant derivative such as, for example, flour, meal, slurry, infusion, paste, juice, powder, cake, or pellet. The injested portion may be further incorporated into a complex feedstock or foodstuffs according to techniques commonly known in the art.

Haq et al., Science, 268:714–716, 1995 have made transgenic tobacco and potato plants using genes encoding the B subunit of the ETEC heat-labile enterotoxin (LT-B) or this gene with a microsomal retention sequence (SEKDEL) SEQ ID NO:27. Both plants expressed the fusion proteins, which formed oligomers that bound the natural ligand. When mice were tube fed a crude soluble extract of tobacco leaves expressing LT-B-SEKDEL SEQ ID NO:27, they produced serum and gut mucosal anti-LT-B immunoglobins that neutralized the enterotoxin in cell protection assays. Mice fed potato tubers expressing LT-B-SEKDEL also developed serum and gut mucosal immunity specific for LT-B.

Plants which may be employed in practicing the present invention include (but are not limited to) tobacco (*Nicotiana tabacum*), potato (*Solanum tuberosum*), soybean (*glycine max*), sunflower, peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), lettuce (e.g., *Lactuea sativa*), green beans (*Phaseolus vulgaris*), lima beans (*Phaseolus limensis*), peas (Pisum spp.) and members of the genus Cucumis such as cucumber (*C. sativus*), cantaloupe (*C. cantalupensis*), and musk melon (*C. melo*). Ornamentals include azelea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*dianthus caryophyllus*), poinsettia (*Euphorbia pulcherima*), and chrysanthemum. Gymnosperms which may be employed to carrying out the present invention include conifers, including pines such as loblollypine (*Pinus taeda*), Douglas-fir (*Pseudotsuga menziesil*); Western hemlock (*Tsuga canadensis*); Sitka spruce (Picea glauca); and redwood (*Sequoia sempervirens*).

EXAMPLE XI

Gene Gun-mediated Transformation of Various Plants, for Example, Monocots like Corn, Wheat, and Rice.

Another method of transforming plants to express intimin or intimin fusion proteins is provided. The plasmid described in Example IX, pINT, is coated onto microprojectiles (microparticles). Specifically, 1 µg of pINT is coated onto 10 mg of gold microparticles 1 micron in diameter (Biorad Laboratories tungsten particles obtained from Sylvania may also be used). Next, 5 µl of $10^8$ cells of *Agrobacterium tumefaciens* are overcoated onto the pINT coated microprojectile. One mg of the doublecoated microprojectiles is loaded into the PDS 1000-He gun, according to manufacturer. (Biorad Laboratories) One gram of soybean embryos initiated from immature cotyledons are bombarded with the doublecoated microprojectiles at 1000 psi. Bombarded embryos are grown under selection for kanamycin (200 mg/L) in tissue culture. They are allowed to mature and germinate and are fed to animals, such as pigs.

The same method may be used to transform bananas. The above method may also be accomplished without the step of adding *Agrobacterium tumefaciens*. Reconstruction of the eae gene or desired gene region may be accomplished as set forth in Example IX.

EXAMPLE XII

Expression of Intimin as Chimeric Virus Particles (CVP) Fusion Proteins

Another method of transforming plants to express intimin is through the use of a recombinant plant virus. This method is preferred for the rapid development and delivery of inexpensive oral vaccines. An intimin or intimin-like protein, or portion thereof, or recombinant fusion protein thereof, may be expressed using a plant recombinant viral infection and expression system such as that described by Dalsgaard and coworkers (Dalsgaard et al., Nature Biotechnology, 15:248–252 (1997), the disclosure of which is incorporated herein by reference), and as further described by Arntzen (Nature Biotechnology, 15:221–222 (1997), the disclosure of which is incorporated herein by reference). In a preferred embodiment, DNA encoding the intimin or intimin-like protein, or portion thereof, or recombinant fusion protein thereof, is recombinatorily inserted into a gene encoding a coat protein thereof, and optimally is expressed as a fusion protein with the coat protein with the coat protein. Preferably, the intimin or intimin-like protein, or portion thereof, or fusion protein thereof, is antigenic. The resulting recombinant viral genome is then propagated in a plant, portion or a plant, plant cell or plant extract, resulting in the expression of intimin or intimin-like protein, or portion thereof, or recombinant fusion protein. The intimin or intimin-like protein, portion thereof, or recombinant fusion protein thus produced by a viral vector may be ingested, extracted, enriched, purified or otherwise applied to the methods disclosed elsewhere herein.

EXAMPLE XIII

Expression of His-Intimin in another Bacterial Species that does not Normally Express it The intimin or intimin-like protein, portion thereof, or recombinant intimin fusion protein may be expressed in a host bacterium and the host bacterium may be given as a vaccine. For example, Su. G-F. et al. Microbial Pathogenesis 13:465 (1992), the materials and methods segment for which are hereby incorporated by reference, show the Shiga toxin B subunit fused to the 23 kDa C-terminus of *E. coli* hemolysin A (HlyA) which was then used to export it from an attenuated carrier strain of *Salmonella typhimurium aroA* (SL3261). The expression of this gene fusion was under constitutive control or under the control of an iron-regulated promoter. Oral and intraperitoneal immunization of mice with the hybrid strain resulted in significant B-subunit specific mucosal and serum Ab responses. Both cytoplasmic expression and extracellular export from the antigen carrier strain were shown to result in antigen-specific immune responses.

In addition, Pozzi, G. et al. Infect. Immun. 60:1902 (1992), the disclosure of which is hereby incorporated by reference, show a system in which a foreign antigen is fused to the C-terminal attachment motif of the fibrillar M protein from *Streptococcus pyogenes*. The fusion protein is expressed on the surface of *S. gordonii*, a commensal organism of the oral cavity. In this study, the E7 protein of human papillomavirus type 16 was chosen as the foreign antigen and was fused to the fibrillar M protein. Mice were infected subcutaneously. The M-E7 fusion protein expressed on the surface of *S. gordonii* was shown to be immunogenic for both aspects of the fusion protein in mice as demonstrated by Western blot analysis using sera pooled from infected mice.

In addition, Schafer, R. et al. J. Immunol. 149:53 (1992), the materials and methods segment for which are hereby incorporated by reference, showed *Listeria monocytogenes* expressing *E. coli* β-galactosidase (foreign antigen) was used as a live vaccine vector. BALB/c mice were immunized orally or intraperitoneally. Spleen cells harvested one week after oral or five weeks after oral or peritoneal infection (boosted at 4 weeks) showed β-galactosidase-specific cytotoxic T lymphocyte responses. Individual serum samples from mice immunized intraperitoneally or intravenously were tested for anti-β-galactosidase antibodies; approximately 11% had positive titers for these antibodies. These results show that both oral and parenteral immunization with this species results in a cellular immune response to a foreign protein.

An example of practicing the present invention according to the method of Su et al. is shown herein. In this example, eae (or his-eae) is placed under the control of the aerobactin promoter and fused to a DNA fragment encoding the 23 C-terminal hemolysin A (HlyA) signal domain, which targets the desired protein extracellularly. The aerobactin promoter is activated under iron limitation, a condition found in the intestinal mucosal environment, which promotes gene expression in vivo. The plasmid used to promote such expression is a medium copy pBR322-based plasmid, which confers a greater degree of immunity than a higher copy plasmid, such as pUC18. The bacterial host for expression of the foreign protein is *Salmonella typhimurium aroA* strain SL3261 pLG575, an attenuated derivative of an intestinal pathogen (available from Kenneth Timmis, Dept. of Microbiology, GBF-National Research Centre for Biotechnology, Braunschweig D-3300, Germany, as described in Su et al.). This strain also contains plasmid pLG575, encoding the hlyB and hlyD genes which are required for export of the intimin-HlyA protein.

Figure 18:
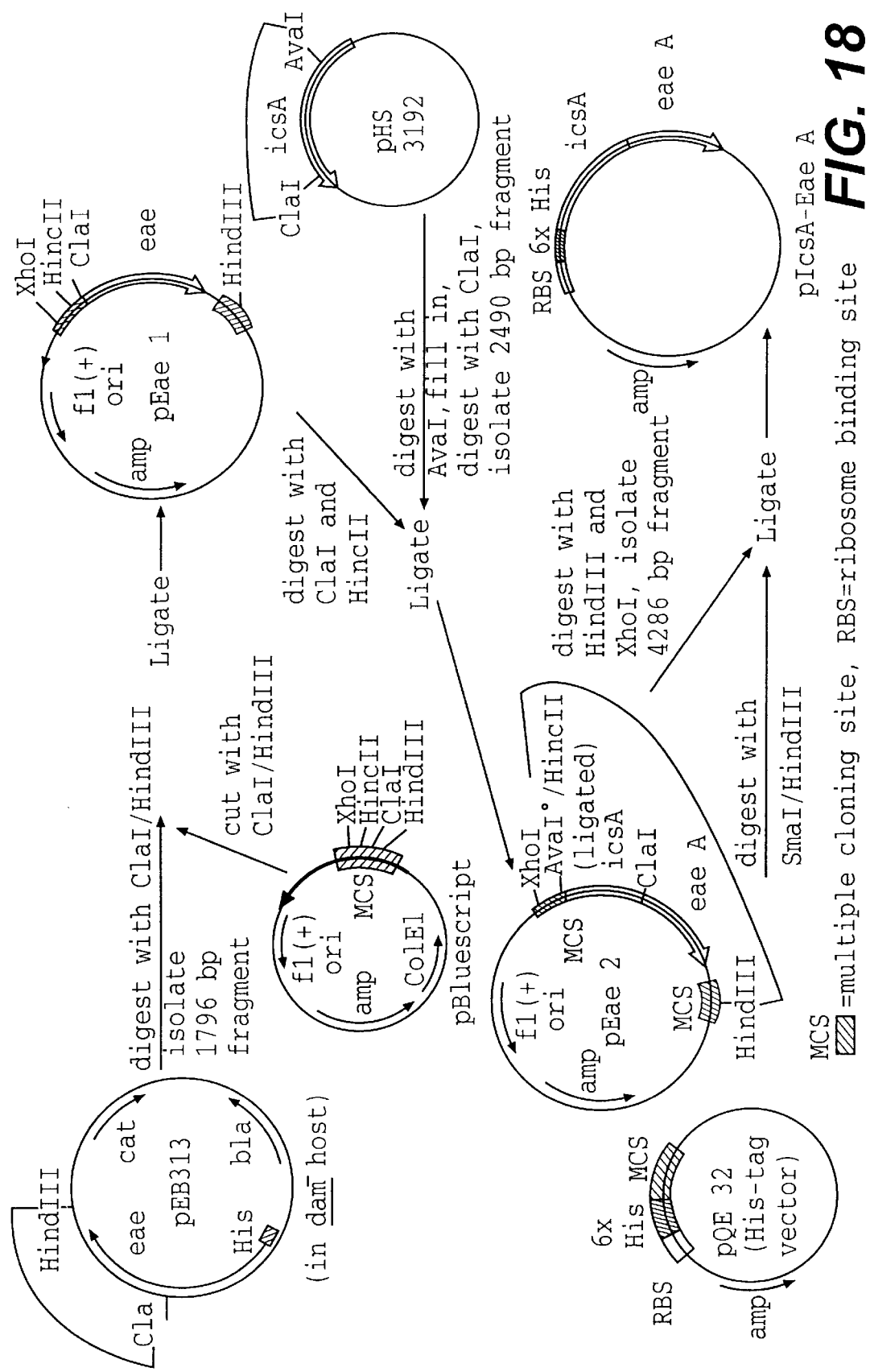
Figure 19:
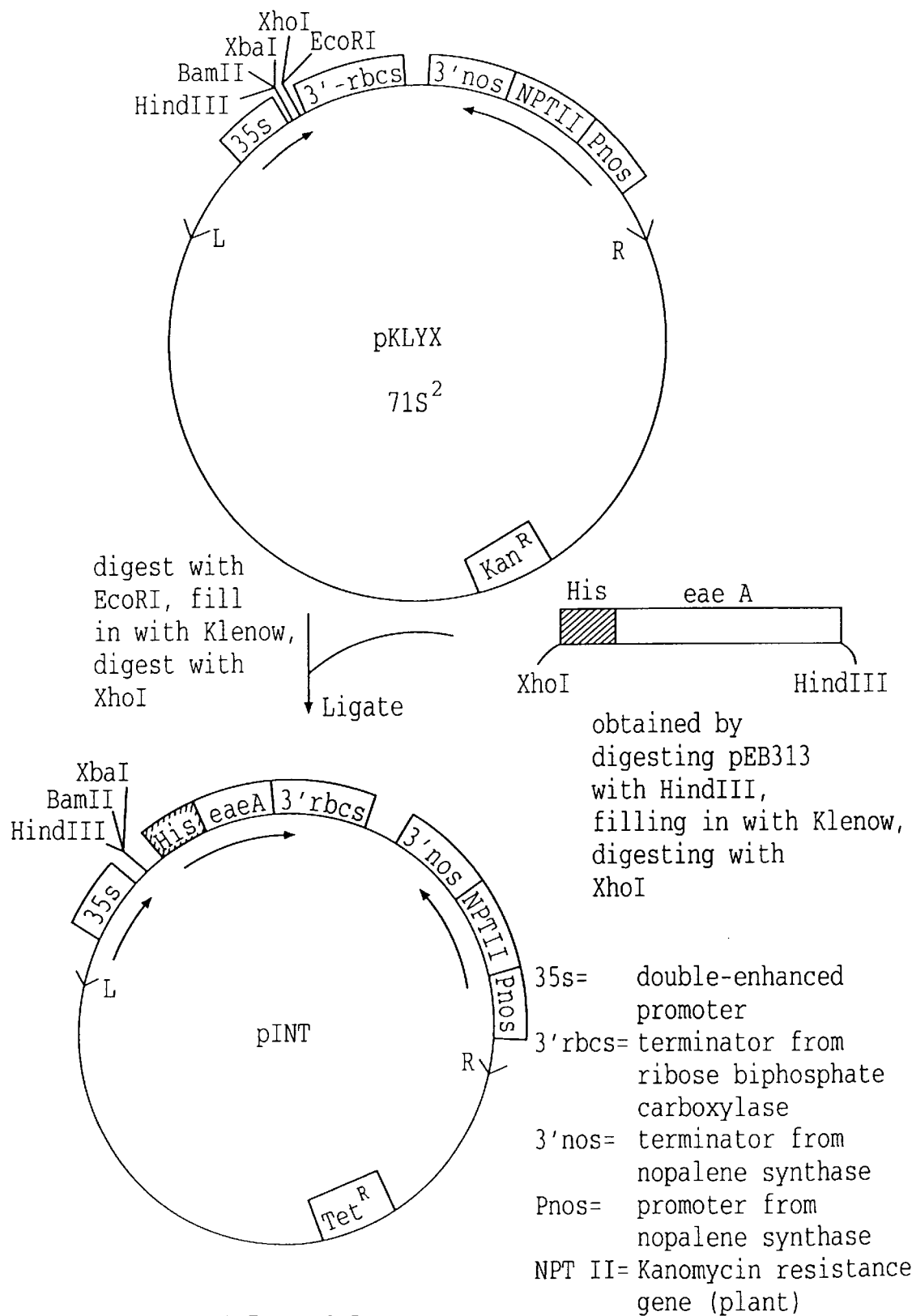
Figure 20:
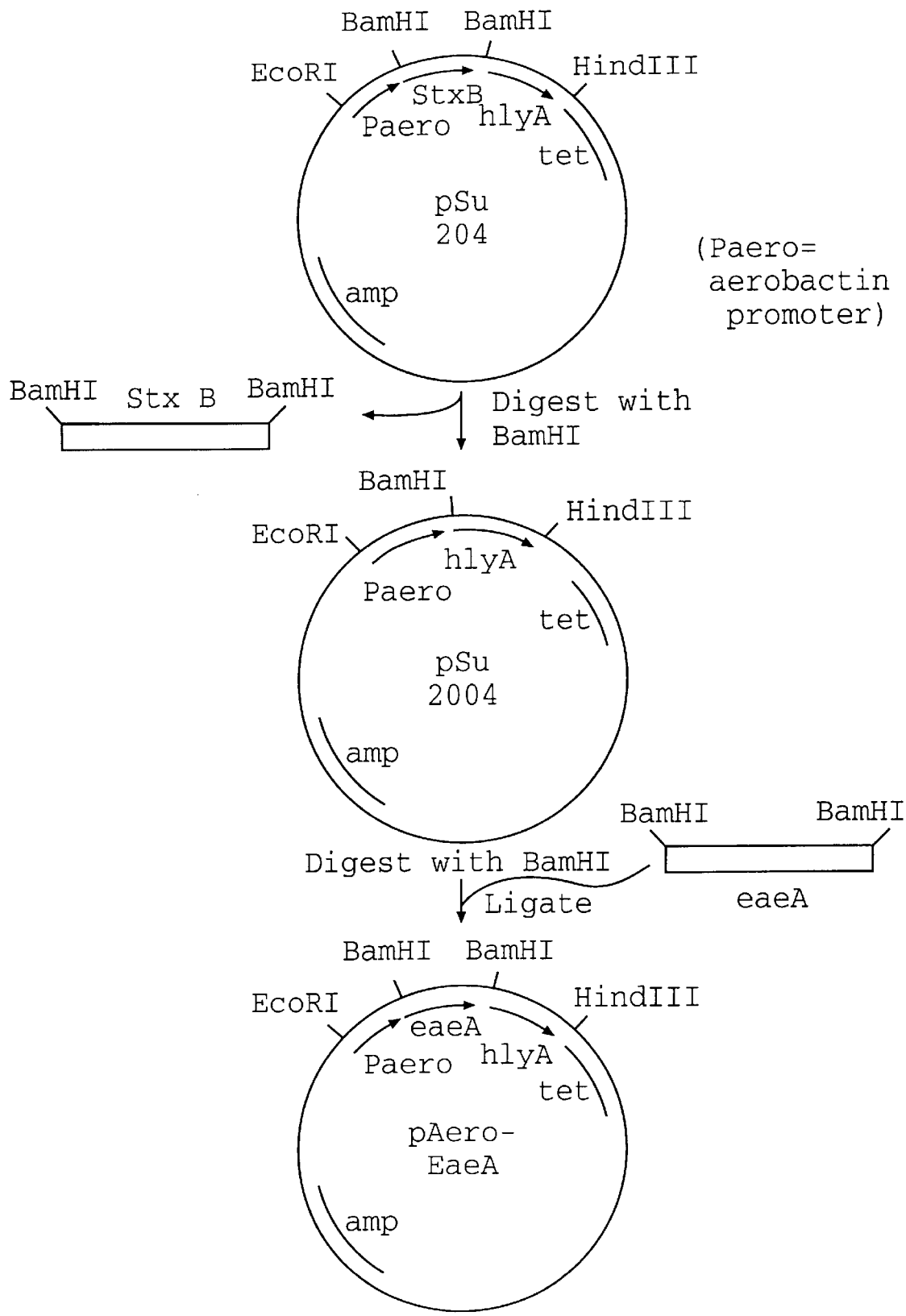
Figure 21:
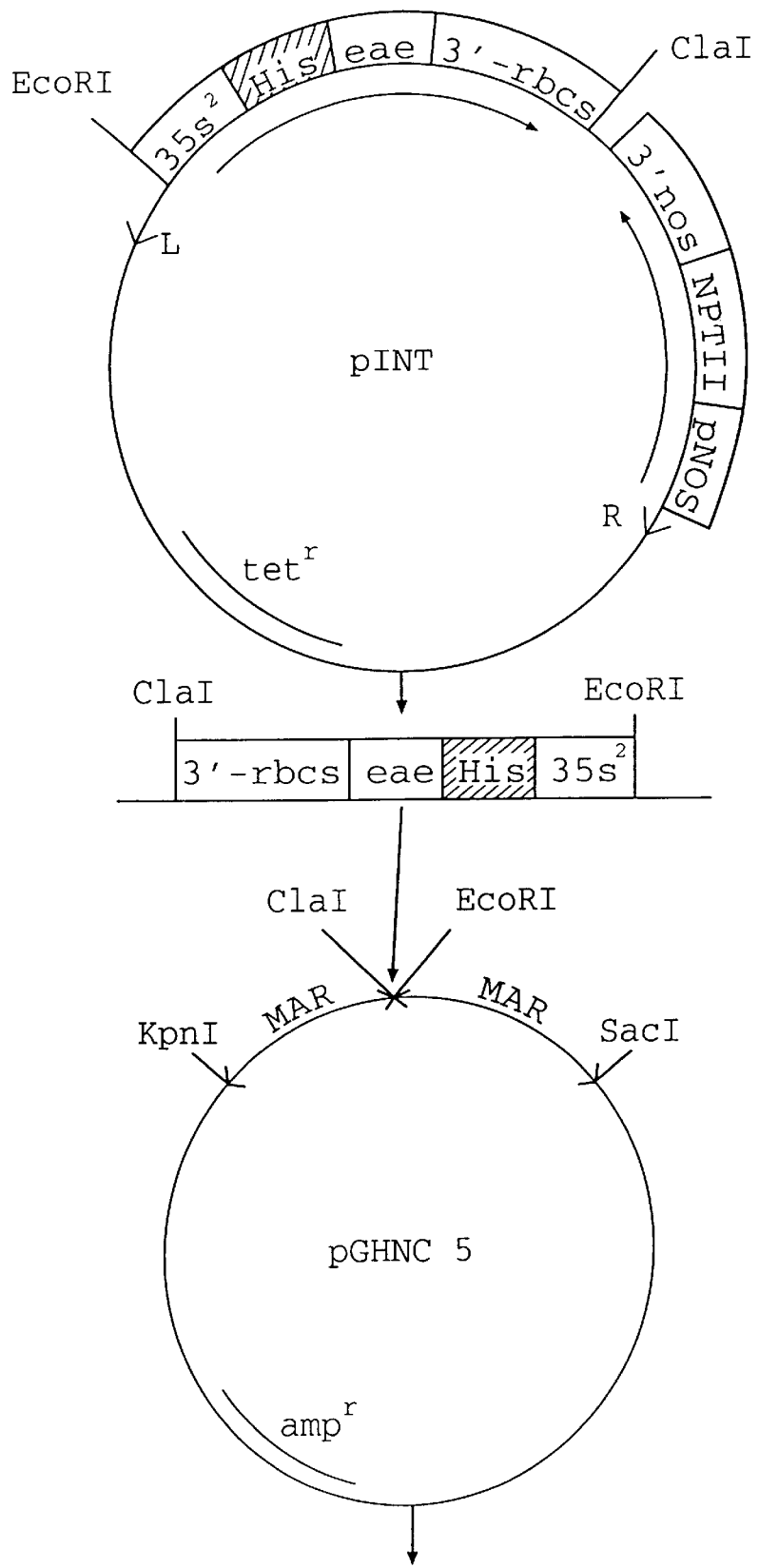
Figure 22:
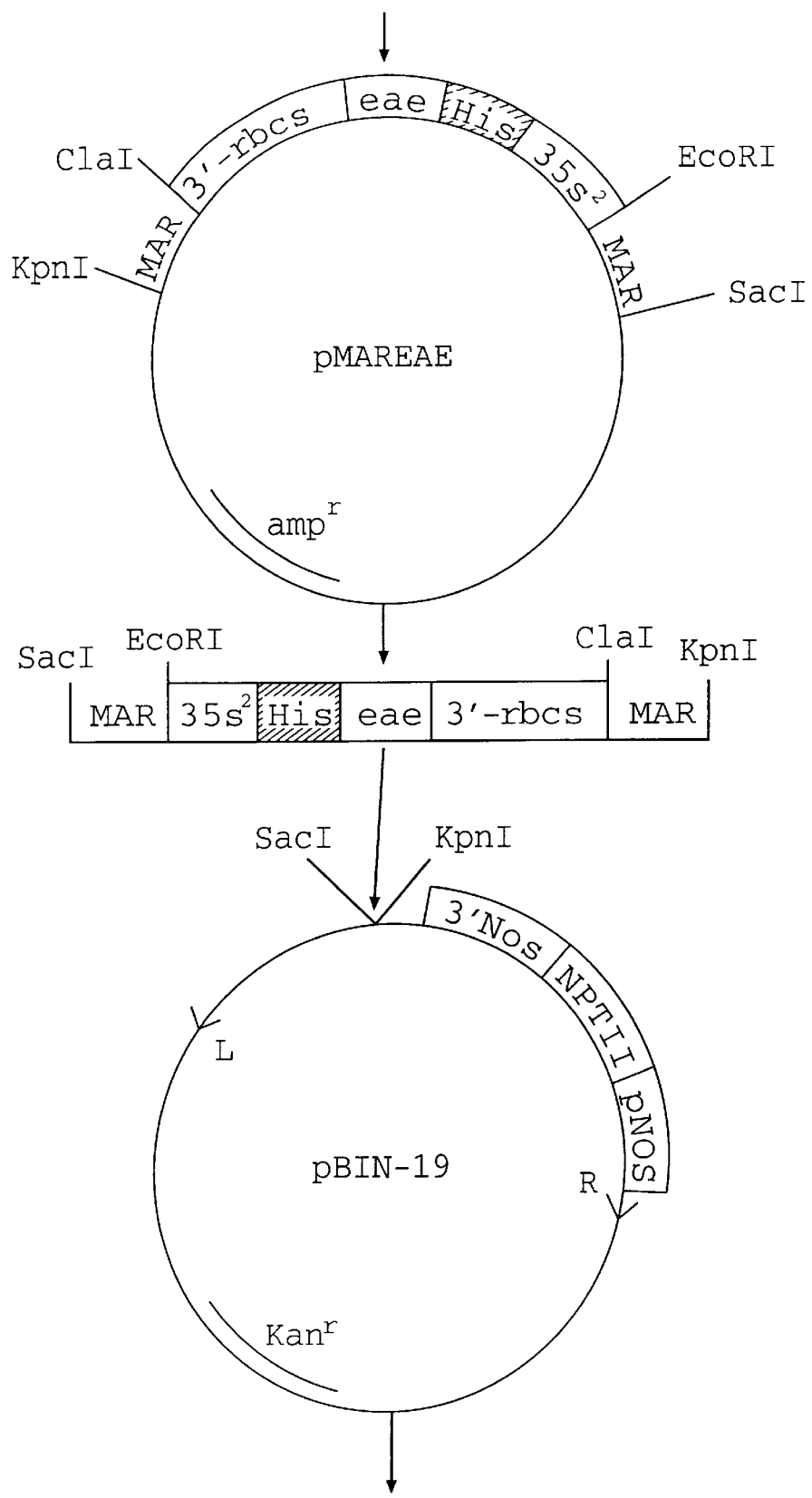
Figure 23:
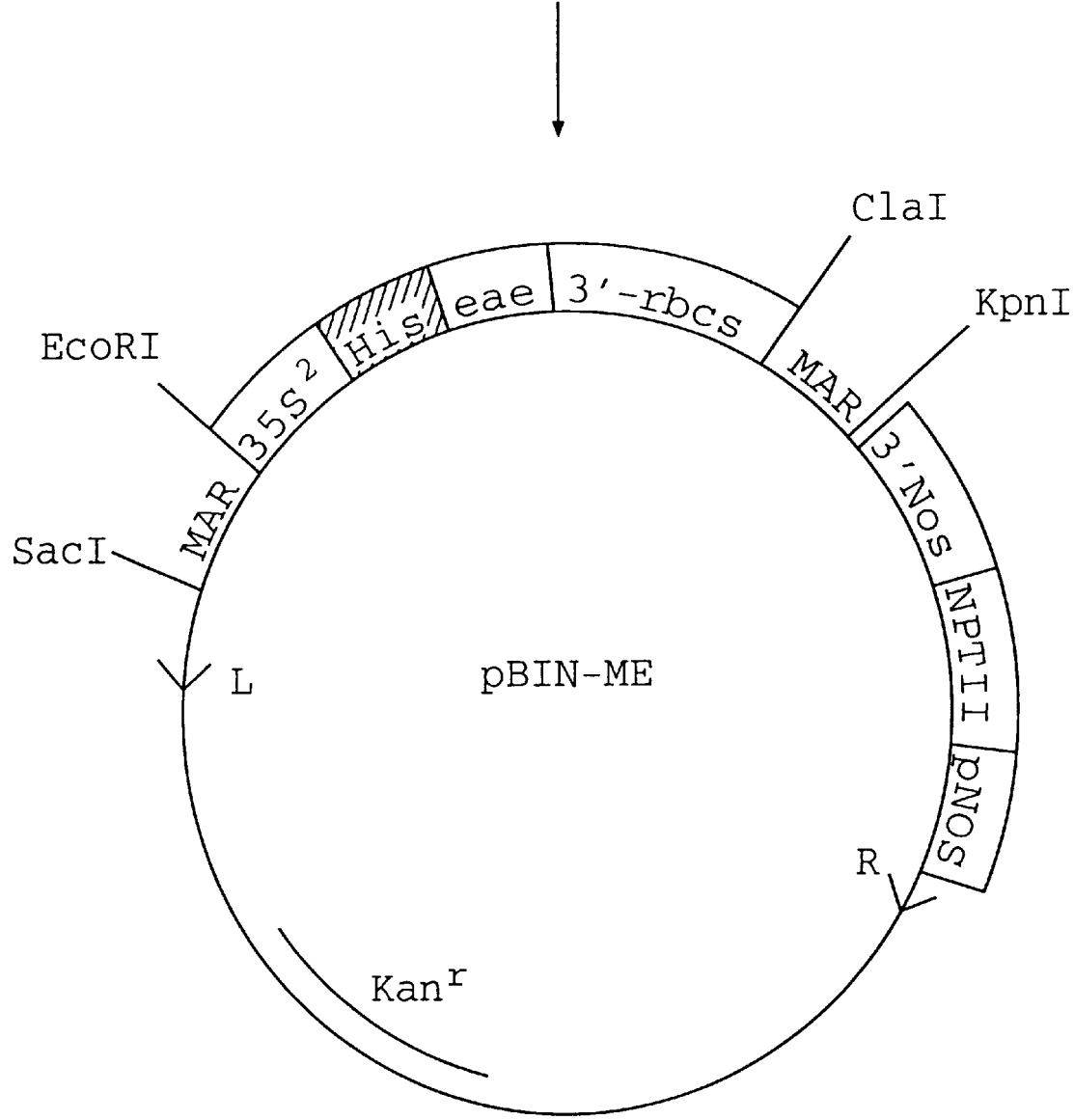

Briefly, (FIG. 18) the BamHI StxB fragment is dropped out of the plasmid pSU204 (available from Kenneth Timmis, Dept. of Microbiology, GBF-National Research Centre for Biotechnology, Braunschweig D-3300, Germany, the above reference), creating pSU2004. A BamHI DNA fragment encoding intimin or an intimin fusion protein is constructed by PCR such that the coding region is in the correct reading frame with both the aerobactin promoter contained on pSU2004, as well as the hlyA coding region. The BamHI eae fragment is ligated into pSU2004, resulting in pAero-Eae. This plasmid is transformed into the restriction-negative modification-positive *S. typhimurium* strain SL5283 (available from Kenneth Timmis) according to the method Hanahan, D. J., *Mol. Biol.* 166:577–580 (1983). Such a step modifies the pAero-Eae DNA by methylation, and plasmid DNA purified from this strain transforms *S. typhimurium aroA* strain SL3261 pLG575 more efficiently. Methylated pAero-Eae DNA is transformed into *S. typhimurium aroA* strain SL3261 pLG575 by the method of Hanahan, D. J., *Mol. Biol.* 166:577–580 (1983).

Eight to ten week old female BALB/c mice are fed the immunogenic bacterial host as follows. Bacteria are grown overnight at 37° C. in LB broth containing 100 μg/ml ampicillin, inoculated at a dilution of 1:50 into fresh media, and grown until the $OD_{600}$=0.3. The promoter is then induced with 2,2'-bipyridyl (100 μM final concentration) for 3 hours. The culture is washed and resuspended in PBS for feeding.

Two doses of bacteria are fed 4 days apart with $10^{10}$ CFU, with the aid of a feeding tube. Twenty one days after the first feeding, a booster injection is given. Mice are sacrificed one week later and show a mucosal and humoral immune response.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A plant cell expressing intimin, comprising a plant cell transformed with a plant transformation vector comprising heterologous DNA encoding intimin under the control of a plant promoter, wherein the intimin which is expressed from the heterologous DNA retains binding function.

2. A method for producing intimin in a plant, comprising the steps of:

a) transforming a plant cell with a plant transformation vector comprising heterologous DNA encoding intimin under the control of a plant promoter, wherein the intimin which is expressed from the heterologous DNA retains binding function;

b) regenerating a plant from said transformed plant cell, wherein the regenerated plant expresses the intimin; and c) utilizing the regenerated plant expressing intimin as a source of intimin.

3. The method of claim 2, further comprising enriching or purifying the intimin from the regenerated plant.

4. The plant cell of claim 1, wherein the plant cell resides in a plant tissue capable of regeneration.

5. The plant cell of claim 1, wherein the plant transformation vector is an Agrobacterium vector.

6. The plant cell of claim 1, wherein the plant transformation vector is a viral vector.

7. The method of claim 2, wherein the plant transformation vector is an Agrobacterium vector.

8. The method of claim 2, wherein the plant transformation vector is a microparticle.

9. The method of claim 8, wherein the plant cell is transformed by bombardment with the microparticle.

10. The method of claim 2, wherein the plant transformation vector is a viral vector.

11. The method of claim 2, wherein the regenerated plant comprises shoots.

12. The method of claim 2, wherein the regenerated plant comprises roots.

13. The method of claim 3, wherein the enriching or purifying comprises using at least one of high performance liquid chromatography (HPLC), gel column chromotography, and SDS-PAGE.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

CGTTGTTAAG TCAATGGAAA C        21

(2) INFORMATION FOR SEQ ID NO: 2:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

TCTAGAGAGA AACGTGAAT GTTGTCTCT        29

(2) INFORMATION FOR SEQ ID NO: 3:

(i) SEQUENCE CHARACTERISTICS:
      (A) LENGTH: 37 base pairs
      (B) TYPE: nucleic acid
      (C) STRANDEDNESS: single (D) TOPOLOGY: linear (ii) MOLECULE TYPE: DNA (genomic)

(xi) SEQUENCE DESCRIPTION: SEQ ID NO: 3:

GTACGGATCC ATGATGGTTT TCCAGCCAAT CAGTGAG                      37

(2) INFORMATION FOR SEQ ID NO: 4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GTACGGTACC TTATATTGAC AGCGCACAGA GCGGG                        35

(2) INFORMATION FOR SEQ ID NO: 5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GTACGGATCC ATATGTGGAA TGTTCATGGC TGGGG                        35

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GTACGGATCC GAATTCATTT GCAAATGGTG                              30

(2) INFORMATION FOR SEQ ID NO: 7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GTACGGTACC TGATCAATGA AGACGTTATA G                            31

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GTACGGATCC TGATCAGGAT TTTTCTGGTG                                              30

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GTACGGTACC TGATCAAAAA ATATAACCGC                                              30

(2) INFORMATION FOR SEQ ID NO: 10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GTACGGATCC TGATCAAACC AAGGCCAGCA TTAC                                         34

(2) INFORMATION FOR SEQ ID NO: 11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GTACGGTACC TTATTCTACA CAAACCGCAT AG                                           32

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GTACGGATCC ACTGAAAGCA AGCGGTGGTG ATG                                          33

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GTACGGATCC TTCATGGTAT TCAGAAAATA C                                            31

(2) INFORMATION FOR SEQ ID NO: 14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GTACGGATCC GACTGTCGAT GCATCAGGGA AAG                         33

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GTACGGATCC GAATGGTAAA GGCAGTGTCG                            30

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GTACGGTACC TCCAGAACGC TGCTCACTAG                            30

(2) INFORMATION FOR SEQ ID NO: 17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GTACGGTACC TTATTCTACA GAAACCGCAT AG                        32

(2) INFORMATION FOR SEQ ID NO: 18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

ATAACATGAG TACTCATGGT TG                                    22

(2) INFORMATION FOR SEQ ID NO: 19:

(i) SEQUENCE CHARACTERISTICS:

-continued (A) LENGTH: 934 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 19:

```
Met Ile Thr His Gly Cys Tyr Thr Arg Thr Arg His Lys His Lys Leu
1               5                   10                  15

Lys Lys Thr Leu Ile Met Leu Ser Ala Gly Leu Gly Leu Phe Phe Tyr
            20                  25                  30

Val Asn Gln Asn Ser Phe Ala Asn Gly Glu Asn Tyr Phe Lys Leu Gly
            35                  40                  45

Ser Asp Ser Lys Leu Leu Thr His Asp Ser Tyr Gln Asn Arg Leu Phe
    50                  55                  60

Tyr Thr Leu Lys Thr Gly Glu Thr Val Ala Asp Leu Ser Lys Ser Gln
65                  70                  75                  80

Asp Ile Asn Leu Ser Thr Ile Trp Ser Leu Asn Lys His Leu Tyr Ser
                85                  90                  95

Ser Glu Ser Glu Met Met Lys Ala Ala Pro Gly Gln Gln Ile Ile Leu
            100                 105                 110

Pro Leu Lys Lys Leu Pro Phe Glu Tyr Ser Ala Leu Pro Leu Leu Gly
            115                 120                 125

Ser Ala Pro Leu Val Ala Ala Gly Gly Val Ala Gly His Thr Asn Lys
        130                 135                 140

Leu Thr Lys Met Ser Pro Asp Val Thr Lys Ser Asn Met Thr Asp Asp
145                 150                 155                 160

Lys Ala Leu Asn Tyr Ala Ala Gln Gln Ala Ala Ser Leu Gly Ser Gln
                165                 170                 175

Leu Gln Ser Arg Ser Leu Asn Gly Asp Tyr Ala Lys Asp Thr Ala Leu
            180                 185                 190

Gly Ile Ala Gly Asn Gln Ala Ser Ser Gln Leu Gln Ala Trp Leu Gln
        195                 200                 205

His Tyr Gly Thr Ala Glu Val Asn Leu Gln Ser Gly Asp Asn Phe Asp
    210                 215                 220

Gly Ser Ser Leu Asp Phe Leu Leu Pro Phe Tyr Asp Ser Glu Lys Met
225                 230                 235                 240

Leu Ala Phe Gly Gln Val Gly Ala Arg Tyr Ile Asp Ser Arg Phe Thr
                245                 250                 255

Ala Asn Leu Gly Ala Gly Gln Arg Phe Phe Leu Pro Ala Asn Met Leu
            260                 265                 270

Gly Tyr Asn Val Phe Ile Asp Gln Asp Phe Ser Gly Asp Asn Thr Arg
        275                 280                 285

Leu Gly Ile Gly Gly Glu Tyr Trp Arg Asp Tyr Phe Lys Ser Ser Val
    290                 295                 300

Asn Gly Tyr Phe Arg Met Arg Arg Trp His Glu Ser Tyr His Lys Lys
305                 310                 315                 320

Asp Tyr Asp Glu Arg Pro Ala Asn Gly Phe Asp Ile Arg Phe Asn Gly
                325                 330                 335

Tyr Leu Pro Ser Tyr Pro Ala Leu Gly Ala Lys Leu Ile Tyr Glu Gln
            340                 345                 350

Tyr Tyr Gly Asp Asn Val Ala Leu Phe Asn Ser Asp Lys Leu Gln Ser
        355                 360                 365

Asn Pro Gly Ala Ala Thr Val Gly Val Asn Tyr Thr Pro Ile Pro Leu
```

-continued

```
          370                 375                 380
Val Thr Met Gly Ile Asp Tyr Arg His Gly Thr Gly Asn Glu Asn Asp
385                 390                 395                 400
Leu Leu Tyr Ser Met Gln Phe Arg Tyr Gln Phe Asp Lys Ser Trp Ser
                405                 410                 415
Gln Gln Ile Glu Pro Gln Tyr Val Asn Glu Leu Arg Thr Leu Ser Gly
                420                 425                 430
Ser Arg Tyr Asp Leu Val Gln Arg Asn Asn Asn Ile Ile Leu Glu Tyr
            435                 440                 445
Lys Lys Gln Asp Ile Leu Ser Leu Asn Ile Pro His Asp Ile Asn Gly
            450                 455                 460
Thr Glu His Ser Thr Gln Lys Ile Gln Leu Ile Val Lys Ser Lys Tyr
465                 470                 475                 480
Gly Leu Asp Arg Ile Val Trp Asp Asp Ser Ala Leu Arg Ser Gln Gly
                485                 490                 495
Gly Gln Ile Gln His Ser Gly Ser Gln Ser Ala Gln Asp Tyr Gln Ala
                500                 505                 510
Ile Leu Pro Ala Tyr Val Gln Gly Gly Ser Asn Ile Tyr Lys Val Thr
            515                 520                 525
Ala Arg Ala Tyr Asp Arg Asn Gly Asn Ser Ser Asn Asn Val Gln Leu
            530                 535                 540
Thr Ile Thr Val Leu Ser Asn Gly Gln Val Val Asp Gln Val Gly Val
545                 550                 555                 560
Thr Asp Phe Thr Ala Asp Lys Thr Ser Ala Lys Ala Asp Asn Ala Asp
                565                 570                 575
Thr Ile Thr Tyr Thr Ala Thr Val Lys Lys Asn Gly Val Ala Gln Ala
                580                 585                 590
Asn Val Pro Val Ser Phe Asn Ile Val Ser Gly Thr Ala Thr Leu Gly
            595                 600                 605
Ala Asn Ser Ala Lys Thr Asp Ala Asn Gly Lys Ala Thr Val Thr Leu
            610                 615                 620
Lys Ser Ser Thr Pro Gly Gln Val Val Val Ser Ala Lys Thr Ala Glu
625                 630                 635                 640
Met Ser Ser Ala Leu Asn Ala Ser Ala Val Ile Phe Phe Asp Gln Thr
                645                 650                 655
Lys Ala Ser Ile Thr Glu Ile Lys Ala Asp Lys Thr Thr Ala Val Ala
                660                 665                 670
Asn Gly Lys Asp Ala Ile Lys Tyr Thr Val Lys Val Met Lys Asn Gly
            675                 680                 685
Gln Pro Val Asn Asn Gln Ser Val Thr Phe Ser Thr Asn Phe Gly Met
            690                 695                 700
Phe Asn Gly Lys Ser Gln Thr Gln Ala Thr Thr Gly Asn Asp Gly Arg
705                 710                 715                 720
Ala Thr Ile Thr Leu Thr Ser Ser Ala Gly Lys Ala Thr Val Ser
                725                 730                 735
Ala Thr Val Ser Asp Gly Ala Glu Val Lys Ala Thr Glu Val Thr Phe
                740                 745                 750
Phe Asp Glu Leu Lys Ile Asp Asn Lys Val Asp Ile Ile Gly Asn Asn
            755                 760                 765
Val Arg Gly Glu Leu Pro Asn Ile Trp Leu Gln Tyr Gly Gln Phe Lys
            770                 775                 780
Leu Lys Ala Ser Gly Gly Asp Gly Thr Tyr Ser Trp Tyr Ser Glu Asn
785                 790                 795                 800
```

```
Thr Ser Ile Ala Thr Val Asp Ala Ser Gly Lys Val Thr Leu Asn Gly
            805                 810                 815

Lys Gly Ser Val Val Ile Lys Ala Thr Ser Gly Asp Lys Gln Thr Val
        820                 825                 830

Ser Tyr Thr Ile Lys Ala Pro Ser Tyr Met Ile Lys Val Asp Lys Gln
        835                 840                 845

Ala Tyr Tyr Ala Asp Ala Met Ser Ile Cys Lys Asn Leu Leu Pro Ser
    850                 855                 860

Thr Gln Thr Val Leu Ser Asp Ile Tyr Asp Ser Trp Gly Ala Ala Asn
865                 870                 875                 880

Lys Tyr Ser His Tyr Ser Ser Met Asn Ser Ile Thr Ala Trp Ile Lys
            885                 890                 895

Gln Thr Ser Ser Glu Gln Arg Ser Gly Val Ser Ser Thr Tyr Asn Leu
        900                 905                 910

Ile Thr Gln Asn Pro Leu Pro Gly Val Asn Val Asn Thr Pro Asn Val
        915                 920                 925

Tyr Ala Val Cys Val Glu
    930

(2) INFORMATION FOR SEQ ID NO: 20:

(i) SEQUENCE CHARACTERISTICS:
        (A) LENGTH: 3131 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

TCGAGAATGA AATAGAAGTC GTTGTTAAGT CAATGGAAAA CCTGTATTTG GTATTACATA      60

ATCAGGGAAT AACATTAGAA AACGAACATA TGAAAATAGA GGAAATCAGT TCAAGCGACA     120

ATAAACATTA TTACGCCGGA AGATAAAATC CGATCTATTA ATATAATTTA TTTCTCATTC     180

TAACTCATTG TGGTGGAGCC ATAACATGAT TACTCATGGT TGTTATACCC GGACCCGGCA     240

CAAGCATAAG CTAAAAAAAA CATTGATTAT GCTTAGTGCT GGTTTAGGAT TGTTTTTTTA     300

TGTTAATCAG AATTCATTTG CAAATGGTGA AAATTATTTT AAATTGGGTT CGGATTCAAA     360

ACTGTTAACT CATGATAGCT ATCAGAATCG CCTTTTTTAT ACGTTGAAAA CTGGTGAAAC     420

TGTTGCCGAT CTTTCTAAAT CGCAAGATAT TAATTTATCG ACGATTTGGT CGTTGAATAA     480

GCATTTATAC AGTTCTGAAA GCGAAATGAT GAAGGCCGCG CCTGGTCAGC AGATCATTTT     540

GCCACTCAAA AAACTTCCCT TTGAATACAG TGCACTACCA CTTTTAGGTT CGGCACCTCT     600

TGTTGCTGCA GGTGGTGTTG CTGGTCACAC GAATAAACTG ACTAAAATGT CCCCGGACGT     660

GACCAAAAGC AACATGACCG ATGACAAGGC ATTAAATTAT GCGGCACAAC AGGCGGCGAG     720

TCTCGGTAGC CAGCTTCAGT CGCGATCTCT GAACGGCGAT TACGCGAAAG ATACCGCTCT     780

TGGTATCGCT GGTAACCAGG CTTCGTCACA GTTGCAGGCC TGGTTACAAC ATTATGGAAC     840

GGCAGAGGTT AATCTGCAGA GTGGTAATAA CTTTGACGGT AGTTCACTGG ACTTCTTATT     900

ACCGTTCTAT GATTCCGAAA AAATGCTGGC ATTTGGTCAG GTCGGAGCGC GTTACATTGA     960

CTCCCGCTTT ACGGCAAATT TAGGTGCGGG TCAGCGTTTT TTCCTTCCTG CAAACATGTT    1020

GGGCTATAAC GTCTTCATTG ATCAGGATTT TTCTGGTGAT AATACCCGTT TAGGTATTGG    1080

TGGCGAATAC TGGCGAGACT ATTTCAAAAG TAGCGTTAAC GGCTATTTCC GCATGAGCGG    1140
```

-continued

```
CTGGCATGAG TCATACAATA AGAAAGACTA TGATGAGCGC CCAGCAAATG GCTTCGATAT       1200

CCGTTTTAAT GGCTATCTAC CGTCATATCC GGCATTAGGC GCCAAGCTGA TATATGAGCA       1260

GTATTATGGT GATAATGTTG CTTTGTTTAA TTCTGATAAG CTGCAGTCGA ATCCTGGTGC       1320

GGCGACCGTT GGTGTAAACT ATACTCCGAT TCCTCTGGTG ACGATGGGGA TCGATTACCG       1380

TCATGGTACG GGTAATGAAA ATGATCTCCT TTACTCAATG CAGTTCCGTT ATCAGTTTGA       1440

TAAATCGTGG TCTCAGCAAA TTGAACCACA GTATGTTAAC GAGTTAAGAA CATTATCAGG       1500

CAGCCGTTAC GATCTGGTTC AGCGTAATAA CAATATTATT CTGGAGTACA AGAAGCAGGA       1560

TATTCTTTCT CTGAATATTC CGCATGATAT TAATGGTACT GAACACAGTA CGCAGAAGAT       1620

TCAGTTGATC GTTAAGAGCA AATACGGTCT GGATCGTATC GTCTGGGATG ATAGTGCATT       1680

ACGCAGTCAG GGCGGTCAGA TTCAGCATAG CGGAAGCCAA AGCGCACAAG ACTACCAGGC       1740

TATTTTGCCT GCTTATGTGC AAGGTGGCAG CAATATTTAT AAAGTGACGG CTCGCGCCTA       1800

TGACCGTAAT GGCAATAGCT CTAACAATGT ACAGCTTACT ATTACCGTTC TGTCGAATGG       1860

TCAAGTTGTC GACCAGGTTG GGGTAACGGA CTTTACGGCG GATAAGACTT CGGCTAAAGC       1920

GGATAACGCC GATACCATTA CTTATACCGC GACGGTGAAA AAGAATGGGG TAGCTCAGGC       1980

TAATGTCCCT GTTTCATTTA ATATTGTTTC AGGAACTGCA ACTCTTGGGG CAAATAGTGC       2040

CAAAACGGAT GCTAACGGTA AGGCAACCGT AACGTTGAAG TCGAGTACGC CAGGACAGGT       2100

CGTCGTGTCT GCTAAAACCG CGGAGATGAC TTCAGCACTT AATGCCAGTG CGGTTATATT       2160

TTTTGATCAA ACCAAGGCCA GCATTACTGA GATTAAGGCT GATAAGACAA CTGCAGTAGC       2220

AAATGGTAAG GATGCTATTA AATATACTGT AAAAGTTATG AAAAACGGTC AGCCAGTTAA       2280

TAATCAATCC GTTACATTCT CAACAAACTT TGGGATGTTC AACGGTAAGT CTCAAACGCA       2340

AGCAACCACG GGAAATGATG GTCGTGCGAC GATAACACTA ACTTCCAGTT CCGCCGGTAA       2400

AGCGACTGTT AGTGCGACAG TCAGTGATGG GGCTGAGGTT AAAGCGACTG AGGTCACTTT       2460

TTTTGATGAA CTGAAAATTG ACAACAAGGT TGATATTATT GGTAACAATG TCAAGAGGTC       2520

GATGTTGCCT AATATTTGGC TGCAATATGG TCAGTTTAAA CTGAAAGCAA GCGGTGGTGA       2580

TGGTACATAT TCATGGTATT CAGAAAATAC CAGTATCGCG ACTGTCGATG CATCAGGGAA       2640

AGTCACTTTG AATGGTAAAG GCAGTGTCGT AATTAAAGCC ACATCTGGTG ATAAGCAAAC       2700

AGTAAGTTAC ACTATAAAAG CACCGTCGTA TATGATAAAA GTGGATAAGC AAGCCTATTA       2760

TGCTGATGCT ATGTCCATTT GCAAAAATTT ATTACCATCC ACACAGACGG TATTGTCAGA       2820

TATTTATGAC TCATGGGGGG CTGCAAATAA ATATAGCCAT TATAGTTCTA TGAACTCAAT       2880

AACTGCTTGG ATTAAACAGA CATCTAGTGA GCAGCGTTCT GGAGTATCAA GCACTTATAA       2940

CCTAATAACA CAAAACCCTC TTCCTGGGGT TAATGTTAAT ACTCCAAATG TCTATGCGGT       3000

TTGTGTAGAA TAATTCCATA ACCACCCCGG CTAAAATATG TATTGTTTTA GTCGGGGCAT       3060

AATTATTTCT TCTTAAGAAA TAACCCTCTT ATAATCAAAT CTACTACTGG TCTTTTTATC       3120

TGCTTAATAG G                                                          3131
```

(2) INFORMATION FOR SEQ ID NO: 21:

(i) SEQUENCE CHARACTERISTICS:
        (A) LENGTH: 3106 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
GGAAAGATAA ATCCGATCTA TTAATATAAT TTATTTCTCA TTCTAACTCA TTGTGGTGGA      60
GCCATAACAT GAGTACTCAT GGTTGTTATA CCCGGACCCG GCACAAGCAT AAGCTAAAAA     120
AAACATTGAT TATGCTTAGT GCTGGTTTAG GATTGTTTTT TTATGTTAAT CAGAATTCAT     180
TTGCAAATGG TGAAAATTAT TTTAAATTGG GTTCGGATTC AAAACTGTTA ACTCATGATA     240
GCTATCAGAA TCGCCTTTTT TATACGTTGA AAACTGGTGA AACTGTTGCC GATCTTTCTA     300
AATCGCAAGA TATTAATTTA TCGACGATTT GGTCGTTGAA TAAGCATTTA TACAGTTCTG     360
AAAGCGAAAT GATGAAGGCC GCGCCTGGTC AGCAGATCAT TTTGCCACTC AAAAAACTTC     420
CCTTTGAATA CAGTGCACTA CCACTTTTAG GTTCGGCACC TCTTGTTGCT GCAGGTGGTG     480
TTGCTGGTCA CACGAATAAA CTGACTAAAA TGTCCCCGGA CGTGACCAAA AGCAACATGA     540
CCGATGACAA GGCATTAAAT TATGCGGCAC AACAGGCGGC GAGTCTCGGT AGCCAGCTTC     600
AGTCGCGATC TCTGAACGGC GATTACGCGA AGATACCGC TCTTGGTATC GCTGGTAACC     660
AGGCTTCGTC ACAGTTGCAG GCCTGGTTAC AACATTATGG AACGGCAGAG GTTAATCTGC     720
AGAGTGGTGA TAACTTTGAC GGTAGTTCAC TGGACTTCTT ATTACCGTTC TATGATTCCG     780
AAAAAATGCT GGCATTTGGT CAGGTCGGAG CGCGTTACAT TGACTCCCGC TTTACGGCAA     840
ATTTAGGTGC GGGTCAGCGT TTTTTCCTTC CTGCAAACAT GTTGGGCTAT AACGTCTTCA     900
TTGATCAGGA TTTTTCTGGT GATAATACCC GTTTAGGTAT TGGTGGCGAA TACTGGCGAG     960
ACTATTTCAA AAGTAGCGTT AACGGCTATT TCCGCATGAG GCGCTGGCAT GAGTCATACC    1020
ATAAGAAAGA CTATGATGAG CGCCCAGCAA ATGGCTTCGA TATCCGTTTT AATGGCTATC    1080
TACCGTCATA TCCGGCATTA GGCGCCAAGC TGATATATGA GCAGTATTAT GGTGATAATG    1140
TTGCTTTGTT TAATTCTGAT AAGCTGCAGT CGAATCCTGG TGCGGCGACC GTTGGTGTAA    1200
ACTATACTCC GATTCCTCTG GTGACGATGG GGATCGATTA CCGTCATGGT ACGGGTAATG    1260
AAAATGATCT CCTTTACTCA ATGCAGTTCC GTTATCAGTT TGATAAATCG TGGTCTCAGC    1320
AAATTGAACC ACAGTATGTT AACGAGTTAA GAACATTATC AGGCAGCCGT TACGATCTGG    1380
TTCAGCGTAA TAACAATATT ATTCTGGAGT ACAAGAAGCA GGATATTCTT TCTCTGAATA    1440
TTCCGCATGA TATTAATGGT ACTGAACACA GTACGCAGAA GATTCAGTTG ATCGTTAAGA    1500
GCAAATACGG TCTGGATCGT ATCGTCTGGG ATGATAGTGC ATTACGCAGT CAGGGCGGTC    1560
AGATTCAGCA TAGCGGAAGC CAAAGCGCAC AAGACTACCA GGCTATTTTG CCTGCTTATG    1620
TGCAAGGTGG CAGCAATATT TATAAAGTGA CGGCTCGCGC CTATGACCGT AATGGCAATA    1680
GCTCTAACAA TGTACAGCTT ACTATTACCG TTCTGTCGAA TGGTCAAGTT GTCGACCAGG    1740
TTGGGGTAAC GGACTTTACG GCGGATAAGA CTTCGGCTAA AGCGGATAAC GCCGATACCA    1800
TTACTTATAC CGCGACGGTG AAAAAGAATG GGGTAGCTCA GGCTAATGTC CCTGTTTCAT    1860
TTAATATTGT TTCAGGAACT GCAACTCTTG GGGCAAATAG TGCCAAAACG GATGCTAACG    1920
GTAAGGCAAC CGTAACGTTG AAGTCGAGTA CGCCAGGACA GGTCGTCGTG TCTGCTAAAA    1980
CCGCGGAGAT GAGTTCAGCA CTTAATGCCA GTGCGGTTAT ATTTTTTGAT CAAACCAAGG    2040
CCAGCATTAC TGAGATTAAG GCTGATAAGA CAACTGCAGT AGCAAATGGT AAGGATGCTA    2100
TTAAATATAC TGTAAAAGTT ATGAAAAACG GTCAGCCAGT TAATAATCAA TCCGTTACAT    2160
TCTCAACAAA CTTTGGGATG TTCAACGGTA AGTCTCAAAC GCAAGCAACC ACGGGAAATG    2220
ATGGTCGTGC GACGATAACA CTAACTTCCA GTTCCGCCGG TAAAGCGACT GTTAGTCGCA    2280
CAGTCAGTGA TGGGGCTGAG GTTAAAGCGA CTGAGGTCAC TTTTTTTGAT GAACTGAAAA    2340
```

```
TTGACAACAA GGTTGATATT ATTGGTAACA ATGTCAGAGG CGAGTTGCCT AATATTTGGC    2400

TGCAATATGG TCAGTTTAAA CTGAAAGCAA GCGGTGGTGA TGGTACATAT TCATGGTATT    2460

CAGAAAATAC CAGTATCGCG ACTGTCGATG CATCAGGGAA AGTCACTTTG AATGGTAAAG    2520

GCAGTGTCGT AATTAAAGCC ACATCTGGTG ATAAGCAAAC AGTAAGTTAC ACTATAAAAG    2580

CACCGTCGTA TATGATAAAA GTGGATAAGC AAGCCTATTA TGCTGATGCT ATGTCCATTT    2640

GCAAAAATTT ATTACCATCC ACACAGACGG TATTGTCAGA TATTTATGAC TCATGGGGGG    2700

CTGCAAATAA ATATAGCCAT TATAGTTCTA TGAACTCAAT AACTGCTTGG ATTAAACAGA    2760

CATCTAGTGA GCAGCGTTCT GGAGTATCAA GCACTTATAA CCTAATAACA CAAAACCCTC    2820

TTCCTGGGGT TAATGTTAAT ACTCCAAATG TCTATGCGGT TTGTGTAGAA TAATTCCATA    2880

ACCACCCCGG CTAAAATATG TATTGTTTTA GTCGGGCAT AATTATTTCT TCTTAAGAAA     2940

TAACCTCTTA TAATCAAATC TACTACTGGT CTTTTTATCT GCTTAATAGG TCTCTTTCAA    3000

AGAGACACAT TCACGTTTTC TAGAGTAGGT TGATCCAACC ACGCTGTATA CCAAAGCTGA    3060

ATCACATCAA GCAACAACTA TGCTCACAAC ATCCACACAA TAAAAA                  3106

(2) INFORMATION FOR SEQ ID NO: 22:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

ATGAGAGGAT CGCAYCAYCA YCAYCAYCAY GGATCCGCAT GCGACTCGGT ACCCCGGGTC    60

GACCTGCAGC CAAGCTTAAT TAGCTGAG                                      88

(2) INFORMATION FOR SEQ ID NO: 23:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

ATGAGAGGAT CTCAYCAYCA YCAYCAYCAY ACGGATCCGC ATGCGAGCTC GGTACCCCGG    60

GTCGACCTGC AGCCAAGCTT AATTAGCTGA G                                  91

(2) INFORMATION FOR SEQ ID NO: 24:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

ATGAGAGGAT CTCAYCAYCA YCAYCAYCAY GGGATCCGCA TGCGAGCTCG GTACCCCGGG    60

TCGACCTGCA GCCAAGCTTA ATTAGCTGAG                                    90
```

(2) INFORMATION FOR SEQ ID NO: 25:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

```
CTCGAGAAAT CATAAAAAAT TTATTTGCTT TGTGAGCGGA TAACAATTAT AATAGATTCA      60
ATTGTGAGCG GATAACAATT TCACACAGAA TTCATTAAAG AGGAGAAATT AACTATGAGA     120
GGATCGCATC ACCATCACCA TCACGGATCC GCATGCGAGC TCGGTACCCC GGGTCGACCT     180
GCAGCCAAGC TTAATTAGCT GAGCTTGGAC TCCTGTTGAT AGATCCAGTA ATGACCTCAG     240
AACTCCATCT                                                            250
```

(2) INFORMATION FOR SEQ ID NO: 26:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

```
Asp Asp Asp Asp Lys
1               5
```

(2) INFORMATION FOR SEQ ID NO: 27:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

```
Ser Glu Lys Asp Glu Leu
1               5
```